(12) United States Patent
Yu et al.

(10) Patent No.: US 9,249,466 B2
(45) Date of Patent: Feb. 2, 2016

(54) METHODS AND COMPOSITIONS FOR TREATING CANCER

(75) Inventors: Qiang Yu, Singapore (SG); Jing Tan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/520,472

(22) PCT Filed: Jan. 10, 2011

(86) PCT No.: PCT/SG2011/000011
§ 371 (c)(1),
(2), (4) Date: Jul. 3, 2012

(87) PCT Pub. No.: WO2011/084108
PCT Pub. Date: Jul. 14, 2011

(65) Prior Publication Data
US 2013/0123328 A1    May 16, 2013

(30) Foreign Application Priority Data

Jan. 8, 2010   (SG) .............................. 201000114-7
Mar. 4, 2010   (SG) .............................. 201001629-3

(51) Int. Cl.
| | | |
|---|---|---|
| C12N 15/11 | (2006.01) |
| C12Q 1/68 | (2006.01) |
| A61K 45/06 | (2006.01) |
| G01N 33/574 | (2006.01) |
| A61K 31/436 | (2006.01) |
| A61K 31/506 | (2006.01) |
| A61K 31/713 | (2006.01) |
| C12Q 1/42 | (2006.01) |
| G01N 33/68 | (2006.01) |

(52) U.S. Cl.
CPC ............ *C12Q 1/6886* (2013.01); *A61K 31/436* (2013.01); *A61K 31/506* (2013.01); *A61K 31/713* (2013.01); *A61K 45/06* (2013.01); *C12Q 1/42* (2013.01); *G01N 33/57407* (2013.01); *G01N 33/6893* (2013.01)

(58) Field of Classification Search
None
See application file for complete search history.

(56) References Cited

U.S. PATENT DOCUMENTS

2004/0186065 A1   9/2004   Ionescu et al.
2005/0216961 A1   9/2005   Delaney

FOREIGN PATENT DOCUMENTS

| GB | 2488028 A | 8/2012 |
| WO | WO-2005/007846 A1 | 1/2005 |
| WO | WO-2007/017047 A1 | 2/2007 |
| WO | WO-2007/047754 A2 | 4/2007 |
| WO | WO-2008/005457 A2 | 1/2008 |

OTHER PUBLICATIONS

Peifer et al., New anti-cancer role for PDK1 inhibitors: preventing resistance to tamoxifen, 2009, Biochem J, 417:e5-e7.*
Feldman et al., Novel Small Molecule Inhibitors of 3-Phosphoinositide-dependent Kinase-1, The Journal of Biological Chemistry, 2005, pp. 19867-19874, vol. 280, No. 20.
Falasca et al., A novel inhibitor of the PI3k/Akt pathway based on the structure of inositol 1,3,4,5,6-pentakisphosphate, British Journal of Cancer, 2010, pp. 104-114, vol. 102.
Peifer et al., New anti-cancer role for PDK1 inhibitors: preventing resistance to tamoxifen, Biochem. J., 2009, pp. e5-e7, vol. 417.
Weisberg et al., Potentiation of antileukemic therapies by the dual PI3k/PDK-1 inhibitor BAG956: effects on BCR-ABL- and mutant FLT3-expressing cells, Blood, 2008, pp. 3723-3734, vol. 111, No. 7.
Jing Tan, et al., B55β-Associated PP2A Complex Controls PDK1-Directed Myc Signaling and Modulates Rapamycin Sensitivity in Colorectal Cancer, Cancer Cell, 2010, 459-471, vol. 18.
International Search Report for PCT/SG2011/000011, dated Apr. 8, 2011, 5 pages.
Written Opinion for for PCT/SG2011/000011, dated Apr. 8, 2011, 11 pages.
Tan, J. and Yu, Q, PDK1-driven Myc signaling regulates cellular response to mTOR inhibitors, Cell Cycle, 10(7):1019-1020 (2011).
Yuan, R.R. et al., Targeting tumorigenesis: development and use of m TOR inhibitors in cancer therapy, Journal of Hematology & Oncology, 2(45):1-12 (2009).

* cited by examiner

*Primary Examiner* — Mark Shibuya
*Assistant Examiner* — Kate Poliakova
(74) *Attorney, Agent, or Firm* — Choate, Hall & Stewart LLP; Charles E. Lyon; Nishat A. Shaikh

(57) ABSTRACT

We describe a method of determining whether a cancer cell is likely to be resistant to treatment by an mTOR inhibitor. The method may comprise detecting PPP2R2B (GenBank Accession Number: NM_18167) in or of the cell. It may, alternatively, or in addition, comprise detecting PDK1 (GenBank Accession Number: NM_002613), in or of the cell. The method may comprise detecting methylation of the PPP2R2B promoter in or of the cell. It may comprise detecting the expression and/or activity of PPP2R2B in or of the cell. It may comprise detecting PDK1 mediated Myc phosphorylation activity. Methods of choosing a treatment for an individual suffering from or suspected to be suffering from a cancer, determining whether an individual suffering from or suspected to be suffering from a cancer will respond to treatment by an mTOR inhibitor, increasing the sensitivity of a cancer cell to treatment by an mTOR inhibitor, for treating or preventing cancer in an individual suffering or suspected to be suffering from cancer are also provided. We further provide for a combination of an inhibitor of PDK1 expression and/or activity and an mTOR inhibitor for use in a method of treatment or prevention of cancer.

18 Claims, 85 Drawing Sheets

SA-β-gal

Vector PPP2R2B

−Dox

+Dox siNC

SV40-ST si*PPP2R2B*#SP si*PPP2R2B*#1 pMN

PMN-*PPP2R2B*

DLD1 48h

SW480 48h

HEK pMN

HEK PDK1

HEK PIK3CA-E545K

HEK shPTEN

Control  BI2536

SEQUENCE LISTING

```
<160> NUMBER OF SEQ ID NOS: 15

<210> SEQ ID NO 1
<211> LENGTH: 2549
<212> TYPE: PRT
<213> ORGANISM: Mus musculus

<400> SEQUENCE: 1

Met Leu Gly Thr Gly Pro Ala Val Ala Thr Ala Ser Ala Ala Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ser Thr Arg Ile Gly Arg Phe Ala Asn Tyr Leu Arg
            100                 105                 110

Asn Leu Leu Pro Ser Ser Asp Pro Val Val Met Glu Met Ala Ser Lys
        115                 120                 125
```

```
Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
                180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Pro Asn Ala Leu Val Gly Leu Leu Gly Tyr
                325                 330                 335

Ser Ser Pro Gln Gly Leu Met Gly Phe Gly Thr Ser Pro Ser Pro Ala
                340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Ser Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
                420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
    450                 455                 460

Pro Lys Asp Phe Ala His Lys Arg Gln Lys Thr Val Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
530                 535                 540
```

-continued

```
Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Ala Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
    610                 615                 620

Thr Cys Ser Cys Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
                660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
            820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
930                 935                 940

Glu Phe Tyr Pro Ala Val Ser Met Val Ala Leu Met Arg Ile Phe Arg
945                 950                 955                 960
```

Asp Gln Ser Leu Ser His His His Thr Met Val Val Gln Ala Ile Thr
            965                 970                 975

Phe Ile Phe Lys Ser Leu Gly Leu Lys Cys Val Gln Phe Leu Pro Gln
            980                 985                 990

Val Met Pro Thr Phe Leu Asn Val  Ile Arg Val Cys  Asp Gly Ala Ile
            995                 1000                1005

Arg Glu Phe Leu Phe Gln Gln  Leu Gly Met Leu Val  Ser Phe Val
            1010                1015                1020

Lys Ser His Ile Arg Pro Tyr  Met Asp Glu Ile Val  Thr Leu Met
            1025                1030                1035

Arg Glu Phe Trp Val Met Asn  Thr Ser Ile Gln Ser  Thr Ile Ile
            1040                1045                1050

Leu Leu Ile Glu Gln Ile Val  Val Ala Leu Gly Gly  Glu Phe Lys
            1055                1060                1065

Leu Tyr Leu Pro Gln Leu Ile  Pro His Met Leu Arg  Val Phe Met
            1070                1075                1080

His Asp Asn Ser Gln Gly Arg  Ile Val Ser Ile Lys  Leu Leu Ala
            1085                1090                1095

Ala Ile Gln Leu Phe Gly Ala  Asn Leu Asp Asp Tyr  Leu His Leu
            1100                1105                1110

Leu Leu Pro Pro Ile Val Lys  Leu Phe Asp Ala Pro  Glu Val Pro
            1115                1120                1125

Leu Pro Ser Arg Lys Ala Ala  Leu Glu Thr Val Asp  Arg Leu Thr
            1130                1135                1140

Glu Ser Leu Asp Phe Thr Asp  Tyr Ala Ser Arg Ile  Ile His Pro
            1145                1150                1155

Ile Val Arg Thr Leu Asp Gln  Ser Pro Glu Leu Arg  Ser Thr Ala
            1160                1165                1170

Met Asp Thr Leu Ser Ser Leu  Val Phe Gln Leu Gly  Lys Lys Tyr
            1175                1180                1185

Gln Ile Phe Ile Pro Met Val  Asn Lys Val Leu Val  Arg His Arg
            1190                1195                1200

Ile Asn His Gln Arg Tyr Asp  Val Leu Ile Cys Arg  Ile Val Lys
            1205                1210                1215

Gly Tyr Thr Leu Ala Asp Glu  Glu Glu Asp Pro Leu  Ile Tyr Gln
            1220                1225                1230

His Arg Met Leu Arg Ser Ser  Gln Gly Asp Ala Leu  Ala Ser Gly
            1235                1240                1245

Pro Val Glu Thr Gly Pro Met  Lys Lys Leu His Val  Ser Thr Ile
            1250                1255                1260

Asn Leu Gln Lys Ala Trp Gly  Ala Ala Arg Arg Val  Ser Lys Asp
            1265                1270                1275

Asp Trp Leu Glu Trp Leu Arg  Arg Leu Ser Leu Glu  Leu Leu Lys
            1280                1285                1290

Asp Ser Ser Pro Ser Leu  Arg Ser Cys Trp Ala  Leu Ala Gln
            1295                1300                1305

Ala Tyr Asn Pro Met Ala Arg  Asp Leu Phe Asn Ala  Ala Phe Val
            1310                1315                1320

Ser Cys Trp Ser Glu Leu Asn  Glu Asp Gln Gln Asp  Glu Leu Ile
            1325                1330                1335

Arg Ser Ile Glu Leu Ala Leu  Thr Ser Gln Asp Ile  Ala Glu Val
            1340                1345                1350

-continued

Thr Gln Thr Leu Leu Asn Leu Ala Glu Phe Met Glu His Ser Asp
1355                1360                1365

Lys Gly Pro Leu Pro Leu Arg Asp Asp Asn Gly Ile Val Leu Leu
1370                1375                1380

Gly Glu Arg Ala Ala Lys Cys Arg Ala Tyr Ala Lys Ala Leu His
1385                1390                1395

Tyr Lys Glu Leu Glu Phe Gln Lys Gly Pro Thr Pro Ala Ile Leu
1400                1405                1410

Glu Ser Leu Ile Ser Ile Asn Asn Lys Leu Gln Gln Pro Glu Ala
1415                1420                1425

Ala Ser Gly Val Leu Glu Tyr Ala Met Lys His Phe Gly Glu Leu
1430                1435                1440

Glu Ile Gln Ala Thr Trp Tyr Glu Lys Leu His Glu Trp Glu Asp
1445                1450                1455

Ala Leu Val Ala Tyr Asp Lys Lys Met Asp Thr Asn Lys Glu Asp
1460                1465                1470

Pro Glu Leu Met Leu Gly Arg Met Arg Cys Leu Glu Ala Leu Gly
1475                1480                1485

Glu Trp Gly Gln Leu His Gln Gln Cys Cys Glu Lys Trp Thr Leu
1490                1495                1500

Val Asn Asp Glu Thr Gln Ala Lys Met Ala Arg Met Ala Ala Ala
1505                1510                1515

Ala Ala Trp Gly Leu Gly Gln Trp Asp Ser Met Glu Glu Tyr Thr
1520                1525                1530

Cys Met Ile Pro Arg Asp Thr His Asp Gly Ala Phe Tyr Arg Ala
1535                1540                1545

Val Leu Ala Leu His Gln Asp Leu Phe Ser Leu Ala Gln Gln Cys
1550                1555                1560

Ile Asp Lys Ala Arg Asp Leu Leu Asp Ala Glu Leu Thr Ala Met
1565                1570                1575

Ala Gly Glu Ser Tyr Ser Arg Ala Tyr Gly Ala Met Val Ser Cys
1580                1585                1590

His Met Leu Ser Glu Leu Glu Glu Val Ile Gln Tyr Lys Leu Val
1595                1600                1605

Pro Glu Arg Arg Glu Ile Ile Arg Gln Ile Trp Trp Glu Arg Leu
1610                1615                1620

Gln Gly Cys Gln Arg Ile Val Glu Asp Trp Gln Lys Ile Leu Met
1625                1630                1635

Val Arg Ser Leu Val Val Ser Pro His Glu Asp Met Arg Thr Trp
1640                1645                1650

Leu Lys Tyr Ala Ser Leu Cys Gly Lys Ser Gly Arg Leu Ala Leu
1655                1660                1665

Ala His Lys Thr Leu Val Leu Leu Leu Gly Val Asp Pro Ser Arg
1670                1675                1680

Gln Leu Asp His Pro Leu Pro Thr Ala His Pro Gln Val Thr Tyr
1685                1690                1695

Ala Tyr Met Lys Asn Met Trp Lys Ser Ala Arg Lys Ile Asp Ala
1700                1705                1710

Phe Gln His Met Gln His Phe Val Gln Thr Met Gln Gln Gln Ala
1715                1720                1725

Gln His Ala Ile Ala Thr Glu Asp Gln Gln His Lys Gln Glu Leu
1730                1735                1740

His Lys Leu Met Ala Arg Cys Phe Leu Lys Leu Gly Glu Trp Gln
1745                1750                1755

Leu Asn Leu Gln Gly Ile Asn Glu Ser Thr Ile Pro Lys Val Leu
1760                1765                1770

Gln Tyr Tyr Ser Ala Ala Thr Glu His Asp Arg Ser Trp Tyr Lys
1775                1780                1785

Ala Trp His Ala Trp Ala Val Met Asn Phe Glu Ala Val Leu His
1790                1795                1800

Tyr Lys His Gln Asn Gln Ala Arg Asp Glu Lys Lys Lys Leu Arg
1805                1810                1815

His Ala Ser Gly Ala Asn Ile Thr Asn Ala Thr Thr Ala Ala Thr
1820                1825                1830

Thr Ala Ala Ser Ala Ala Ala Ala Thr Ser Thr Glu Gly Ser Asn
1835                1840                1845

Ser Glu Ser Glu Ala Glu Ser Asn Glu Asn Ser Pro Thr Pro Ser
1850                1855                1860

Pro Leu Gln Lys Lys Val Thr Glu Asp Leu Ser Lys Thr Leu Leu
1865                1870                1875

Leu Tyr Thr Val Pro Ala Val Gln Gly Phe Phe Arg Ser Ile Ser
1880                1885                1890

Leu Ser Arg Gly Asn Asn Leu Gln Asp Thr Leu Arg Val Leu Thr
1895                1900                1905

Leu Trp Phe Asp Tyr Gly His Trp Pro Asp Val Asn Glu Ala Leu
1910                1915                1920

Val Glu Gly Val Lys Ala Ile Gln Ile Asp Thr Trp Leu Gln Val
1925                1930                1935

Ile Pro Gln Leu Ile Ala Arg Ile Asp Thr Pro Arg Pro Leu Val
1940                1945                1950

Gly Arg Leu Ile His Gln Leu Leu Thr Asp Ile Gly Arg Tyr His
1955                1960                1965

Pro Gln Ala Leu Ile Tyr Pro Leu Thr Val Ala Ser Lys Ser Thr
1970                1975                1980

Thr Thr Ala Arg His Asn Ala Ala Asn Lys Ile Leu Lys Asn Met
1985                1990                1995

Cys Glu His Ser Asn Thr Leu Val Gln Gln Ala Met Met Val Ser
2000                2005                2010

Glu Glu Leu Ile Arg Val Ala Ile Leu Trp His Glu Met Trp His
2015                2020                2025

Glu Gly Leu Glu Glu Ala Ser Arg Leu Tyr Phe Gly Glu Arg Asn
2030                2035                2040

Val Lys Gly Met Phe Glu Val Leu Glu Pro Leu His Ala Met Met
2045                2050                2055

Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

-continued

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Thr Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

Thr Asn Thr Lys Gly Asn Lys Arg Ser Arg Thr Arg Thr Asp Ser
2435                2440                2445

Tyr Ser Ala Gly Gln Ser Val Glu Ile Leu Asp Gly Val Glu Leu
2450                2455                2460

Gly Glu Pro Ala His Lys Lys Ala Gly Thr Thr Val Pro Glu Ser
2465                2470                2475

Ile His Ser Phe Ile Gly Asp Gly Leu Val Lys Pro Glu Ala Leu
2480                2485                2490

Asn Lys Lys Ala Ile Gln Ile Ile Asn Arg Val Arg Asp Lys Leu
2495                2500                2505

Thr Gly Arg Asp Phe Ser His Asp Asp Thr Leu Asp Val Pro Thr
2510                2515                2520

```
Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtaccacca tggaggagga cattgatacc                                    30

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgagcagt taaccttgtc ctgga                                         25

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcgaattcgc caggaccacc agccagc                                       27

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagaattcct gcacagcggc gtccgg                                        26

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(18)
<223> OTHER INFORMATION: May or may not be present

<400> SEQUENCE: 6
tttttttttt tttttttt                                                 18

<210> SEQ ID NO 7
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atggaggagg acattgatac c                                            21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acattgtatt cacccctacg                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agtagtagtt gcgagtgcgc                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaacaaccgc gacaaaataa t                                            21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agtagtagta gttgtgagtg tgt                                          23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaacaaccac aacaaaataa tacc                                         24

<210> SEQ ID NO 13
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
attattgttg ttgggaaaga                                                    20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caaaataata cctttctaaa ccc                                                23

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gcuuacuuuc uucugucua                                                     19
```

METHODS AND COMPOSITIONS FOR TREATING CANCER

This application is a U.S. National Stage of International Application No. PCT/SG11/00011, filed Jan. 1, 2011, which claims the benefit of SG 201000114-7, filed Jan. 8, 2010 and SG 201001629-3. filed Mar. 4, 2010, the entire content of each of which is hereby incorporated herein by reference.

SEQUENCE LISTING

The instant application contains a Sequence Listing which has been submitted electronically in ASCII format and is hereby incorporated by reference in its entirety. Said ASCII copy, created on Nov. 4, 2015, is named 2008187-0034_SL.txt and is 26,017 bytes in size.

FIELD

The present invention relates to the fields of medicine, cell biology, molecular biology and genetics. This invention relates to the field of medicine. In particular, it relates to treatment and diagnosis of diseases such as cancer, as well as compositions for such use.

BACKGROUND

Protein phosphatase 2A (PP2A) functions as a multimetric enzyme that contains the catalytic C subunit, a scaffolding A-subunit and one of a large array of regulatory B-subunits. Eukaryotic cells contain over 200 biochemical distinct PP2A complexes derived from differential combinations of A, B, C and other subunits. The regulatory subunits are expressed in a tissue-specific manner, leading to the presence of different PP2A complexes in different mammalian tissues (Virshup and Shenolikar, 2009). Moreover, it is these regulators, rather than the catalytic subunit that provide the substrate specificity and to catalyze distinct dephosphorylation events to impose different functional outcomes.

Although a tumor suppressor role of PP2A has been shown in a variety of immortalized human cell types (Chen et al., 2004; Eichhorn et al., 2009; Janssens and Goris, 2001; Rangarajan et al., 2004; Sablina et al., 2007; Zhao et al., 2003), the genetic and/or the epigenetic evidence pointing to a prevalent inactivation of PP2A in human malignancy have not been reported. Somatic mutations in the A subunit of the PP2A complex, which can result in the loss of B subunit binding (Ruediger et al., 2001), were found only in up to 15% of some human cancers (Calin et al., 2000; Ruediger et al., 2001; Takagi et al., 2000; Tamaki et al., 2004; Wang et al., 1998; Westermarck and Hahn, 2008), and the reduced expression of PP2A subunit B56γ3 has been reported only in some cancer cell lines (Chen et al., 2004; Zhao et al., 2003). In general, the genetic or epigenetic changes of PP2A complexes in human cancer remains to be defined, as is its impact on cancer signaling or therapeutic responses to targeted therapy.

One of the PP2A regulated cancer signaling pathways is the mTOR pathway, a key component of PI3K pathway that many cancer cells are addicted to for growth advantage (Guertin and Sabatini, 2007; Sabatini, 2006). Although small molecule mTORC1 inhibitors, such as rapamycin and its analogues have shown promising rationals for their use in cancer therapy and have been approved for clinical application (Guertin and Sabatini, 2007; Hudes et al., 2007), these inhibitors have had only limited successes and the clinical outcome is unpredictable. While a known mechanism of rapamycin resistance is linked to its feedback activation of AKT phosphorylation through PI3K and mTORC2 (O'Reilly et al., 2006; Sarbaisov et al., 2006), further understanding the resistance mechanism and identifying the biomarkers that help to predict the therapeutic response have become important topics (Mao et al., 2008; Scott et al., 2009; Thomas et al., 2006).

SUMMARY

Here, we describe a B subunit of the PP2A holoenzyme, PPP2R2B, encoding B55β, epigenetically inactivated by promoter DNA hypermethylation in human colorectal cancer (CRC).

We show that PP2A-PPP2R2B complex functions as a tumor suppressor by mitigating PDK1-directed Myc phosphorylation. Loss of this specific PP2A complex in CRC resulted in strong Myc phosphorylation in response to mTORC1 inhibitor rapamycin, which confers rapamycin resistance.

Intriguingly, unlike rapamycin-induced AKT phosphorylation, rapamycin-induced Myc phosphorylation does not require PI3KCA, but is PDK1-dependent.

We therefore identify a new tumor suppressor mechanism controlling PDK1-Myc signaling and show that a defect in this regulation leads to resistance to mTOR-based cancer therapy.

According to a $1^{st}$ aspect of the present invention, we provide a method of determining whether a cancer cell is likely to be resistant to treatment by an mTOR inhibitor, the method comprising detecting: (i) PPP2R2B (GenBank Accession Number: NM_181678) or (ii) PDK1 (GenBank Accession Number: NM_002613), or both, in or of the cell.

The method may comprise detecting methylation of the PPP2R2B promoter in or of the cell. The method may comprise detecting hypermethylation of the PPP2R2B promoter. The methylation or hypermethylation may be compared to a cancer cell that is not mTOR inhibitor resistant. Detection of hypermethylation may indicate that the cancer cell is likely to be resistant to treatment by an mTOR inhibitor.

The method may comprise detecting expression or activity of PPP2R2B or PDK1, or both, in the cell. The PDK1 activity may comprise PDK1 mediated Myc phosphorylation activity.

The method may be such that a decreased expression and/or activity of PPP2R2B compared to a cancer cell that is not mTOR inhibitor resistant, indicates that the cancer cell is likely to be resistant to treatment by an mTOR inhibitor. The method may be such that an increased expression and/or activity of PDK1 compared to a cancer cell that is not mTOR inhibitor resistant, indicates that the cancer cell is likely to be resistant to treatment by an mTOR inhibitor.

There is provided, according to a $2^{nd}$ aspect of the present invention, a method of choosing a treatment for an individual suffering from or suspected to be suffering from a cancer, the method comprising: (a) providing a cell of the patient; (b) detecting mTOR inhibitor resistance of the cell by method as set out above; and (c) where the cell is determined not to be mTOR inhibitor resistant, choosing an mTOR inhibitor as a treatment for the individual, and where the cell is determined to be mTOR inhibitor resistant, choosing a different treatment for the individual.

We provide, according to a $3^{rd}$ aspect of the present invention, a method of determining whether an individual suffering from or suspected to be suffering from a cancer will respond to treatment by an mTOR inhibitor. The method may comprise performing a method as set out above on a cell of the individual. The method may comprise, where the cell is determined not to be mTOR inhibitor resistant, determining that the individual is likely to respond to treatment by an mTOR inhibitor.

As a 4th aspect of the present invention, there is provided a method of increasing the sensitivity of a cancer cell to treatment by an mTOR inhibitor, the method comprising increasing expression and/or activity of PPP2R2B, or decreasing expression and/or activity of PDK1, or both, in or of the cell.

We provide, according to a 5th aspect of the present invention, a method of treating or preventing cancer in an individual suffering or suspected to be suffering from cancer, the method comprising increasing expression and/or activity of PPP2R2B, or decreasing expression and/or activity of PDK1, or both, in or of the individual.

The method may be such that expression of PPP2R2B is increased by decreasing methylation of the PPP2R2B promoter. Methylation of the PPP2R2B promoter may be achieved by exposing the cell to, or administering to a patient, a demethylating agent such as 5-aza-dC or Azacitidine.

The method may comprise exposing the cell to, or administering to a patient, a PDK1 inhibitor such as BX912 (CAS Accession Number: 702674-56-4) or BX795 (CAS Accession Number: 702675-74-9).

The present invention, in a 6th aspect, provides a method of treating or preventing cancer in an individual suffering or suspected to be suffering from cancer, the method comprising administering an inhibitor of PDK1 expression and/or activity together with an mTOR inhibitor.

In a 7th aspect of the present invention, there is provided a combination of an inhibitor of PDK1 expression and/or activity and an mTOR inhibitor for use in a method of treatment or prevention of cancer.

According to an 8th aspect of the present invention, we provide use of a combination of an inhibitor of PDK1 expression and/or activity and an mTOR inhibitor in the manufacture of a medicament for the treatment or prevention of cancer.

We provide, according to a 9th aspect of the invention, use of PPP2R2B or PDK1, or both, as a biomarker for sensitivity of a cancer cell to an mTOR inhibitor or for colorectal cancer (CRC), such as rapamycin resistance colorectal cancer.

The mTOR inhibitor may comprise rapamycin or a derivative thereof. The PDK1 inhibitor may comprise a shRNA, BX912 or BX795 (or any combination of these).

There is provided, in accordance with a 10th aspect of the present invention, PDK1 or an antagonist thereof for use in a method of treating colorectal cancer (CRC).

The cancer may be selected from the group consisting of: colorectal cancer (CRC), bladder cancer, brain cancer and oesophageal cancer, preferably colorectal cancer (CRC).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 1A. Differential expression of PPP2R2B in 24 pairs of patient-derived CRC and matched normal colon mucosa as determined by Illumina array analysis: PPP2R2B-mRNA expression is presented relative to log 2. ** $p<0.001$.

FIG. 1B. Hierarchical clustering of PP2A subunits expression in 24 pairs of colorectal tumors (T) and matched normal mucosa (N).

FIG. 1C. RT-PCR analysis of PPP2R2B expression from eight randomly selected pairs of human CRC (T) and matched mucosa (N). β-actin was used as a PCR control.

FIG. 1D RT-PCR analysis of PPP2R2B, PPP2R2A and PPP2R5C in a panel of CRC cell lines compared to the normal colon tissue.

FIG. 1E. Methylation specific PCR (MSP) analysis of PPP2R2B promoter in CRC cell lines.

FIG. 1F. MSP analysis of PPP2R2B promoter in eight tumor and normal controls

FIG. 1G. RT-PCR analysis of PPP2R2B in HCT116 and DKO or DLD1 cells treated with or without 5-AzaC (5 μM) for 3 days.

FIG. 1H. MSP analysis of PPP2R2B promoter in HCT116 and DKO cells.

FIG. 1I. Methylation analysis of PPP2R2B promoter by bisulfite-sequencing analysis (BGS). The region analyzed is indicated. The arrow indicates the transcriptional start site. Open circles represent unmethylated CpGs; closed circles denote methylated CpGs.

FIG. 2B. SA-β-gal assay of DLD1-PPP2R2B or vector control cells treated with or without Dox for 96 hr. Scale bars=100 μM.

FIG. 2C. BrdU incorporation of DLD1-PPP2R2B or vector control cells treated with or without Dox for 96 h. Shown is mean+S.D. of three independent experiments. ** $p<0.001$.

FIG. 2D. Anchorage-independent growth assessed by soft agar assay in DLD1-PPP2R2B or HCT116-PPP2R2B cells, treated with or without Dox for 12 days.

FIG. 2E. Xenograft tumor growth of DLD1-PPP2R2B or control cells in nude mice treated with Dox at 100 mg/kg daily as described in Experimental Procedures. Error bars represents S.D.

FIG. 2F and FIG. 2G. HEK-TERV cells were transfected with a PPP2R2B smart pool siRNA (SP) or an independent PPP2R2B siRNA and the PPP2R2B mRNA was assessed by Taqman assay (FIG. 2F) and the colony formation capacity was assessed by soft-agar assay (FIG. 2G). Shown on the left are representative images of three independent experiments. SV40 small antigen (ST) expressing HEK-TERV cells were used as positive control.

FIG. 3B and FIG. 3C. Immunoblot analysis of DLD1-PPP2R2B or the vector control cells treated with or without Dox for the indicated length of times.

FIG. 3D. Co-immunoprecipitation of PP2A scaffolding A subunit and catalytic C subunit with PPP2R2B. DLD1-PPP2R2B or vector control cells were treated with Dox and PPP2R2B was immunoprecipitated with anti-Myc tag antibody. WCL, whole cell lysates.

FIG. 3E. Serine/threonine phosphatase activity for DLD1-PPP2R2B or vector control cells. Protein phosphatase activity of the immunoprecipitates of PPP2R2B-Myc was measured in triplicates from three independent experiments.

FIG. 3F. Immunoblot analysis of DLD1-PPP2R2B cells for Myc and p70S6K, treated PPP2R1A siRNA or a negative control siRNA, with or without Dox treatment.

FIG. 3G. Growth curve of HCT116 and DLD1 cells treated with Myc or p70S6K siRNA or a negative control siRNA for indicated days.

FIG. 4A. Proliferation of DLD1-PPP2R2B cells treated with 10 ng/ml Dox (Dox) or 10 nM rapamycin or both (R+D) for indicated days.

FIG. 4B. Dense foci formation on a monolayer of DLD1-PPP2R2B or DLD1 vector control cells treated with 10 nM rapamycin, with or without 10 ng/ml Dox treatment for 14 days.

FIG. 4C. Cell cycle G2/M arrest in DLD1-PPP2R2B or vector control cells treated with Dox or rapamycin or both for 48 h.

FIG. 4D. Xenograft tumor growth of DLD1-PPP2R2B cells in nude mice treated with Dox at 100 mg/kg, or rapamycin at 4 mg/kg or both, every other day as described in Experimental Procedures. Error bars represent SEM. *** $p<0.01$.

FIG. 4E. DLD1-PPP2R2B or DLD1 vector control cells were treated with 10 nM rapamycin in the presence or absence of Dox for 48 hr. The immunoblot analysis shows that rapamycin induces Myc phosphorylation, which is abrogated upon PPP2R2B expression.

FIG. 4F. Immunoblot analysis of indicated proteins in DLD1 cells treated with 10 nM rapamycin for the indicated times FIG. 4G. Immunoblot analysis of Myc in DLD1 cells treated with shRNAs targeting mTOR, raptor or rictor.

FIG. 5A. Immunoblot analysis of DLD1 cells for AKT and Myc. DLD1 cells were serum starved for 48 h and followed by treatment with 10 nM rapamycin for the indicated times.

FIG. 5B. Immunoblot analysis of DLD1 cells for AKT and Myc in response to a dual mTORC1 and P110α inhibitor PI-103 (0.5 µM) for the indicated times.

FIG. 5C. Immunoblot analysis of DLD1 cells for Myc, AKT, PI3K, or PDK1. Cells were transfected with siRNAs targeting the indicated genes or a negative control siRNA for 48 h, followed by 10 nM rapamycin treatment for 24 hr.

FIG. 5D. Immunoblot analysis of PDK1, Myc and AKT in DLD1 cells transfected with two different PDK1 siRNAs or a negative control siRNA and then treated with 10 nM rapamycin for 24 hr.

FIG. 5E. Immunoblot analysis of PDK1, Myc and AKT in SW480 cells infected with a retroviral PDK1 shRNA.

FIG. 5F. Immunoblot analysis of Myc, AKT and S6K in DLD1 cells treated with PDK1 inhibitor BX912 (2.5 µM), or PIK3CA inhibitor PIK90 (5 µM), rapamycin (10 nM) or indicated combinations for 48 hr.

FIG. 6A. Co-immunoprecipitation assay in 293T cells transfected with PPP2R2B-Myc, PDK1-HA, or both.

FIG. 6B. Co-immunoprecipitation assays in DLD1-PPP2R2B cells. Cells were treated with or without Dox for 24 h and PPP2R2B-Myc or PDK1 were pulled down and subjected to immunoblot analysis.

FIG. 6C. Immunoblotting analysis of the membrane fractions on PDK1 prepared from DLD1-PPP2R2B cells treated with or without Dox for 48 hr.

FIG. 6D. Immunofluorescence for PDK1-HA in DLD1-PPP2R2B with or without serum and Dox treatment.

FIG. 6E. Immunohistochemical (IHC) analysis of phosphorylated PDK1 in human colon and normal appendix tissue. Dark brown color represents positive signal of phospho-PDK1 at S241 and blue color represents the nuclear staining. Magnification for scanning IHC is 40×.

FIG. 7A. HCT116 cells were transfected with siRNAs targeting Myc, PDK1, AKT1 or PIK3CA for 48 h, and then treated with 100 nM rapamycin for 5 days. The graph bars show the rapamycin-induced growth inhibition relative to non-treated cells.

FIG. 7B. Rapamycin-induced growth inhibition in SW480 cells expressing PDK1 shRNA or a negative control shRNA.

FIG. 7C. G2/M phase arrest in SW480 and DLD1 cells induced by rapamycin (10 nM), BX912 (2.5 µM), PIK90 (5 µM), single or in combinations, assessed by PI staining and FACS analysis. Data are presented as mean±SD of the percentages of cells arrested in G2/M.

FIG. 7D. Cell viability of DLD1 and SW480 cells treated with BX912 (2.5 µM), rapamycin (10 nM), or both for indicated days.

FIG. 7E. Dense foci formation for 14 days on a monolayer of DLD1 and SW480 cells treated as FIG. 7D.

FIG. 7F. A model indicating a role of PPP2R2B-regulated PDK1-Myc pathway in modulating rapamycin response. Loss of PPP2R2B expression in CRC results in induction of PDK1-dependent Myc phosphorylation by rapamycin, conferring rapamycin resistance.

FIG. 10A. Anchorage-independent growth following retroviral packaged pMN-PPP2R2B in NIH/3T3-Ras cells is shown. Colony formation in soft agar was measured.

FIG. 10B. Immunoblotting studies of Myc and S6K proteins in NIH/3T3-Ras cells infected with PPP2R2B or control vector.

FIG. 11A. DLD1-PPP2R2B tet-on cells were treated with 1.0 μg/ml Dox for 8 h and cellular extracts were subjected to immunoprecipitation with S6K antibody and interaction of S6K with PPP2R2B and PP2A C subunit were studied by immunoblotting of the immunoprecipitates (IP).

FIG. 11B. DLD1-PPP2R2B tet-on cells were treated as FIG. 11A and cell lysate were immunoprecipitated with Myc-tagged antibody and the interaction of PPP2R2B with S6K and PP2A A subunit were studied by Western blotting of the immunoprecipitates.

FIG. 13A. Immunoblot analysis of Myc, AKT and p70S6K in HCT116 and DKO cells treated 10 nM rapamycin for the indicated times.

FIG. 13B. Rapamycin induced growth inhibition in HCT116 and DKO cells.

FIG. 13C. Immunoblot analysis of Myc, AKT, or p70S6K in a series of CRC cell lines treated with rapamycin for 48 hr.

FIG. 13D. Rapamycin-induced growth inhibition in CRC cell lines. Cell viability measured after 5 days treatment with 10 nM rapamycin. The graph bar represents the rapamycin-induced growth inhibition (%) compared to untreated cells.

FIG. 14A. ONCOMINE database showing the expression of PPP2R2B in renal (Boer et al., 2001), liver (Chen et al., 2002), lymphoma (Alizadeh et al., 2000) and ovarian cancer (Hendrix et al., 2006).

FIG. 14B. Taqman assay of PPP2R2B mRNA in indicated cancer cell lines and normal colon mucosa. ΔCT values were shown.

FIG. 14C. Immunblotting analysis of Myc and AKT phosphorylation in a panel of PPP2R2B-expressing cancer cell lines.

FIG. 14D. Rapamycin-induced growth inhibition in PPP2R2B-expressing cancer cell lines. Cell viability was measured after 5 days treatment with 10 nM rapamycin. The graph bar represents the rapamycin-induced growth inhibition (%) compared to untreated cells.

FIG. 15A. DLD1-PPP2R2B cells were treated with Dox for 48 h to induce PPP2R2B expression and cells were stained with anti-Myc (9E10) and DAPI to detect the localization of PPP2R2B-Myc in DLD1 cells. Scale bars=10 im.

FIG. 15B. DLD1 cells stained with anti-p-PDK1(S241) to detect the localization. Scale bars=10 im.

FIG. 15C. DLD1 cells treated with Rapamycin for 48 h and stained with anti-p-Myc (T58/S62).

FIG. 16A. Morphologies of SW480 cells under indicated treatments.

FIG. 16B. FACS analysis of DLD1 and SW480 cells treated with 2.5 μM BX912 or 2.5 μM PIKCA inhibitor PIK90 with or without rapamycin for 48 h. Cells were stained with PI and cell cycle was measured by FACS analysis. Percentages of cells arrested in G2/M were indicated.

(FIG. 20A). Immunoblot analysis of Myc and PLK1 in HEK-TERV cells transformed with PDK1, Myc or shPTEN (FIG. 20B). Immunoblot analysis of Myc and PLK1 in human mammary epithelial cells (HMEC) and prostate epithelial cells (RWPE).

DETAILED DESCRIPTION

Detection of mTOR Inhibitor Resistant Cancers

Figure 1A:
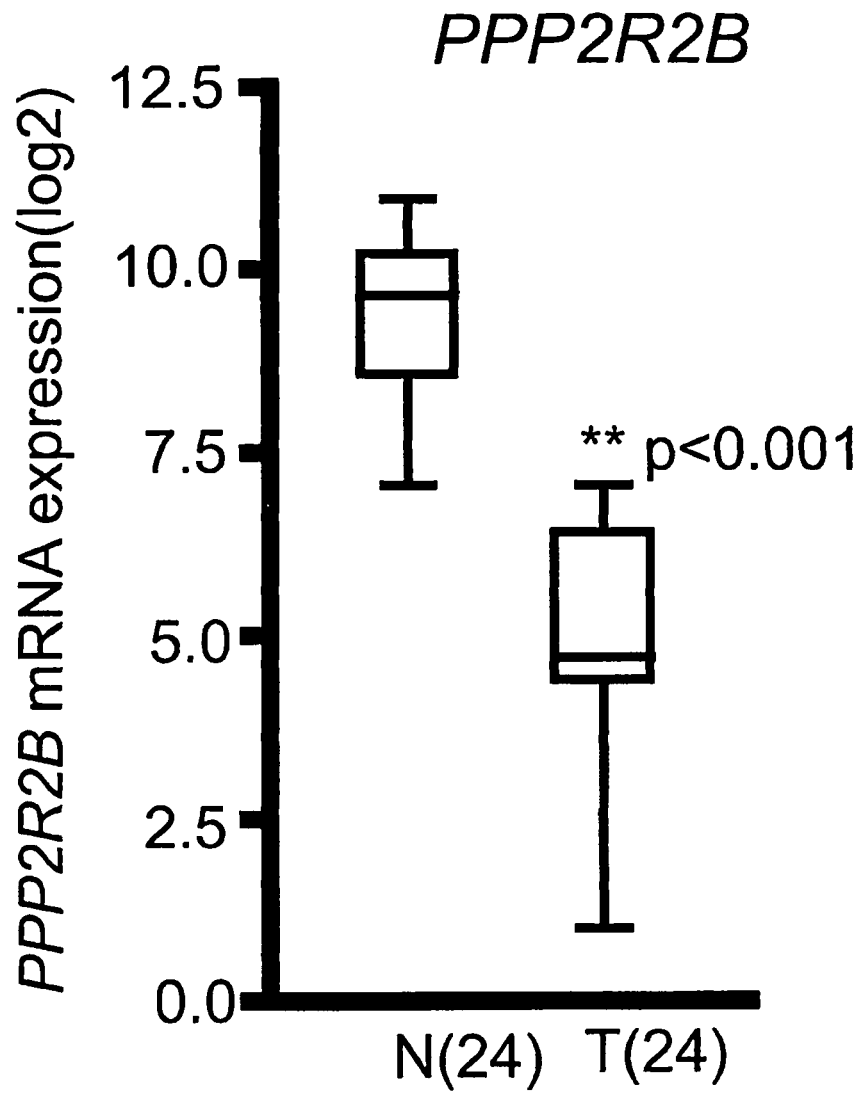
FIGS. 1A-1I. Loss of PPP2R2B expression by promoter DNA hypermethylation in CRC

As shown in Example 17, colorectal cancer (CRC) cells display epigenetic loss of PPP2R2B (GenBank Accession Number: NM_181678) activity and expression. PPP2R2B may therefore be used as a marker for colorectal cancer. Example 13 and FIG. 8 also show similar loss of PPP2R2B in other cancers such as bladder cancer, oesophageal cancer and brain cancer.

We therefore provide for a method of detecting a cancer cell or a patient suffering or likely to suffer from such a cancer, such as colorectal cancer, bladder cancer, oesophageal cancer or brain cancer, the method comprising detecting decreased expression and/or activity of PPP2R2B in or of a cell, or in or of a cell of a patient.

We demonstrate that such loss results in resistance to mTOR inhibitor treatment, such as treatment with rapamycin (or a derivative of rapamycin). We therefore provide for use of PPP2R2B as a tumour suppressor. We further provide for methods of detecting cancers which are resistant to treatment with mTOR inhibitor, including mTOR inhibitor resistant colorectal cancer, mTOR inhibitor resistant bladder cancer, mTOR inhibitor resistant oesophageal cancer and mTOR inhibitor resistant brain cancer, the methods comprising detecting reduced expression and/or activity of PPP2R2B, as described above. The mTOR inhibitor may comprise in particular rapamycin or a derivative thereof.

Up-regulation of expression of PPP2R2B activity in such cells, in combination with rapamycin treatment, inhibits growth of the cells. Cancers such as colorectal cancer, bladder cancer, oesophageal cancer and brain cancer, including mTOR inhibitor resistant forms, may therefore be treated by up-regulating the activity and/or expression of PPP2R2B, optionally in combination with treatment with mTOR inhibitors such as rapamycin or a derivative thereof, and we therefore provide for such methods in this document. Expression and/or activity of PPP2R2B may be achieved for example by use of demethylating agents such as cytidine analogues, including 5-aza-dC and Azacitidine (Issa J P, Kantarjian H. Azacitidine. Nat Rev Drug Discov 2005; May Suppl:S6-7).

Accordingly, we provide for a combination of (or composition comprising) a demethylating agent and an mTOR inhibitor, such as for use in treatment of a cancer including colorectal cancer, bladder cancer, oesophageal cancer and brain cancer (as well as mTOR inhibitor resistant forms, including rapamycin or rapamycin derivative resistant forms, of such cancers). The mTOR inhibitor may include rapamycin or a derivative thereof and the demethylating agent may include 5-aza-dC or Azacitidine.

We show in Example 19 that rapamycin induced Myc phosphorylation (leading to mTOR inhibitor resistance) is mediated by PDK1 kinase. Detection of PDK1 may therefore be used as a proxy for detection of PPP2R2B (as described above) for detecting cancers such as colorectal cancer, bladder cancer, oesophageal cancer and brain cancer, as well as mTOR inhibitor resistant forms thereof (e.g., rapamycin resistant or rapamycin derivative resistant forms of such cancers). We therefore provide for methods of detecting such cancers, by detection of PDK1 activity and/or expression, optionally together with detection of PPP2R2B activity and/or expression.

We further provide for use of PDK1 as a therapeutic target for cancers including colorectal cancer, bladder cancer, oesophageal cancer and brain cancer. Accordingly, we provide for the treatment of cancers such as colorectal cancer, bladder cancer, oesophageal cancer and brain cancer, as well as mTOR inhibitor resistant forms thereof (e.g., rapamycin resistant or rapamycin derivative resistant forms of such cancers) by down-regulation of PDK1 activity and/or expression. PDK1 activity and expression may be down-regulated by use a modulator of PDK1 activity and/or expression, such as a PDK1 antagonist or PDK1 inhibitor. PDK1 inhibitors and antagonists may be identified as described in further detail below, and may include for example PDK1 inhibitors such as BX912 (CAS Accession Number: 702674-56-4) and BX795 (CAS Accession Number: 702675-74-9). Other PDK1 inhibitors are known in the art and are described in, for example, R I Feldman et al. Novel Small Molecule Inhibitors of 3-Phosphoinositide-dependent Kinase-1. J. Biol. Chem., 2005, 280, 20, 19867-19874 and C Peifer, D R. Alessi, Small-Molecule Inhibitors of PDK1. ChemMedChem. 2008, 3 (10).

We therefore provide for the use of a PDK1 inhibitor or antagonist in the treatment of cancers such as colorectal cancer, bladder cancer, oesophageal cancer and brain cancer, as well as mTOR inhibitor resistant forms thereof (e.g., rapamycin resistant or rapamycin derivative resistant forms of such cancers). Treatment may further comprise administration of PDK1 inhibitors or antagonists in combination with an mTOR inhibitor such as rapamycin or a derivative thereof.

Accordingly, we provide for a combination of (or composition comprising) an inhibitor or antagonist of PDK1 and an mTOR inhibitor, such as for use in treatment of a cancer including colorectal cancer, bladder cancer, oesophageal cancer and brain cancer (as well as mTOR inhibitor resistant forms, including rapamycin or rapamycin derivative resistant forms, of such cancers). The mTOR inhibitor may include rapamycin or a derivative thereof and the PDK1 inhibitor or antagonist may comprise BX912 (CAS Accession Number: 702674-56-4) or BX795 (CAS Accession Number: 702675-74-9).

We further provide for the use of PDK1 and PLK1 for cancers such as cancer stem cells or Myc-driven tumors.

Treatment of Cancer

The methods and compositions described here suitably enable an improvement in a measurable criterion in an individual to whom the treatment is applied, compared to one who has not received the treatment.

For this purpose, a number of criteria may be designated, which reflect the progress of cancer or the well-being of the patient. Useful criteria may include tumour size, tumour dimension, largest dimension of tumour, tumour number, presence of tumour markers (such as alpha-feto protein), degree or number of metastates, etc.

Thus, as an example, a treated individual may show a decrease in tumour size or number as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%; 90%, 100% or more decrease in tumour size of a particular tumour, or decrease in tumour number, or both, compared to an individual who has not been treated.

In some embodiments, the effect of the treatment is suitably quantified using standard tests, such as the international criteria proposed by the Response Evaluation Criteria in Solid Tumours (RECIST) Committee, as described in detail in Therasse, P., S. G. Arbuck, et al. (2000). "New guidelines to evaluate the response to treatment in solid tumors. European Organization for Research and Treatment of Cancer, National Cancer Institute of the United States, National Cancer Institute of Canada." *J Natl Cancer Inst* 92(3): 205-16.

In other embodiments, the effect of the treatment may be quantified by following the administration and testing protocols described in the Clinical Trial (Examples E1 to E8). Thus, assessment of the effect of the treatment may be carried out using one or more of the protocols, preferably all, as set out in Example E8: Measurement of Effect. Where this is the case, the treatment may result in a Partial Response (PR) or a Complete Response (CR).

Although the controls described above have been described as individuals who have not received treatment, in some cases, a more suitable control may be the patient himself, prior to receiving treatment.

For the purposes of this document, the term "cancer" can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

mTOR

Where the term mTOR is used in this document, it should be taken to refer a polypeptide sequence having the accession number NM_004958.2, P42345 or NP_004949, more particularly NM_004958.2.

Preferably, mTOR refers to a human sequence. Thus, particular homologues encompassed by this term include human homologues, for example, accession numbers NM_004958.2, NP_004949, Hs.509145. However, the term also covers alternative peptides homologous to mTOR, such as polypeptides derived from other species, including other mammalian species. For example, mouse homologues of mTOR having accession number NM_020009.1, NP_064393, Mm 0.21158, Q9JLN9, AAF73196 and AF152838 are included. Bovine and rat homologues of mTOR are also known (accession numbers NM_174319 and NM_019906 respectively).

mTOR is also known as FKBP12-Rapamycin Complex-Associated Protein 1, FRAP1, FK506-Binding Protein 12-Rapamycin Complex-Associated Protein 1, FRAP, FRAP2, Mammalian Target of Rapamycin and RAFT1.

Preferably, mTOR includes fragments, homologues, variants and derivatives of such a nucleotide sequence. The terms "variant", "homologue", "derivative" or "fragment" as used here include any substitution of, variation of, modification of, replacement of, deletion of or addition of one (or more) nucleic acids from or to the sequence of a mTOR nucleotide sequence. Unless the context admits otherwise, references to "mTOR" include references to such variants, homologues, derivatives and fragments of mTOR. These are described in more detail below.

Preferably, the resultant nucleotide sequence encodes a polypeptide having mTOR activity, preferably having at least the same activity of the human mTOR referred to above.

Preferably, the term "homologue" is intended to cover identity with respect to structure and/or function such that the resultant nucleotide sequence encodes a polypeptide which has mTOR activity. With respect to sequence identity (i.e. similarity), preferably there is at least 70%, more preferably at least 75%, more preferably at least 85%, more preferably at least 90% sequence identity. More preferably there is at least 95%, more preferably at least 98%, sequence identity. These terms also encompass allelic variations of the sequences.

The following description of mTOR, referred to as FRAP, is provided from the Online Mendelian Inheritance in Man website (http://www.ncbi.nlm.nih.gov/entrez/dispomim.cgi?id=601231)

FKBP12-rapamycin associated protein (FRAP) is one of a family of proteins involved in cell cycle progression, DNA recombination, and DNA damage detection. In rat, it is a 245-kD protein (symbolized RAFT1) with significant homology to the *Saccharomyces cerevisiae* protein TOR1 and has been shown to associate with the immunophilin FKBP12 (186945) in a rapamycin-dependent fashion (Sabatini et al., 1994). Brown et al. (1994) noted that the FKBP12-rapamycin complex was known to inhibit progression through the G1 cell cycle stage by interfering with mitogenic signaling pathways involved in G1 progression in several cell types, as well as in yeast. The authors stated that the binding of FRAP to FKBP12-rapamycin correlated with the ability of these ligands to inhibit cell cycle progression.

Rapamycin is an efficacious anticancer agent against solid tumors. In a hypoxic environment, the increase in mass of solid tumors is dependent on the recruitment of mitogens and nutrients. When nutrient concentrations change, particularly those of essential amino acids, the mammalian target of rapamycin (mTOR/FRAP) functions in regulatory pathways that control ribosome biogenesis and cell growth. In bacteria, ribosome biogenesis is independently regulated by amino acids and ATP. Dennis et al. (2001) demonstrated that the human mTOR pathway is influenced by the intracellular concentration of ATP, independent of the abundance of amino acids, and that mTOR/FRAP itself is an ATP sensor.

Castedo et al. (2001) delineated the apoptotic pathway resulting from human immunodeficiency virus (HIV)-1 envelope glycoprotein (Env)-induced syncytia formation in vitro and in vivo. Immunohistochemical analysis demonstrated the presence of phosphorylated ser15 of p53 (191170) as well as the preapoptotic marker tissue transglutaminase (TGM2; 190196) in syncytium in the apical light zone (T-cell area) of lymph nodes, as well as in peripheral blood mononuclear cells, from HIV-1-positive but not HIV-1-negative donors. The presence of these markers correlated with viral load (HIV-1 RNA levels). Quantitative immunoblot analysis showed that phosphorylation of ser15 of p53 in response to HIV-1 Env is mediated by FRAP and not by other phosphatidylinositol kinase-related kinases, and it is accompanied by downregulation of protein phosphatase 2A (see 176915). The phosphorylation is significantly inhibited by rapamycin. Immunofluorescence microscopy indicated that FRAP is enriched in syncytial nuclei and that the nuclear accumulation precedes the phosphorylation of ser15 of p53. Castedo et al. (2001) concluded that HIV-1 Env-induced syncytium formation leads to apoptosis via a pathway that involves phosphorylation of ser15 of p53 by FRAP, followed by activation of BAX (600040), mitochondrial membrane permeabilization, release of cytochrome C, and caspase activation.

Fang et al. (2001) identified phosphatidic acid as a critical component of mTOR signaling. In their study, mitogenic stimulation of mammalian cells led to a phospholipase D-dependent accumulation of cellular phosphatidic acid, which was required for activation of mTOR downstream effectors. Phosphatidic acid directly interacted with the domain in mTOR that is targeted by rapamycin, and this interaction was positively correlated with mTOR's ability to activate downstream effectors. The involvement of phosphatidic acid in mTOR signaling reveals an important function of this lipid in signal transduction and protein synthesis, as well as a direct link between mTOR and mitogens. Fang et al. (2001) concluded that their study suggested a potential mechanism for the in vivo actions of the immunosuppressant rapamycin.

Kim et al. (2002) and Hara et al. (2002) reported that mTOR binds with RAPTOR (607130), an evolutionarily conserved protein with at least 2 roles in the mTOR pathway. Kim et al. (2002) showed that RAPTOR has a positive role in nutrient-stimulated signaling to the downstream effector S6K1 (601684), maintenance of cell size, and mTOR protein expression. The association of RAPTOR with mTOR also negatively regulates mTOR kinase activity. Conditions that repress the pathway, such as nutrient deprivation and mitochondrial uncoupling, stabilize the mTOR-RAPTOR association and inhibit mTOR kinase activity. Kim et al. (2002) proposed that RAPTOR is a component of the mTOR pathway that, through its association with mTOR, regulates cell size in response to nutrient levels.

Hara et al. (2002) showed that the binding of RAPTOR to mTOR is necessary for the mTOR-catalyzed phosphorylation of 4EBP1 (602223) in vitro and that it strongly enhances the mTOR kinase activity toward p70-alpha (S6K1). Rapamycin or amino acid withdrawal increased, whereas insulin strongly inhibited, the recovery of 4EBP1 and RAPTOR on 7-methyl-GTP sepharose. Partial inhibition of RAPTOR expression by RNA interference reduced mTOR-catalyzed 4EBP1 phosphorylation in vitro. RNA interference of C. elegans Raptor yielded an array of phenotypes that closely resembled those produced by inactivation of CE-Tor. Thus, the authors concluded that RAPTOR is an essential scaffold for the mTOR-catalyzed phosphorylation of 4EBP1 and mediates TOR action in vivo.

Vellai et al. (2003) demonstrated that TOR deficiency in C. elegans more than doubles its natural life span. The absence of Let363/TOR activity caused developmental arrest at the L3 larval stage. At 25.5 degrees C., the mean life span of Let363 mutants was 25 days compared with a life span of 10 days in wildtype worms.

Huntington disease (HD; 143100) is an inherited neurodegenerative disorder caused by a polyglutamine tract expansion in which expanded polyglutamine proteins accumulate abnormally in intracellular aggregates. Ravikumar et al. (2004) showed that mammalian target of rapamycin (mTOR) is sequestered in polyglutamine aggregates in cell models, transgenic mice, and human brains. Sequestration of mTOR impairs its kinase activity and induces autophagy, a key clearance pathway for mutant huntingtin fragments. This protects against polyglutamine toxicity, as the specific mTOR inhibitor rapamycin attenuates huntingtin accumulation and cell death in cell models of HD, and inhibition of autophagy has converse effects. Furthermore, rapamycin protects against neurodegeneration in a fly model of HD, and the rapamycin analog CCI-779 improved performance on 4 different behavioral tasks and decreased aggregate formation in a mouse model of HD. The data provided proof of principle for the potential of inducing autophagy to treat HD.

Moore et al. (1996) assigned the FRAP gene to 1p36 by fluorescence in situ hybridization (FISH). Lench et al. (1997) mapped the FRAP gene to 1p36.2 by FISH following radiation-hybrid mapping to that general region. Chromosome 1p36.2 is the region most consistently deleted in neuroblastomas. Given the role of PIK-related kinase proteins in DNA repair, recombination, and cell cycle checkpoints, the authors suggested that the possible role of FRAP in solid tumors with deletions at 1p36 should be investigated. Onyango et al. (1998) established the order of genes in the 1p36 region, telomere to centromere, as CDC2L1 (176873)-PTPRX2 (604008)-ENO1 (172430)-PGD (172200)-XBX1 (604007)-FRAP2 (FRAP1)-CD30 (153243).

mTOR is described in detail in Beugnet, et al. J. Biol. Chem. 278 (42), 40717-40722 (2003); Kristof, et al., J. Biol. Chem. 278 (36), 33637-33644 (2003); Chen, Y., et al., Oncogene 22 (25), 3937-3942 (2003); Garami, et al., Mol. Cell. 11 (6), 1457-1466 (2003); Nojima, et al., J. Biol. Chem. 278 (18), 15461-15464 (2003); Kimura, et al., Genes Cells 8 (1), 65-79 (2003); McMahon, et al., Mol. Cell. Biol. 22 (21), 7428-7438 (2002); Tee, et al., Proc. Natl. Acad. Sci. U.S.A. 99 (21), 13571-13576 (2002); Hudson, et al., Mol. Cell. Biol. 22 (20), 7004-7014 (2002); Choi, et al., EMBO Rep. 3 (10), 988-994 (2002); Inoki, et al., Nat. Cell Biol. 4 (9), 648-657 (2002); Zhang, et al., J. Biol. Chem. 277 (31), 28127-28134 (2002); Castedo, et al., EMBO J. 21 (15), 4070-4080 (2002); Hara, et al., Cell 110 (2), 177-189 (2002); Kim, et al., Cell 110 (2), 163-175 (2002); Fingar, et al., Genes Dev. 16(12), 1472-1487 (2002); Reynolds, et al., J. Biol. Chem. 277 (20), 17657-17662 (2002); Fang, et al., Science 294 (5548), 1942-1945 (2001); Dennis, et al., Science 294 (5544), 1102-1105 (2001); Onyango, et al., Genomics 50 (2), 187-198 (1998); Lench, et al., Hum. Genet. 99 (4), 547-549 (1997); Choi, et al., Science 273 (5272), 239-242 (1996); Moore, et al., Genomics 33 (2), 331-332 (1996); Chen, et al., Proc. Natl. Acad. Sci. U.S.A. 92 (11), 4947-4951 (1995); Chiu et al., Proc. Natl. Acad. Sci. U.S.A. 91 (26), 12574-12578 (1994); Brown, et al., Nature 369 (6483), 756-758 (1994).

Inhibitor of mTOR Activity

The methods and compositions described here rely, in some embodiments, on blocking, reducing, or decreasing the activity of mTOR protein. Such inhibition of mTOR activity may be used in conjunction to treat cancer or prevent cell or tissue growth or proliferation according to the methods and compositions described here.

While any means of doing so may be used, in general, the methods and compositions described here employ modulators of mTOR activity or expression. Agents which are capable of decreasing the activity of mTOR protein are referred to as inhibitors or antagonists of that activity. For the purpose of this document, the terms "inhibitor" and "antagonist" may be regarded as synonymous, where the context requires.

In preferred embodiments, antagonists of mTOR activity have the ability to decrease a relevant activity of mTOR, for example, kinase activity, by 10%, 20%, 30%, 40%, 50%, 60%, 70%, 80%, 90%, 95% or more. Preferably, mTOR activity is assayed as described below in the section "Assays for mTOR Activity".

The term "antagonist", as used in the art, is generally taken to refer to a compound which binds to an enzyme and inhibits the activity of the enzyme. The term as used here, however, is intended to refer broadly to any agent which inhibits the activity of a molecule, not necessarily by binding to it. Accordingly, it includes agents which affect the expression of an mTOR protein, or the biosynthesis of a regulatory molecule, or the expression of modulators of the activity of mTOR. The specific activity which is inhibited may be any activity which is exhibited by, or characteristic of, the enzyme or molecule, for example, any activity of mTOR as the case may be, for example, a kinase activity. The kinase activity may comprise the ability to phosphorylate one or either of S6K1 and/or 4E-BP1.

The antagonist may bind to and compete for one or more sites on the relevant molecule preferably, the catalytic site of the enzyme. Preferably, such binding blocks the interaction between the molecule and another entity (for example, the interaction between a enzyme and its substrate). However, the antagonist need not necessarily bind directly to a catalytic site, and may bind for example to an adjacent site, another protein (for example, a protein which is complexed with the enzyme) or other entity on or in the cell, so long as its binding reduces the activity of the enzyme or molecule.

Where antagonists of a enzyme such as mTOR are concerned, an antagonist may include a substrate of the enzyme, or a fragment of this which is capable of binding to the enzyme. In addition, whole or fragments of a substrate generated natively or by peptide synthesis may be used to compete with the substrate for binding sites on the enzyme. Alternatively, or in addition, an immunoglobulin (for example, a monoclonal or polyclonal antibody) capable of binding to the enzyme may be used. The antagonist may also include a peptide or other small molecule which is capable of interfering with the binding interaction. Other examples of antagonists are set forth in greater detail below, and will also be apparent to the skilled person.

Non-functional homologues of a mTOR may also be tested for inhibition of mTOR activity as they may compete with the wild type protein for binding to other components of the cell machinery whilst being incapable of the normal functions of the protein. Alternatively, they may block the function of the protein bound to the cell machinery. Such non-functional homologues may include naturally occurring mutants and modified sequences or fragments thereof.

Alternatively, instead of preventing the association of the components directly, the substance may suppress the biologically available amount of a mTOR. This may be by inhibiting expression of the component, for example at the level of transcription, transcript stability, translation or post-translational stability. An example of such a substance would be antisense RNA or double-stranded interfering RNA sequences which suppresses the amount of mRNA biosynthesis.

Blocking the activity of an inhibitor of the mTOR protein may therefore also be achieved by reducing the level of expression of the protein or an inhibitor in the cell. For example, the cell may be treated with antisense compounds, for example oligonucleotides having sequences specific to the mTOR mRNA. The level of expression of pathogenic forms of adhesion proteins may also be regulated this way.

In general, agonists, antagonists of mTOR may comprise agents such as an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex.

The terms "modulator", "antagonist" and "agent" are also intended to include, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, a signalling molecule or other protein; a nucleic acid, as defined below, including, but not limited to, an, oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. Small molecules, including inorganic and organic chemicals, which bind to and occupy the active site of the polypeptide thereby making the catalytic site inaccessible to substrate such that normal biological activity is prevented, are also included. Examples of small molecules include but are not limited to small peptides or peptide-like molecules.

In a particular embodiment, the technique of RNA interference (RNAi) may be used to abolish or knock out or reduce gene activity, for example, mTOR activity. The overall strategy is to prepare double stranded RNA (dsRNA) specific to each gene of interest and to transfect this into a cell of interest to inhibit the expression of the particular gene.

The following protocol may be used: a sample of PCR product is analysed by horizontal gel electrophoresis and the DNA purified using a Qiagen QiaQuick PCR purification kit. 1 μg of DNA is used as the template in the preparation of gene specific single stranded RNA using the Ambion T7 Megascript kit. Single stranded RNA is produced from both strands of the template and is purified and immediately annealed by heating to 90 degrees C. for 15 mins followed by gradual cooling to room temperature overnight. A sample of the dsRNA is analysed by horizontal gel electrophoresis, and introduced into the relevant cell by conventional means.

Antagonists of mTOR Activity

Any agent which is capable of reducing mTOR activity or expression, as described above, may be used as an antagonist of mTOR for the purposes of reducing its activity.

Butanol

1-Butanol is an inhibitor of mTOR activity, as described in Kam and Exton, FASEB J. 2004 February; 18(2):311-9 and Fang et al., Science 294:1942-1945. Butanol may therefore be used in the methods and compositions described here as an agent capable of reducing mTOR activity.

Anti-Peptide mTOR Antibodies

Anti-peptide antibodies may be produced against mTOR peptide sequences. The sequences chosen may be based on the mouse sequences as follow from the following mTOR reference sequence:

```
 1 mlgtgpavat asaatssnvs vlqqfasglk srneetraka akelqhyvtm elremsqees
61 trfydqlnhh ifelvsssda nerkggilai asligveggn strigrfany lrnllpssdp
```

-continued

```
 121  vvmemaskai grlamagdtf taeyvefevk ralewlgadr negrrhaavl vlrelaisvp
 181  tfffqqvqpf fdnifvavwd pkgairegav aalraclilt tqrepkemqk pqwyrhtfee
 241  aekgfdetla kekgmnrddr ihgallilne lvrissmege rlreemeeit qqqlvhdkyc
 301  kdlmgfgtkp rhitpftsfq avqpqqpnal vgllgysspq glmgfgtsps pakstivesr
 361  ccrdlmeekf dqvcqwvlkc rssknsliqm tilnllprla afrpsaftdt qylqdtmnhv
 421  lscvkkeker taafgalgll svavrsefkv ylprvldiir aalppkdfah krqktvqvda
 481  tvftcismla ramgpgiqqd ikellepmla vglspaltav lydlsrqipq lkkdiqdgll
 541  kmlslvlmhk plrhpgmpkg lahqlaspgl ttlpeasdva sitlalrtlg sfefeghslt
 601  qfvrhcadhf lnsehkeirm eaartcscll tpsihlisgh ahvvsqtavq vvadvlskll
 661  vvgitdpdpd irycvlasld erfdahlaqa enlqalfval ndqvfeirel aictvgrlss
 721  mnpafvmpfl rkmliqilte lehsgigrik eqsarmlghl vsnaprlirp ymepilkali
 781  lklkdpdpdp npgvinnvla tigelaqvsg lemrkwvdel fiiimdmlqd ssllakrqva
 841  lwtlgqlvas tgyvvepyrk yptllevlln flkteqnqgt rreairvlgl lgaldpykhk
 901  vnigmidqsr dasavslses kssqdssdys tsemlvnmgn lpldefypav smvalmrifr
 961  dqslshhhtm vvqaitfifk slglkcvqfl pqvmptflnv irvcdgaire flfqqlgmlv
1021  sfvkshirpy mdeivtlmre fwvmntsiqs tiillieqiv valggefkly lpqliphmlr
1081  vfmhdnsqgr ivsikllaai qlfganlddy lhlllppivk lfdapevplp srkaaletvd
1141  rltesldftd yasriihpiv rtldqspelr stamdtlssl vfqlgkkyqi fipmvnkvlv
1201  rhrinhqryd vlicrivkgy tladeeedpl iyqhrmlrss qgdalasgpv etgpmkklhv
1261  stinlqkawg aarrvskddw lewlrrlsle llkdsssps1 rscwalaqay npmardlfna
1321  afvscwseln edqqdelirs ielaltsqdi aevtqtlllnl aefmehsdkg plplrddngi
1381  vllgeraakc rayakalhyk elefqkgptp aileslisin nklqqpeaas gvleyamkhf
1441  geleiqatwy eklhewedal vaydkkmdtn kedpelmlgr mrclealgew gqlhqqccek
1501  wtivndetqa kmarmaaaaa wglgqwdsme eytcmiprdt hdgafyravl alhqdlfsla
1561  qqcidkardl ldaeltamag esysraygam vschmlsele eviqyklvpe rreiirqiww
1621  erlqgcqriv edwqkilmvr slvvsphedm rtwlkyaslc gksgrlalah ktlvlllgvd
1681  psrqldhplp tahpqvtyay mknmwksark idafqhmqhf vqtMqqqaqh aiatedqqhk
1741  qelhklmarc flklgewqln lqginestip kvlqyysaat ehdrswykaw hawavmnfea
1801  vlhykhqnqa rdekkklrha sganitnatt aattaasaaa atstegsnse seaesnensp
1861  tpsplqkkvt edlsktllly tvpavqgffr sislsrgnnl qdtlrvltlw fdyghwpdvn
1921  ealvegvkai qidtwlqvip qliaridtpr plvgrlihql ltdigryhpq aliypltvas
1981  kstttarhna ankilknmce hsntivqqam mvseelirva ilwhemwheg leeasrlyfg
2041  ernvkgmfev leplhammer gpqtlketsf nqaygrdlme aqewcrkymk sgnvkdltqa
2101  wdlyyhvfrr iskqlpqlts lelqyvspkl lmcrdlelav pgtydpnqpi iriqsiapsl
2161  qvitskqrpr kltlmgsngh efvfllkghe dlrqdervmq lfglvntlla ndptslrknl
2221  siqryavipl stnsgligwv phcdtlhali rdyrekkkil lniehrimlr mapdydhltl
2281  mqkvevfeha vnntagddla kllwlkspss evwfdrrtny trslavmsmv gyilglgdrh
2341  psnlmldrls gkilhidfgd cfevamtrek fpekipfrlt rmltnamevt gldgnyrttc
2401  htvmevlreh kdsvmavlea fvydpllnwr lmdtntkgnk rsrtrtdsys agqsveildg
2461  velgepahkk agttvpesih sfigdglvkp ealnkkaiqi inrvrdkltg rdfshddtld
2521  vptqvellik qatshenlcq cyigwcpfw
```

Thus, preferred anti-peptide antibodies may be raised from any one or more of the following sequences: amino acids 22-139; amino acids 647-907; amino acids 937-1140; amino acids 1382-1982; amino acids 2019-2112; or amino acids 2181-2549.

Corresponding sequences from human mTOR may be chosen for use in eliciting anti-peptide antibodies from immunised animals. Antibodies may be produced by injection into rabbits, and other conventional means, as described in for example, Harlow and Lane (supra).

Antibodies are checked by Elisa assay and by Western blotting, and used for immunostaining as described in the Examples.

Rapamycin

In some embodiments, an agent capable of reducing mTOR activity comprises rapamycin. As the term is used in this document, "rapamycin" includes the specific compound rapamycin (also known as Sirolimus, $C_{51}H_{79}NO_{13}$, which is described below) as well as any of its derivatives. Such derivatives are described in detail and include rapamycin prodrugs, rapamycin dialdehydes, structural analogues of rapamycin (rapalogs), etc.

Rapamycin, including its derivatives, etc, is therefore provided as a specific antagonist of mTOR activity.

Rapamycin and its derivatives may be employed at concentrations over 1 nM, for example, 10 nM, 20 nM, 30 nM, 40 nM, 50 nM, 100 nM, 500 nM, 10 μm, 100 μm, or more. In some embodiments, rapamycin and its derivatives are used at about 50 nM. Rapamycin and its derivatives may be administered to human individuals at dosages of for example between about 1 mg/day and 10 mg/day.

Rapamycin (Sirolimus)

Rapamycin ($C_{51}H_{79}NO_{13}$, molecular mass 914.172 g/mol.) is an antifungal antibiotic which is extractable from a streptomycete, e.g., *Streptomyces hygroscopicus*.

Rapamycin has an IUPAC name of (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone.

Rapamycin is identified by its CAS number 53123-88-9, ATC code L04AA10, PubChem 6436030, DrugBank APRD00178. The structural formula of rapamycin is shown below:

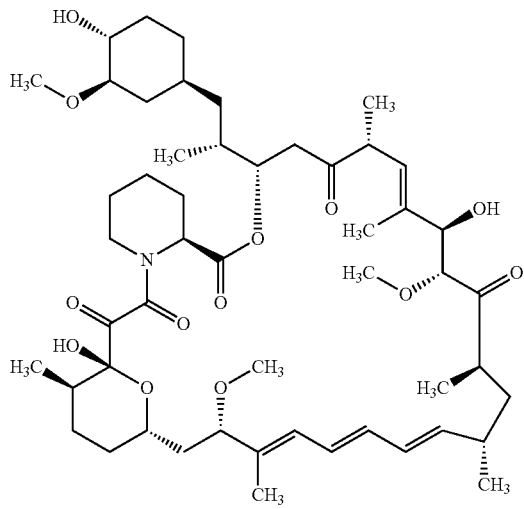 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

Rapamycin is also known as Sirolimus.

Methods for the preparation of rapamycin are disclosed in Sehgal et al., U.S. Pat. Nos. 3,929,992, and 3,993,749. In addition, monoacyl and diacyl derivatives of rapamycin and methods for their preparation are disclosed by Rakhit, U.S. Pat. No. 4,316,885. Furthermore, Stella et al., U.S. Pat. No. 4,650,803 disclose water soluble prodrugs of rapamycin, i.e., rapamycin derivatives including the following rapamycin prodrugs: glycinate prodrugs, propionate prodrugs and the pyrrolidino butyrate prodrugs.

The methods and compositions described here include the use of natural and synthetic rapamycin, genetically engineered rapamycin and all derivatives and prodrugs of rapamycin, such as described in the aforementioned U.S. Pat. Nos. 3,929,992; 3,993,749; 4,316,885; and 4,650,803, the contents of which are hereby incorporated by reference.

Rapamycin is a 31-membered macrolide lactone, $C_{51}H_{79}NO_{13}$, with a molecular mass of 913.6 Da. In solution, sirolimus forms two conformational trans-, cis-isomers with a ratio of 4:1 (chloroform) due to hindered rotation around the pipecolic acid amide bond. It is sparingly soluble in water, aliphatic hydrocarbons and diethyl ether, whereas it is soluble in alcohols, halogenated hydrocarbons and dimethyl sulfoxide. Rapamycin is unstable in solution and degrades in plasma and low-, and neutral-pH buffers at 37 degrees C. with half-life of <10 h. the structures of the degradation products have recently been characterized. Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S, N. Sehgal et al., J. Antibiot. 28, 727 (1975); H. A. Baker et al., J. Antibiot. 31, 539 (1978); U.S. Pat. No. 3,929,992; and U.S. Pat. No. 3,993, 749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Caine et al., Lancet 1183 (1978)]. Although it shares structural homology with the immunosuppressant tacrolimus and binds to the same intracellular binding protein in lymphocytes, rapamycin inhibits S6p70-kinase and therefore has a mechanism of immunosuppressive action distinct from that of tacrolimus. Rapamycin was found to prolong graft survival of different transplants in several species alone or in combination with other immunosupressants. In animal models its spectrum of toxic effects is different from that of cyclosporin or FK-506, comprising impairment of glucose homeostasis, stomach, ulceration; weight loss and thrombocytopenia, although no nephrotoxicity has been detected.

Rapamycin Derivatives

Rapamycin derivatives include rapamycin prodrugs, rapamycin dialdehydes, structural analogues of rapamycin (rapalogs), etc, and are described in detail below.

Specific derivatives of rapamycin which may be used in the methods and compositions described here include RAD001 (Everolimus) and CCI-779 (Wyeth).

RAD001 (Everolimus)

RAD001 ($C_{53}H_{83}NO_{14}$, molecular mass 958.224 g/mol) is a derivative of rapamycin. RAD001 is identified by its CAS number 159351-69-6, ATC code L04AA18 and PubChem 6442177. The structural formula of RAD001 is shown below:

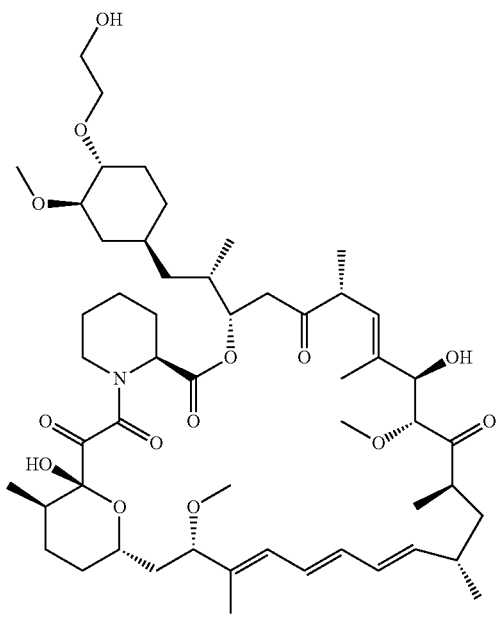 [SMILES: CO[C@H]1C[C@@H]2CC[C@@H](C)[C@@](O)(O2)C(=O)C(=O)N2CCCC[C@H]2C(=O)O[C@H]([C@@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

RAD001 is also known as Everolimus and is manufactured by Novartis AG. It is currently used as an immunosuppressant to prevent rejection of organ transplants.

RAD001 is described in detail in O'Reilly T M, Wood J M, Littlewood-Evans A, et al. Differential anti-vascular effects of mTOR or VEGFR pathway inhibition: a rational basis for combining RAD001 and PTK787/ZK222584. Presented at: 96th Annual Meeting of the American Association for Cancer Research. Anaheim, Calif.; Apr. 16-20, 2005. Abstract 3038.

RAD001 is also described in 105. Van Oosterom A T, Dumez H, Desai J, et al. Combination signal transduction inhibition: a phase I/II trial of the oral mTOR-inhibitor everolimus (E, RAD001) and imatinib mesylate (IM) in patients (pts) with gastrointestinal stromal tumor (GIST) refractory to IM [abstract]. Proc Am Soc Clin Oncol. 2004; 23:195. Abstract 3002.

CCI 779 (Temsirolimus)

CCI 779 (cell cycle inhibitor-779, $C_{56}H_{87}NO_{16}$, molecular weight 1030.3) is an ester analogue of Rapamycin.

CCI 779 is also known as rapamcyin-28-N,N-dimethylglycinate methanesulfonate salt, rapamycin, 42-[3-hydroxy-2-(hydroxymethyl)-2-methylpropanoate], (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]oxaazacyclohentriacontine-1,5,11,28,29(4H,6H,31H)-pentone 4'-[2,2-bis(hydroxymethyl)propionate] and rapamycin 42-[2,2-bis(hydroxymethyl)propionate].

CCI 779 is identified by its CAS registry number 162635-04-3. The structural formula of CCI 779 is shown below:

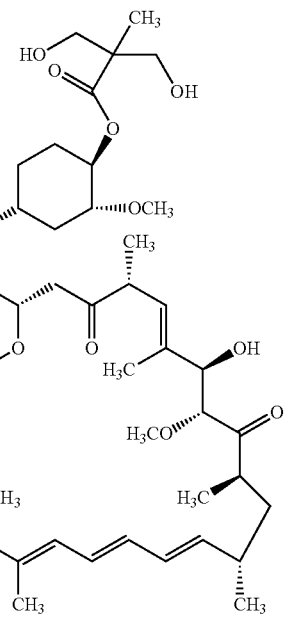

CCI 779 is also known as Temsirolimus and is manufactured by Wyeth. Temsirolimus binds to the cytosolic protein, FKBP, which subsequently inhibits mTOR (mammalian target of rapamycin).

In animal models of human cancers, temsirolimus has been found to inhibit the growth of a diverse range of cancer types even when an intermittent dosing schedule was used. The compound also appears to have potential for the blockade of inflammatory responses associated with autoimmune and rheumatic diseases by inhibiting T-cell proliferation.

CCI 779 is a water soluble ester (prodrug) of rapamycin that releases rapamycin in vivo. It is believed to be more tolerable than rapamycin when used clinically and is currently being studied for use in oncology patients in Phase II and III trials (including brain tumors).

CCI 779 is described in detail in Nat. Genet. 2004; 36:585-95 and J Clin Oncol. 2004; 22:2336-47. Reference should also be made to K Yu, L Toral-Barza, C Discafani, W G Zhang, J Skotnicki, P Frost, and J J Gibbons (2001). mTOR, a novel target in breast cancer: the effect of CCI-779, an mTOR inhibitor, in preclinical models of breast cancer. Endocrine-Related Cancer 8 (3) 249-258 and Josep Maria Peralba, Linda deGraffenried, William Friedrichs, Letitia Fulcher, Viktor Grunwald, Geoffrey Weiss and Manuel Hidalgo (2003. Pharmacodynamic Evaluation of CCI-779, an Inhibitor of mTOR, in Cancer Patients. Clinical Cancer Research Vol. 9, 2887-2892.

Rapamycin Prodrugs

The mTOR inhibitor, particularly rapamycin, may be provided in the form of a prodrug. A specific example of a rapamycin prodrug is CCI 779, described above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375 382,615th Meeting Belfast (1986) and Stella et al., "Prodrugs: A Chemical Approach to Targeted Drug Delivery," Directed Drug Delivery, Borchardt et al., (ed.), pp. 247 267, Humana Press (1985). The prodrugs described here include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of drugs that can be derivatized into a prodrug form for use in the methods and compositions described here include, but are not limited to, those chemotherapeutic agents described above.

Rapamycin Dialdehydes

Rapamycin prodrugs such as rapamycin dialdehydes described in U.S. Pat. No. 6,680,330 (Zhu, et al) may be employed in the methods and compositions described here.

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. Carboxylic acid esters (PCT application No. WO 92/05179), carbamates (U.S. Pat. No. 5,118,678), amide esters (U.S. Pat. No. 5,118,678), (U.S. Pat. No. 5,118,678) fluorinated esters (U.S. Pat. No. 5,100,883), acetals (U.S. Pat. No. 5,151,413), silyl ethers (U.S. Pat. No. 5,120,842), bicyclic derivatives (U.S. Pat. No. 5,120,725), rapamycin dimers (U.S. Pat. No. 5,120,727) and O-aryl, O-alkyl, O-alkyenyl and O-alkynyl derivatives (U.S. Pat. No. 5,258,389) have been described.

Rapamycin is metabolized by cytochrome P-450 3A to at least six metabolites. During incubation with human liver and small intestinal microsomes, sirolimus was hydroxylated and demethylated and the structure of 39-O-demethyl sirolimus was identified. In bile of sirolimus-treated rats >16 hydroxylated and demethylated metabolites were detected.

In rapamycin, demethylation of methoxy group at C-7 Carbon will lead to the change in the conformation of the Rapamycin due to the interaction of the released C-7 hydroxyl group with the neighbouring pyran ring system which is in equilibrium with the open form of the ring system. The C-7 hydroxyl group will also interact with the triene system and possibly alter the immunosupressive activity of rapamycin. This accounts for the degradation of rapamycin molecule and its altered activity.

these may be employed in the methods and compositions described here.

For example, the extensive literature on analogs, homologs, derivatives and other compounds related structurally to rapamycin ("rapalogs") include among others variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. In nearly all cases, potent immunosuppressive activity is reported to accompany antifungal activity of the rapalogs. Additional historical information is presented in the background sections of U.S. Pat. Nos. 5,525,610; 5,310,903 and 5,362,718.

Rapalogs

"Rapalogs" as that term is used herein denotes a class of compounds comprising the various analogs, homologs and derivatives of rapamycin and other compounds related structurally to rapamycin. "Rapalogs" include compounds other than rapamycin (or those rapamycin derivatives modified in comparison to rapamycin only with respect to saturation of one or more of the carbon-carbon double bonds at the 1, 2, 3, 4 or 5, 6 positions) which comprise the substructure shown in Formula I, bearing any number of a variety of substituents, and optionally unsaturated at one or more carbon-carbon bonds unless specified to the contrary herein.

Rapalogs include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and elimination, derivatization or replacement of one or more substituents of the cyclohexyl ring or replacement of the cyclohexyl ring with a substituted or unsubstituted cyclopentyl ring. Rapalogs, as that term is used herein, do not include rapamycin itself, and preferably do not contain an oxygen bridge between C1 and C30. Illustrative examples of rapalogs are disclosed in the documents listed in Table I. Examples of rapalogs modified at C7 are shown in Table II.

TABLE I

| | | | | |
|---|---|---|---|---|
| WO9710502 | WO9418207 | WO9304680 | U.S. Pat. No. 5,527,907 | U.S. Pat. No. 5,225,403 |
| WO9641807 | WO9410843 | WO9214737 | U.S. Pat. No. 5,484,799 | U.S. Pat. No. 5,221,625 |
| WO9635423 | WO9409010 | WO9205179 | U.S. Pat. No. 5,457,194 | U.S. Pat. No. 5,210,030 |
| WO9603430 | WO9404540 | U.S. Pat. No. 5,604,234 | U.S. Pat. No. 5,457,182 | U.S. Pat. No. 5,208,241 |
| WO9600282 | WO9402485 | U.S. Pat. No. 5,597,715 | U.S. Pat. No. 5,362,735 | U.S. Pat. No. 5,200,411 |
| WO9516691 | WO9402137 | U.S. Pat. No. 5,583,139 | U.S. Pat. No. 5,324,644 | U.S. Pat. No. 5,198,421 |
| WO9515328 | WO9402136 | U.S. Pat. No. 5,563,172 | U.S. Pat. No. 5,318,895 | U.S. Pat. No. 5,147,877 |
| WO9507468 | WO9325533 | U.S. Pat. No. 5,561,228 | U.S. Pat. No. 5,310,903 | U.S. Pat. No. 5,140,018 |
| WO9504738 | WO9318043 | U.S. Pat. No. 5,561,137 | U.S. Pat. No. 5,310,901 | U.S. Pat. No. 5,116,756 |
| WO9504060 | WO9313663 | U.S. Pat. No. 5,541,193 | U.S. Pat. No. 5,258,389 | U.S. Pat. No. 5,109,112 |
| WO9425022 | WO9311130 | U.S. Pat. No. 5,541,189 | U.S. Pat. No. 5,252,732 | U.S. Pat. No. 5,093,338 |
| WO9421644 | WO9310122 | U.S. Pat. No. 5,534,632 | U.S. Pat. No. 5,247,076 | U.S. Pat. No. 5,091,389 |

Structural Analogues of Rapamycin (Rapalogs)

A large number of structural variants of rapamycin have been reported, typically arising as alternative fermentation products or from synthetic efforts to improve the compound's therapeutic index as an immunosuppressive agent. Each of Anti-Peptide mTOR Antibodies Anti-peptide antibodies may be produced against mTOR peptide sequences: The sequences chosen may be based on the mouse sequences as follow from the following mTOR reference sequence:

```
   1 mlgtgpavat asaatssnvs vlqqfasglk srneetraka akelqhyvtm elremsqees
  61 trfydqlnhh ifelvsssda nerkggilai asligveggn strigrfany lrnllpssdp
 121 vvmemaskai grlamagdtf taeyvefevk ralewlgadr negrrhaavl vlrelaisvp
 181 tfffqqvqpf fdnifvavwd pkqairegav aalraclilt tqrepkemqk pqwyrhtfee
 241 aekgfdetla kekgmnrddr ihgallilne lvrissmege rlreemeeit qqqlvhdkyc
 301 kdlmgfgtkp rhitpftsfq avqpqqpnal vgllgysspq glmgfgtsps pakstlvesr
 361 ccrdlmeekf dqvcqwvlkc rssknsliqm tilnllprla afrpsaftdt qylqdtmnhv
 421 lscvkkeker taafqalgll svavrsefkv ylprvldiir aalppkdfah krqktvqvda
 481 tvftcismla ramgpgiqqd ikellepmla vglspaltav lydlsrqipq lkkdiqdgll
 541 kmlslvlmhk plrhpgmpkg lahqlaspgl ttlpeasdva sitlalrtlg sfefeghslt
 601 qfvrhcadhf lnsehkeirm eaartcscll tpsihlisgh ahvvsqtavg vvadvlskll
 661 vvgitdpdpd irycvlasld erfdahlaqa enlqalfval ndqvfeirel aictvgrlss
 721 mnpafvmpfl rkmliqilte lehsgigrik eqsarmlghl vsnaprlirp ymepilkali
 781 lklkdpdpdp npgvinnvla tigelaqvsg lemrkwvdel fiiimdmlqd ssllakrqva
 841 lwtlgqlvas tgyvvepyrk yptllevlln flkteqnqgt rreairvlgl lgaldpykhk
 901 vnigmidqsr dasavslses kssqdssdys tsemlvnmgn lpldefypav smvalmrifr
 961 dqslshhhtm vvqaitfifk slglkcvqfl pqvmptflnV irvcdgaire flfqqlgmlv
1021 sfvkshirpy mdeivtlmre fwvmntsiqs tiilliegiv valggefkly lpgliphmlr
1081 vfmhdnsqgr ivsikllaai qlfganlddy lhlllppivk lfdapevplp srkaaletvd
1141 rltesldftd yasriihpiv rtldqspelr stamdtlssl vfqlgkkyqi fipmvnkvlv
1201 rhrinhqryd vlicrivkgy tladeeeedpl iyqhrmlrss qgdalasgpv etgpmkklhv
1261 stinlqkawg aarrvskddw lewlrrlsle llkdsssps1 rscwalaqay npmardlfna
1321 afvscwseln edqqdelirs ielaltsqdi aevtqtlllnl aefmehsdkg plplrddngi
1381 vllgeraakc rayakalhyk elefqkgptp aileslisin nklqqpeaas gvleyamkhf
1441 geleiqatwy eklhewedal vaydkkmdtn kedpelmlgr mrclealgew gqlhqqccek
1501 wtlvndetqa kmarmaaaaa wglgqwdsme eytcmiprdt hdgafyravl alhqdlfsla
1561 qqcidkardl ldaeltamag esysraygam vschmlsele eviqyklvpe rreiirqiww
1621 erlqgcgriv edwgkilmvr slvvsphedm rtwlkyaslc gksgrlalah ktlvlllgvd
1681 psrqldhplp tahpqvtyay mknmwksark idafqhmqhf vqtmqqqaqh aiatedqqhk
1741 gelhklmarc flklgewqln lqginestip kvlqyysaat ehdrswykaw hawavmnfea
1801 vlhykhqnqa rdekkklrha sganitnatt aattaasaaa atstegsnse seaesnensp
1861 tpsplqkkvt edlsktllly tvpavqgffr sislsrgnnl qdtlrvltlw fdyghwpdvn
1921 ealvegvkai qidtwlqvip qliaridtpr plvgrlihql ltdigryhpq aliypltvas
1981 kstttarhna ankilknmce hsntivqqam mvseelirva ilwhemwheg leeasrlyfg
2041 ernvkgmfev leplhammer gpqtlketsf nqaygrdlme aqewcrkymk sgnvkdltqa
2101 wdlyyhvfrr iskqlpqlts lelqyvspkl lmcrdlelav pgtydpnqpi iriqsiapsl
2161 qvitskqrpr kltlmgsngh efvfllkghe dlrqdervmq lfglvntlla ndptslrknl
2221 siqryavipl stnsgligwv phcdtlhali rdyrekkkil lniehrimlr mapdydhltl
2281 mqkvevfeha vnntagddla kllwlkspss evwfdrrtny trslavmsmv gyilglgdrh
2341 psnlmldrls gkilhidfgd cfevamtrek fpekipfrlt rmltnamevt gldgnyrttc
2401 htvmevlreh kdsvmavlea fvydpllnwr lmdtntkgnk rsrtrtdsys agqsveildg
```

```
2461 velgepahkk agttvpesih sfigdglvkp ealnkkaiqi inrvrdkltg rdfshddtld 2521 vptqvellik qatshenlcq cyigwcpfw
```

Thus, preferred anti-peptide antibodies may be raised from any one or more of the following sequences: amino acids 22-139; amino acids 647-907; amino acids 937-1140; amino acids 1382-1982; amino acids 2019-2112; or amino acids 2181-2549.

Corresponding sequences from human mTOR may be chosen for use in eliciting anti-peptide antibodies from immunised animals. Antibodies may be produced by injection into rabbits, and other conventional means, as described in for example, Harlow and Lane (supra).

Antibodies are checked by Elisa assay and by Western blotting, and used for immunostaining as described in the Examples.

Downregulation of PDK1

The methods and compositions described here involve in part down-regulating the activity and/or expression of PDK1.

In general terms, our methods involve manipulation of cancer cells, by modulating (such as down-regulating) the expression, amount or activity of PDK1 in the cell. A step of detecting modulated PDK1 expression, amount or activity in a cell may be conducted before or after the manipulation step. The detection step may detect up-regulated or down-regulated PDK1 expression, amount or activity. Any of the methods of modulating or down-regulating PDK1, as described in detail elsewhere in this document, may be used.

For example, PDK1 activity and/or expression may be down-regulated by use of PDK1 inhibitors, including small molecule inhibitors of PDK1. An example of a PDK1 inhibitor is BX795 (CAS No.: 702675-74-9).

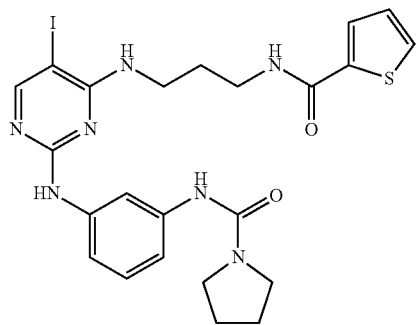 [SMILES: O=C(NCCCNc1nc(Nc2cccc(NC(=O)N3CCCC3)c2)ncc1I)c1cccs1]

Other PDK1 inhibitors which may be suitable for use in down-regulating the activity and/or expression of PDK1 are described in R I Feldman et al. Novel Small Molecule Inhibitors of 3-Phosphoinositide-dependent Kinase-1. J. Biol. Chem., 2005, 280, 20, 19867-19874 and C Peifer, D R. Alessi, Small-Molecule Inhibitors of PDK1. ChemMedChem. 2008, 3 (10).

The method may comprise exposing the cell to an siRNA or shRNA or an anti-PDK1 antibody capable of specifically binding to PDK1. PDK1 may be modulated by targeting a PDK1 target site selected from any suitable site in the PDK1 sequence.

According to our methods, the cancer cell becomes non-cancerous or sensitive to mTOR inhibitors as a result of the manipulation. The cancer may in particular comprise cancers such as colorectal cancer, bladder cancer, oesophageal cancer and brain cancer, as well as mTOR inhibitor resistant forms thereof (e.g., rapamycin resistant or rapamycin derivative resistant forms of such cancers).

The level of PDK1 may be detected in a cell of an individual with cancer, in a cancer or non-cancer cell, and the sensitivity of the cancer to treatments such as mTOR inhibitors assessed. A high level of PDK1 amount, expression or activity compared with a normal cell indicates an mTOR inhibitor resistant form (e.g., rapamycin resistant or rapamycin derivative resistant form) of cancers such as colorectal cancer, bladder cancer, oesophageal cancer and brain cancer. Alternative therapies may therefore be chosen, including use of PDK1 inhibitors and antagonists.

A cancer is defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, etc. By the term "treatment" we mean to also include prophylaxis or alleviation of cancer.

PDK1 polypeptide represents a target for inhibition of its function for therapy, particularly in tumour cells and other proliferative cells.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leimyosarcoma, rhabdomyosarcoma, colon carcinoma, ovarian cancer, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neutroblastoma and retinoblastoma.

One possible approach for therapy of such disorders is to express anti-sense constructs directed against PDK1 polynucleotides as described here, and administering them to tumour cells, to inhibit gene function and prevent the tumour cell from growing or progressing.

Anti-sense constructs may be used to inhibit gene function to prevent growth or progression in a proliferative cell. Anti-sense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit. Rev Oncog* 3(1-2):175-231, the teachings of which document are specifically incorporated by reference.

In a particular example, cancers such as colorectal cancer, bladder cancer, oesophageal cancer and brain cancer, as well as mTOR inhibitor resistant forms thereof (e.g., rapamycin resistant or rapamycin derivative resistant forms of such cancers) may be treated or prevented by reducing the amount, expression or activity of PDK1 in whole or in part, for example by siRNAs capable of binding to and destroying PDK1 mRNA. We specifically provide for an anti-PDK1 agent which downregulates PDK1 by RNA interference. The anti-PDK1 agent may comprise a Small Interfering RNA (siRNA) or Short Hairpin RNA (shRNA).

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., *Nature* 391:806-811 (1998). Other methods of PTGS are known and include, for example, introduction of a transgene or virus. Generally, in PTGS, the transcript of the silenced gene is synthesised but does not accumulate because it is rapidly degraded, Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the PDK1 nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of a PDK1 polynucleotide can be introduced into or expressed in oocytes and cells of a candidate organism to interfere with PDK1 activity.

Other methods of modulating PDK1 gene expression are known to those skilled in the art and include dominant negative approaches. Thus, another approach is to use non-functional variants of PDK1 polypeptide in this document that compete with the endogenous gene product resulting in inhibition of function.

PDK1 gene expression may also be modulated by as introducing peptides or small molecules which inhibit gene expression or functional activity. Thus, compounds identified by the assays described here as binding to or modulating, such as down-regulating, the amount, activity or expression of PDK1 polypeptide may be administered to tumour or proliferative cells to prevent the function of PDK1 polypeptide. Such a compound may be administered along with a pharmaceutically acceptable carrier in an amount effective to down-regulate expression or activity PDK1, or by activating or down-regulating a second signal which controls PDK1 expression, activity or amount, and thereby alleviating the abnormal condition.

Suitable antibodies against PDK1 polypeptide as described herein may also be used as therapeutic agents. An anti-PDK1 antibody may comprise a rabbit anti-PDK1 antibody.

Alternatively, gene therapy may be employed to control the endogenous production of PDK1 by the relevant cells in the subject. For example, a polynucleotide encoding a PDK1 siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-PDK1 siRNA such that the packaging cell now produces infectious viral particles containing the sequence of interest. These producer cells may be administered to a subject for engineering cells in vivo and regulating expression of the PDK1 polypeptide in vivo. For overview of gene therapy, see Chapter 20; Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of PDK1 is decreased in a cancer cell. Furthermore, in such embodiments, treatment may be targeted to, or specific to, cancers cells such as colorectal cancer cells, bladder cancer cells, oesophageal cancer cells and brain cancer cells.

The expression of PDK1 may be specifically decreased only in diseased cancer cells (i.e., those cells which are cancerous), and not substantially in other non-diseased cancer cells. In these methods, expression of PDK1 may be not substantially reduced in other cells, i.e., cells which are not colorectal cancer cells, bladder cancer cells, oesophageal cancer cells or brain cancer cells. Thus, in such embodiments, the level of PDK1 remains substantially the same or similar in such other cells in the course of or following treatment.

Colorectal cancer cell, bladder cancer cell, oesophageal cancer cell and brain cancer cell specific reduction of PDK1 levels may be achieved by targeted administration, i.e., applying the treatment only to such cells and not other cells. However, in other embodiments, down-regulation of PDK1 expression in such cells (and not substantially in other cell or tissue types) is employed. Such methods may advantageously make use of tissue specific expression vectors, for tissue specific expression of for example siRNAs.

Identifying mTOR Antagonists and PDK1 Antagonists

Antagonists, in particular, small molecules may be used to specifically inhibit mTOR and/or PDK1 or both.

We therefore disclose small molecule mTOR inhibitors, as well as assays for screening for these. Antagonists of mTOR kinase may be screened by detecting modulation, preferably down regulation, of binding or other activity. Any mTOR antagonists identified may be employed in the methods and compositions described here.

We also disclose small molecule inhibitors of PDK1, as well as assays for screening for these. Inhibitors of PDK1 are screened by detecting modulation, preferably down regulation, of PDK1 itself, or any activity associated with PDK1, for example, PDK1 mediated Myc phosphorylation activity, etc.

By "down-regulation" we include any negative effect on the behaviour being studied; this may be total, or partial. Thus, where binding is being detected, candidate antagonists are capable of reducing, ameliorating, or abolishing the binding between two entities. Preferably, 10 the down-regulation of binding (or any other activity) achieved by the candidate molecule is at least 10%, preferably at least 20%, preferably at least 30%, preferably at least 40%, preferably at least 50%, preferably at least 60%, preferably at least 70%, preferably at least 80%, preferably at least 90%, or more compared to binding (or which ever activity) in the absence of the candidate molecule. Thus, a candidate molecule suitable for use as an antagonist is one which is capable of reducing by 10% more the binding or other activity.

Polypeptide Binding Assays

Modulators and antagonists of mTOR activity or expression may be identified by any means known in the art. Putative such molecules may be identified by their binding to mTOR, in an assay which detects binding between mTOR and the putative molecule.

Similarly, modulators and antagonists of PDK1 activity or expression may be identified by any means known in the art. Putative such molecules may be identified by their binding to PDK1, in an assay which detects binding between PDK1 and the putative molecule.

One type of assay for identifying substances that bind to a polypeptide involves contacting a polypeptide, which is immobilised on a solid support, with a non-immobilised candidate substance determining whether and/or to what extent the polypeptide and candidate substance bind to each other. Alternatively, the candidate substance may be immobilised and the polypeptide non-immobilised. This may be used to detect substances capable of binding to mTOR polypeptides or PDK1 as the case may be, or fragments, homologues, variants or derivatives thereof.

In a preferred assay method, the polypeptide is immobilised on beads such as agarose beads. Typically this is achieved by expressing the mTOR polypeptide or PDK1 as the case may be, or a fragment, homologue, variant or derivative thereof as a GST-fusion protein in bacteria, yeast or higher eukaryotic cell lines and purifying the GST-fusion protein from crude cell extracts using glutathione-agarose beads (Smith and Johnson, 1988). As a control, binding of the candidate substance, which is not a GST-fusion protein, to the immobilised polypeptide is determined in the absence of the polypeptide. The binding of the candidate substance to the immobilised polypeptide is then determined. This type of assay is known in the art as a GST pulldown assay. Again, the candidate substance may be immobilised and the polypeptide non-immobilised.

It is also possible to perform this type of assay using different affinity purification systems for immobilising one of the components, for example Ni-NTA agarose and histidine-tagged components.

Binding of the mTOR polypeptide or PDK1 polypeptide, or a fragment, homologue, variant or derivative thereof to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, more preferably from 1 to 100 nmol/ml. In the case of antibodies, the final concentration used is typically from 100 to 500 µg/ml, more preferably from 200 to 300 µg/ml.

Modulators and antagonists of mTOR and PDK1 may also be identified by detecting modulation of binding between mTOR or PDK1 and any molecule to which these bind.

Activity Assays

Assays to detect modulators or antagonists typically involve detecting modulation of any activity of mTOR, preferably kinase activity, or PDK1 activity, in the presence, optionally together with detection of modulation of activity in the absence, of a candidate molecule.

The assays involve contacting a candidate molecule (e.g., in the form of a library) with mTOR or PDK1 whether in the form of a polypeptide, a nucleic acid encoding the polypeptide, or a cell, organelle, extract, or other material comprising such, with a candidate modulator. The relevant activity of mTOR or PDK1 (as described below) may be detected, to establish whether the presence of the candidate modulator has any effect. Promoter binding assays to detect candidate modulators which bind to and/or affect the transcription or expression of mTOR or PDK1 may also be used. Candidate modulators may then be chosen for further study, or isolated for use. Details of such screening procedures are well known in the art, and are for example described in, Handbook of Drug Screening, edited by Ramakrishna Seethala, Prabhavathi B. Fernandes (2001, New York, N.Y., Marcel Dekker, ISBN 0-8247-0562-9).

The screening methods described here preferably employ in vivo assays, although they may be configured for in vitro use. In vivo assays generally involve exposing a cell comprising mTOR or PDK1 to the candidate molecule. In in vitro assays, mTOR or PDK1 is exposed to the candidate molecule, optionally in the presence of other components, such as crude or semi-purified cell extract, or purified proteins. Where in vitro assays are conducted, these preferably employ arrays of candidate molecules (for example, an arrayed library). In vivo assays are preferred. Preferably, therefore, the mTOR or PDK1 is comprised in a cell, preferably heterologously. Such a cell is preferably a transgenic cell, which has been engineered to express mTOR or PDK1 as described above.

Where an extract is employed, it may comprise a cytoplasmic extract or a nuclear extract, methods of preparation of which are well known in the art.

It will be appreciated that any component of a cell comprising mTOR or PDK1 may be employed, such as an organelle. A preferred embodiment utilises a cytoplasmic or nuclear preparation, e.g., comprising a cell nucleus which comprises mTOR as described. See Zhang, et al, Predominant Nuclear Localization of Mammalian Target of Rapamycin in Normal and Malignant Cells in Culture. J. Biol. Chem., July 2002; 277: 28127-28134. The nuclear preparation may comprise one or more nuclei, which may be permeabilised or semi-permeabilised, by detergent treatment, for example.

Thus, in a specific embodiment, an assay format may include the following: a multiwell microtitre plate is set up to include one or more cells expressing mTOR or PDK1 in each well; individual candidate molecules, or pools of candidate molecules, derived for example from a library, may be added to individual wells and modulation of mTOR or PDK1 activity measured. Where pools are used, these may be subdivided in to further pools and tested in the same manner. mTOR or PDK1 activity, for example, kinase activity, is then assayed.

Alternatively or in addition to the assay methods described above, "subtractive" procedures may also be used to identify modulators or antagonists of mTOR or PDK1. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising mTOR or PDK1 (or a component thereof) as described.

Thus, for example, an 'immunodepletion' assay may be conducted to identify such modulators as follows. A cytoplasmic or nuclear extract may be prepared from a pluripotent cell, for example, a pluripotent EG/ES cell. The extract may be depleted or fractionated to remove putative modulators, such as by use of immunodepletion with appropriate antibodies. If the extract is depleted of a modulator, it will lose the ability to affect mTOR or PDK1 function or activity or expression. A series of subtractions and/or depletions may be required to identify the modulators or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In a preferred embodiment, more than one candidate molecule is screened simultaneously. A library of candidate molecules may be generated, for example, a small molecule library, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising mTOR or PDK1 may be exposed to individual members of the library, and effect on the mTOR activity or PDK1 activity determined. Array technology may be employed for this purpose. The cells may be spatially separated, for example, in wells of a microtitre plate.

In a preferred embodiment, a small molecule library is employed. By a "small molecule", we refer to a molecule whose molecular weight is preferably less than about 50 kDa. In particular embodiments, a small molecule has a molecular weight preferably less than about 30 kDa, more preferably less than about 15 kDa, most preferably less than 10 kDa or so. Libraries of such small molecules, here referred to as "small molecule libraries" may contain polypeptides, small peptides, for example, peptides of 20 amino acids or fewer, for example, 15, 10 or 5 amino acids, simple compounds, etc.

Alternatively or in addition, a combinatorial library, as described in further detail below, may be screened for modulators or antagonists of mTOR or PDK1.

Assays for mTOR Activity

Any of the activities of mTOR may be used as the basis of the assay.

In particular, cellular activities mediated by mTOR may be assayed to identify antagonists. For example, mTOR is responsible for phosphorylating substrates including eukaryotic initiation factor 4E (eIF4E) and ribosomal S6 kinase 1 (S6K1), RNA polymerase I and eEF2 kinase. Accordingly, the effects of the putative antagonist or agonist on kinase activity mediated by mTOR one or more of these substrates (or peptides derived from their sequences) may be assayed using for example kinase assays as known in the art.

Such assays may employ 4E-BP1 and/or S6K1 as substrates, or use peptides from these polypeptides as substrates. mTOR is known to phosphorylate 4E-BP1 at Thr37 and Thr46 and S6K1 at Thr389 (Schalm S S, Fingar D C, Sabatini D M, Blenis J. Curr Biol. 2003 May 13; 13(10):797-806; Schalm S S, Blenis J. Curr Biol. 2002 Apr. 16; 12(8):632-9.), and accordingly peptide substrates containing these positions may be generated using known peptide synthesis methods.

An exemplary assay for kinase activity of mTOR is described in Gary G. Chiang, Robert T. Abraham. *Determination of the Catalytic Activities of mTOR and Other Members of the Phosphoinositide-3-Kinase-Related Kinase Family*. Checkpoint Controls and Cancer: Volume 2: Activation and Regulation Protocols, July 2004, pps. 125-142 (ISBN: 1-59259-811-0), Volume #: 281, Series: Methods in Molecular Biology.

mTOR Kinase Assay

A further mTOR assay is disclosed in Molecular Mechanism of mTOR Downstream Signalling (PhD Thesis, S. Schalm, 17 Sep. 2003, Fachbereich Biologie, Chemie, Pharmazie, Freie Universität Berlin, http://www.diss.fu-berlin.de/2003/249/index.html).

Cells are grown for 48 hours in DMEM containing 10% FBS, and lysed in lysis buffer B (40 mM HEPES, 120 mM NaCl, 50 mM NaF, 1 mM EDTA, 50 mM β-glycerophosphate, 0.2% CHAPS, 1 mM $Na_3$ VO4, 40 mg/ml PMSF, 5 mg/ml pepstatin, 10 mg/ml leupeptin, 1 mM DTT, ddH2, O, pH 7.5). One third of total cell lysate from a 150-mm plate is incubated with an anti mTOR-antibody (e.g., Bethyl, Inc, Texas USA) for 2 h, followed by another hour of incubation with protein-G-Sepharose beads. Immunopreciptates are washed twice with 1 ml mTOR wash buffer A (20 mM Tris, 500 mM NaCl, 1 mM EDTA, 20 mM β-glycerophosphate, 5 mM EGTA, 1 mM DTT, 1 mM $Na_3$ VO4, 40 mg/ml PMSF, 10 mg/ml leupeptin, 5 µg/ml pepstatin, in ddH2O, pH 7.4), once with mTOR wash buffer B (10 mM HEPES, 50 mM β-glycerophosphate, 50 mM NaCl, 1 mM DTT, 1 mM $Na_3$ VO4, 40 mg/ml PMSF, 10 µg/ml leupeptin, 5 mg/ml pepstatin, in ddH2O, pH 7.4), and once with ST (50 mM Tris-HCl, 5 mM Tris base, 150 mM NaCl, ddH2O, pH 7.28).

Kinase assays towards recombinant GST-4E-BP1 WT or GST-4E-BP1 F114A (i.e., human 4E-BP1 subcloned into pGEX-2T/GST, Pharmacia) in washed immunoprecipitates is assayed in mTOR kinase assay buffer (10 mM HEPES, 50 mM NaCl, 50 mM β-glycerophosphate, 10 mM $MnCl_2$, 100 µM ATP unlabeled, 10 µCi [$\gamma$-$_{32}$P] ATP (New England Nuclear), pH 7.4) for 30 min at 30° C. The reaction is separated by 12% SDS-PAGE and $_{32}$P incorporated into GST-4E-BP1 is assessed by autoradiography and quantified by phosphoimaging (BioRad). One kinase unit is defined by the amount of kinase ie protein required to catalyze the transfer of 1 µmol of phosphate to the substrate per reaction volume in one minute at 30° C.

mTOR Reporter Assay

Figure 9A:
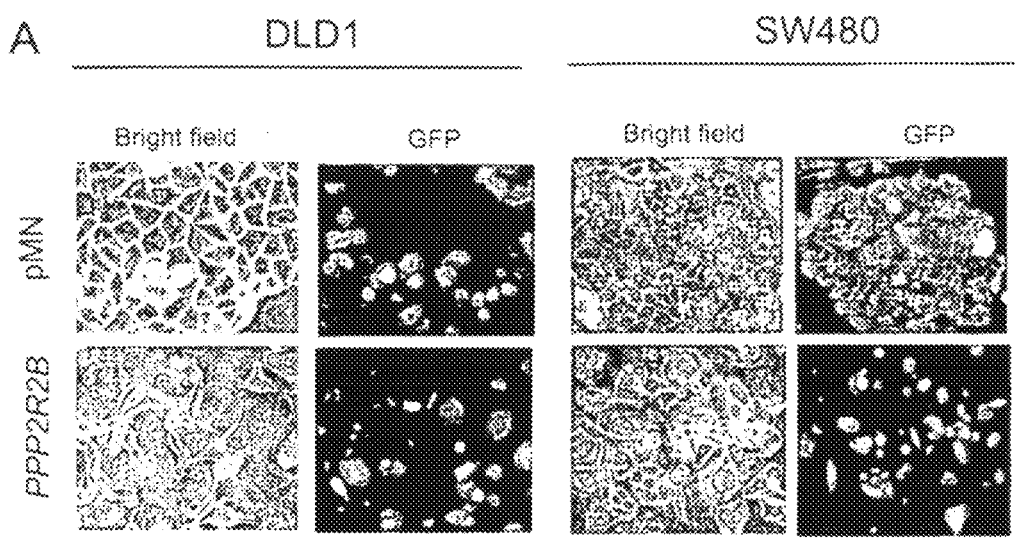
FIGS. 9A-9B. Effects of PPP2R2B re-expression on colon cancer cell growth. DLD1, HT29 and SW480 cells were infected with pMN-GFP (control vector) or pMN-GFP-PPP2R2B retrovirus and cells were sorted with GFP selection. The morphologies of DLD1 and SW480 cells induced by PPP2R2B re-expression are shown in FIG. 9A and the anchorage-independent growth of SW480 and HT29 is shown in FIG. 9B. Scale bars=100 μm.

Molecules and agents which activate or promote mTOR activity may be identified as follow: To screen for mTOR activating molecules, a hybrid gene encoding for a mRNA with a 5'UTR derived from a TOP mRNA e.g. L5 ribosomal protein mRNA and coding region from a reporter gene e.g. GFP or luciferase is transfected into mammalian cells. The cells are either serum starved or rapamycin-treated to shut off translation of the reporter. Cells are exposed to a candidate molecule or a member of a library. Addition of an mTOR activating molecule will upregulate translation of the reporter (see FIG. 9A and Example 8)

Molecules and agents which inhibit mTOR activity are identified as follow: To screen for mTOR inhibiting molecules, a hybrid gene encoding a mRNA with a 5'UTR derived from mRNAs whose translation is upregulated when cap-mediated translation is inhibited e.g. p27Kip1 mRNA and coding region from a reporter gene e.g. GFP or luciferase is transfected into mammalian cells. The cells are either serum starved or rapamycin-treated to turn on translation of the reporter. Then serum will be added or rapamycin removed to activate mTOR and turn off translation of reporter. Cells are exposed to a candidate molecule or a member of a library.

Figure 9B:
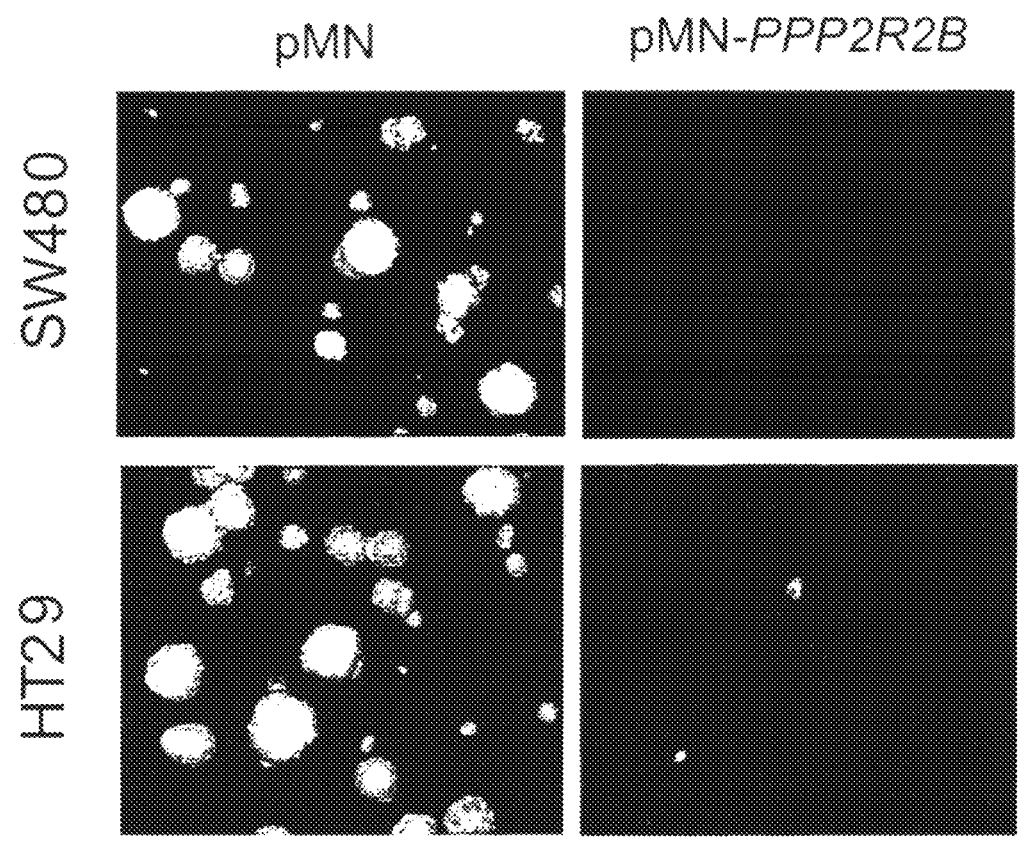

When the reporter is off, mTOR inhibiting molecule will be added to upregulate translation of the reporter (see FIG. 9B and Example 9).

Cell Cycle Assay

Furthermore, we show that mTOR activity is capable of lengthening cell cycle times; accordingly, the cell cycle period may be assayed in the presence and absence of a candidate molecule to identify antagonists or agonists of mTOR activity.

Assays for PDK1 Activity

Any of the various biochemical other activities of PDK1 may be measured in order to assay PDK1 activity. Accordingly, the effects of a putative antagonist or agonist on PDK1 activity may be assayed by any one or more of the following methods as known in the art.

Assays for PDK1 activity are known in the art and include for example a PDK1 Kinase Assay Kits sold by Upstate Biotechnology and Millipore (Catalogue No. 17-280, Upstate Biotechnology, Lake Placid, N.Y., USA) as well as the HTScan® PDK1 Kinase Assay Kit (Catalogue No. 7577, Cell Signalling Technology, Danvers, Mass., USA).

Libraries

Libraries of candidate molecules, such as libraries of polypeptides or nucleic acids, may be employed in the screens for mTOR antagonists and PDK1 inhibitors described here. Such libraries are exposed to mTOR protein, and their effect, if any, on the activity of the protein determined. Similarly, the libraries may be exposed to an experimental system and their effect, if any, on PDK1 determined.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al, (1990) supra; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference). Such techniques may be modified if necessary for the expression generally of polypeptide libraries.

One particularly advantageous approach has been the use of scFv phage-libraries (Bird, R. E., et al. (1988) *Science* 242: 423-6, Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) *Science*, 246: 1275; Caton and Koprowski (1990) *Proc. Natl. Acad. Sci. U.S.A.*, 87; Mullinax et al. (1990) *Proc. Natl. Acad. Sci. U.S.A.*, 87: 8095; Persson et al. (1991) *Proc. Natl. Acad. Sci. U.S.A.*, 88: 2432) and are of use in the methods and compositions described here. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

The library may in particular comprise a library of zinc fingers; zinc fingers are known in the art and act as transcription factors. Suitable zinc finger libraries are disclosed in, for example, WO 96/06166 and WO 98/53057. Construction of zinc finger libraries may utilise rules for determining interaction with specific DNA sequences, as disclosed in for example WO 98/53058 and WO 98/53060. Zinc fingers capable of interacting specifically with methylated DNA are disclosed in WO 99/47656. The above zinc finger libraries may be immobilised in the form of an array, for example as disclosed in WO 01/25417. Accordingly, preferred molecules capable of altering the potency of a cell include zinc fingers.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randthnly selected subunits. Combinatorial libraries may be screened for molecules which are capable of inhibiting mTOR or PDK1.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), *Journal of Combinatorial Chemistry*, Vol 1 No 4, 23:5-282. Reference is also made to *Combinatorial peptide library protocols* (edited by Shmuel Cabilly, Totowa, N.J.: Humana Press, c1998. *Methods in Molecular Biology*; v. 87). Specific combinatorial libraries and methods for their construction are disclosed in U.S. Pat. No. 6,168,914 (Campbell, et al), as well as in Baldwin et al. (1995), "Synthesis of a Small Molecule Library Encoded with Molecular Tags," J. Am. Chem. Soc. 117:5588-5589, and in the references mentioned in those documents.

In a preferred embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone methylation enzymes), or DNA modification, for example, DNA methylation or demethylation.

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead'(Lam, K. S. et al., 1991, Nature 354: 82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al, 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Antibodies

Specific antagonists of mTOR, which may be used to regulate the activity of these proteins (for example, for methods of treating or preventing diseases such as cancer) may include antibodies against the mTOR protein.

Similarly, PDK1 inhibitors may include antibodies against any molecule involved in the PDK1.

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution.

The antibodies described here may be altered antibodies comprising an effector protein such as a label. Especially preferred are labels which allow the imaging of the distribution of the antibody in vivo or in vitro. Such labels may be radioactive labels or radioopaque labels, such as metal particles, which are readily visualisable within an embryo or a cell mass. Moreover, they may be fluorescent labels or other labels which are visualisable on tissue samples.

Recombinant DNA technology may be used to improve the antibodies as described here. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [EP 0 239 400].

Antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration; ion-exchange chromatography, chromatography over DEAE-cellulose and/or (immuno-) affinity chromatography, e.g. affinity chromatography with mTOR, or fragments thereof, or with Protein-A.

Hybridoma cells secreting the monoclonal antibodies are also provided. Preferred hybridoma cells are genetically stable, secrete monoclonal antibodies of the desired specificity and can be activated from deep-frozen cultures by thawing and recloning.

Also included is a process for the preparation of a hybridoma cell line secreting monoclonal antibodies directed to mTOR, characterised in that a suitable mammal, for example a Balb/c mouse, is immunised with a one or more mTOR polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with mTOR are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells expressing mTOR and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to mTOR as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to mTOR can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly E. coli, to obtain an optimal expression of the heavy chain murine variable domain and/or a light chain murine variable domain.

The term mutant is intended to include a DNA mutant obtained by in vitro mutagenesis of the authentic DNA according to methods known, in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to mTOR fused to a human constant domain g, for example γ1, γ2, γ3 or γ4, preferably γ1 or γ4. Likewise recombinant DNAs comprising an insert coding for a light chain murine variable domain of an antibody directed to mTOR fused to a human constant domain κ or λ, preferably κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Antibody Delivery

The antibodies against the mTOR protein or antibodies against PDK1, for example, anti-PDK1 antibodies, may be delivered into a cell by means of techniques known in the art, for example by the use of liposomes, polymers, (e.g., polyethylene glycol (PEG), N-(2-hydroxypropyl) methacrylamide (HPMA) copolymers, polyamidoamine (PAMAM) dendrimers, HEMA, linear polyamidoamine polymers etc) etc. The immunoglobulins and/or antibodies may also be delivered into cells as protein fusions or conjugates with a protein capable of crossing the plasma membrane and/or the nuclear membrane. For example, the immunoglobulin and/or target may be fused or conjugated to a domain or sequence from such a protein responsible for the translocational activity. Preferred translocation domains and sequences include domains and sequences from the HIV-1-trans-activating protein (Tat), *Drosophila* Antennapedia homeodomain protein and the herpes simplex-1 virus VP22 protein.

Further Aspects

Further aspects of the invention are set out in the following numbered paragraphs; it is to be understood that the invention includes these aspects.

Paragraph 1. A method of determining whether a cancer cell is likely to be resistant to treatment by an mTOR inhibitor, the method comprising detecting: (i) PPP2R2B (GenBank Accession Number: NM_181678) or (ii) PDK1 (GenBank Accession Number: NM_002613), or both, in or of the cell.

Paragraph 2. A method according to Paragraph 1, which comprises detecting methylation of the PPP2R2B promoter in or of the cell.

Paragraph 3. A method according to Paragraph 1 or 2, in which hypermethylation of the PPP2R2B promoter, compared to a cancer cell that is not mTOR inhibitor resistant, indicates that the cancer cell is likely to be resistant to treatment by an mTOR inhibitor.

Paragraph 4. A method according to Paragraph 1, 2 or 3, which comprises detecting expression and/or activity of PPP2R2B or PDK1, or both, in or of the cell.

Paragraph 5. A method according to any preceding paragraph, in which activity of PDK1 comprises PDK1 mediated Myc phosphorylation activity.

Paragraph 6. A method according to any preceding paragraph, in which a decreased expression and/or activity of PPP2R2B, or an increased expression and/or activity of PDK1, or both, compared to a cancer cell that is not mTOR inhibitor resistant, indicates that the cancer cell is likely to be resistant to treatment by an mTOR inhibitor.

Paragraph 7. A method of choosing a treatment for an individual suffering from or suspected to be suffering from a cancer, the method comprising: (a) providing a cell of the patient; (b) detecting mTOR inhibitor resistance of the cell by method according to any preceding Paragraph; and (c) where the cell is determined not to be mTOR inhibitor resistant, choosing an mTOR inhibitor as a treatment for the individual, and where the cell is determined to be mTOR inhibitor resistant, choosing a different treatment for the individual.

Paragraph 8. A method of determining whether an individual suffering from or suspected to be suffering from a cancer will respond to treatment by an mTOR inhibitor, the method comprising performing a method according to any of Paragraphs 1 to 6 on a cell of the individual, and, where the cell is determined not to be mTOR inhibitor resistant, determining that the individual is likely to respond to treatment by an mTOR inhibitor.

Paragraph 9. A method of increasing the sensitivity of a cancer cell to treatment by an mTOR inhibitor, the method comprising increasing expression and/or activity of PPP2R2B, or decreasing expression and/or activity of PDK1, or both, in or of the cell.

Paragraph 10. A method of treating or preventing cancer in an individual suffering or suspected to be suffering from cancer, the method comprising increasing expression and/or activity of PPP2R2B, or decreasing expression and/or activity of PDK1, or both, in or of the individual.

Paragraph 11. A method according to Paragraph 9 or 10, in which expression of PPP2R2B is increased by decreasing methylation of the PPP2R2B promoter.

Paragraph 12. A method according to Paragraph 9, 10 or 11, which comprises exposing the cell to, or administering to a patient, a demethylating agent such as 5-aza-dC.

Paragraph 13. A method according to any of Paragraphs 9 to 12, which comprises exposing the cell to, or administering to a patient, a PDK1 inhibitor such as BX912 (CAS Accession Number: 702674-56-4).

Paragraph 14. A method of treating or preventing cancer in an individual suffering or suspected to be suffering from cancer, the method comprising administering an inhibitor of PDK1 expression and/or activity together with an mTOR inhibitor.

Paragraph 15. A combination of an inhibitor of PDK1 expression and/or activity and an mTOR inhibitor for use in a method of treatment or prevention of cancer.

Paragraph 16. Use of a combination of an inhibitor of PDK1 expression and/or activity and an mTOR inhibitor in the manufacture of a medicament for the treatment or prevention of cancer.

Paragraph 17. Use of PPP2R2B or PDK1, or both, as a biomarker for sensitivity of a cancer cell to an mTOR inhibitor such as rapamycin or a derivative thereof.

Paragraph 18. A method or composition according to any preceding paragraph, in which the mTOR inhibitor comprises rapamycin or a derivative thereof.

Paragraph 19. A method or composition according to any preceding Paragraph, in which the cancer cell is a colon cancer cell, and/or in which the cancer comprises colorectal cancer (CRC).

EXAMPLES

Example 1

Experimental Procedures—Samples, Cell Lines and Drugs

Human tissue samples were obtained from Singapore Tissue Network in accordance with the local ethics committee as previously described (Jiang et al., 2008). The cancer cell lines used in this study were purchased from the American Type Culture Collection (Manassas, Va.).

HCT116 cells with genetic disruption of DNMT1 and DNMT3B (HCT116 DKO) were kindly provided by Dr. Bert Vogelstein (Johns Hopkins University, MD). HEK-TERV cells were a generous gift from Dr. W. C. Hahn at Dana-Farber Cancer Institute. 5-AzaC and Doxycycline were purchased from Sigma.

Rapamycin and PI-103 were purchased from Alexis (San Diego, Calif.). PDK1 inhibitor BX912 and the PIK3CA inhibitor PIK90 were obtained from Axon Medchem (Groningen, Netherlands).

Example 2

Experimental Procedures—Plasmid Constructs and Inducible Cell Lines

Full-length PPP2R2B coding region was isolated by RT-PCR using 100 ng total RNA from normal colon tissue and the following primers: 5'-GGTACCACCatggaggaggacattgatacc-3' (SEQ ID NO: 2) and 5'-CTCGAGCAgttaaccttgtcctgga-3' (SEQ ID NO: 3). The PCR product was cloned into pcDNA4/myc-hisB between Kpn I and Xho I sites for overexpression studies or pcDNA4/TO/myc-hisB for inducible system.

Full-length PDK1 was amplified by RT-PCR using 100 ng total RNA from HEK293 cells and the following primers: 5'-tcGAATTCgccaggaccaccagccagc-3' (SEQ ID NO: 4) and 5'-GAGAATTCctgcacagcggcgtccgg-3' (SEQ ID NO: 5). The PCR product was cloning into pHA.CE vector between EcoRI and sequenced. To generate the PPP2R2B Tet-on inducible cell line, DLD1 or HCT116 stable cell line expressing pcDNA6-TR (Invitrogen) and selected with Blasticidin (10 µg/ml) was first isolated according to the protocols of T-Rex system kit (Invitrogen), and then transfected with the pcDNA4/TO/PPP2R2B-myc and selected for Zeocin (100 µg/ml). The generated clones were screened for doxycycline inducible expression of PPP2R2B. For doxycycline treatment, inducible cells were treated with doxycycline to a final concentration of 1 µg/ml.

To make PPP2R2B retroviral expression, myc-tagged PPP2R2B fragment was subcloned into pMN GFP/IRES retrovirus vector (a gift from Dr. Linda Penn's lab) between BamH I and Xba I sites. Cells were infected with retrovirus packaged with pMN control vector or pMN-PPP2R2B-myc genes for 48 hours and sorted with GFP for further analysis.

Example 3

Experimental Procedures—Illuminar Gene Expression Data, Semi-Quantitative RT-PCR and Taqman Assay Illuminar gene expression data of human CRC and matched normal controls has been described previously (Jiang et al., 2008) and can be found at the GEO public database (accession number GSE10972).

For RT-PCR, total RNA was reverse-transcribed using oligo(dT)12-18 primer (SEQ ID NO: 6)with Superscript II reverse transcriptase (Invitrogen). 100 ng of cDNA was used for PCR. The primers PPP2R2B F: 5' ATGGAGGAGGA-CATTGATACC 3' (SEQ ID NO: 7) and PPP2R2B R: 5' (SEQ ID NO: 8) ACATTGTATTCACCCCTACG 3' were used to amplify the PPP2R2B cDNA.

Quantitative real-time PCR of PPP2R2B was performed on a PRISM 7900 Sequence Detection System (Applied Biosystems) using a TaqMan probe (Applied Biosystems). Samples were normalized to the levels of GAPDH mRNA.

Example 4

Experimental Procedures—DNA Methylation Analysis

Bisulfite modification of DNA was performed by using the EZ DNA methylation-Gold kit (ZYMO Research) according the manufacture's instructions. The CpG island DNA methylation status was determined methylation-specific PCR (MSP) and bisulfite genomic sequencing (BGS) as previously described (Jiang et al., 2008).

MSP primers targeting the PPP2R2B promoter for methylated sets includes: PPP2R2B 5M1, 5' AGTAGTAGTTGC-GAGTGCGC 3' (SEQ ID NO: 9), PPP2R2B 3M1, 5' GAA-CAACCGCGACAAAATAAT 3' (SEQ ID NO: 10). For unmethylated sets: PPP2R2B 5U1, 5' AGTAGTAGTAGT-TGTGAGTGTGT 3' (SEQ ID NO: 11), PPP2R2B 3U1, 5' AAACAACCACAACAAAATAATACC 3' (SEQ ID NO: 12). The MSP results of selected samples were confirmed by bisulfite genomic sequencing.

The strand-specific BGS primers for PPP2R2B promoter were: PPP2R2B BGS1, 5' ATTATTGTTGTTGGGAAAGA 3' (SEQ ID NO: 13) , and PPP2R2B BGS2, 5' CAAAATAATACCTTTCTAAACCC 3' (SEQ ID NO: 14) . The conditions for MSP and bisulfite sequencing PCR are available on request.

Example 5

Experimental Procedures—Antibodies

The following antibodies were used: Myc, p-Myc(T58/S62), p70-S6K, p-p70S6K(T421/S424), p-p70S6K(T389), p-p70S6K(S371), p-AKT (S473), p-AKT (T308), p-PDK1 (S241), S6, p-S6(S235/236), p-MEK1/2(S217/221), p-ERK1/2(T202/Y204), p-p38MAPK(T180/Y182), PP2A A Subunit(81G5), p110α and p110β (Cell Signaling Technology).

p-PDK1 (S410) (Abcam), β-catenin and PDK1 (BD Biosciences), and anti-PP2A B subunit (B55) (Upstate Biotechnology); HA(SC-805) and β-Actin (Santa Cruz Biotech) and Myc (9E10) (Sigma-Aldrich).

Example 6

Experimental Procedures—Cell Viability, Senescence, and BrdU Incorporation

Cell viability was measured using CellTiter-Glo™ Luminescent Cell Viability Assay (Promega).

In brief, 1000 cells were seeded in 96-well plate and the cell number was measured following manufacturer's instruction. To detect the senescence in DLD1-tet on cells, cells were treated with Dox for 48 hr and SA-β-Gal staining was performed according to the protocol of Senescence Detection kit (BioVision). Cell cycle analysis was done by DNA content quantification.

The cells were fixed with 70% ethanol and stained with propidium iodide (50 µg/ml) staining. The stained cells were analyzed by FACScalibur (BD Bioscience) and quantified by using CellQuest software (BD bioscience).

For BrdU incorporation assay, cells were treated as above and incubated with BrdU reagent for 5 hours before harvesting. Cells were fixed and stained with the BrdU antibody and 7-AAD according to the manufacture's protocol (BD Bioscience). Stained cells were analyzed by FACScalibur (BD Bioscience) and quantified by using CellQuest software (BD Bioscience).

Example 7

Experimental Procedures—RNA Interference

Specific siRNA oligos targeting Myc, p70S6K, PPP2R1A, AKT1, PIK3CA, PDK1, mTOR, raptor and rictor mRNAs were described previously (Cappellen et al., 2007; Heinonen et al., 2008; Sablina et al., 2007; Sarbassov et al., 2005; Vasudevan et al., 2009) and listed in Table S3. PIK3CB siRNA was purchased from Santa Cruz Biotech.

The SMARTpool® siRNA targeting PPP2R2B and the non-targeting control were purchased from Dharmacon (Lafayett, Colo.). A separate PPP2R2B siRNA targeting the following sequence: 5'-GCUUACUUUCUUCUGUCUA-3' (SEQ ID NO: 15) was obtained from Sigma-Proligo.

Cells were transfected with 100 nM final concentration of siRNA duplexes using Lipofectamine RNAiMAX (Invitrogen) following the manufacturer's instructions.

Example 8

Experimental Procedures—Anchorage-Independent Colony Formation Assay

For DLD1 and HCT116 inducible cells foci formation assay, $1 \times 10^4$ cells were seeded on 6-well plate with or without treatment with Dox or rapamcycin. Cells were grown for 2 weeks and the surviving colonies were stained with gentian violet after methanol fixation, and visible colonies (>50 cells) were counted.

For anchorage-independent growth, cells were suspended in DMEM containing 0.3% agar, 10% fetal bovine serum, and layered on DMEM containing 0.6% agar, 10% FBS and 1.0

μg/ml doxycycline in 6-well plate. After 4 weeks, colonies were stained with iodonitrotetrozolium chloride (Sigma) for overnight.

Colonies from randomly-selected image areas of three replicate wells were enumerated.

Example 9

Experimental Procedures—Co-Immunoprecipitation

For immunoprecipitation analysis, 293T cells were transiently transfected with HA-PDK1 and PPP2R2B-Myc by using Fugen HD (Roche). At 48 hr post-tranfection, the cells were lysed and immunoprecipitated with antibodies for HA-tag (SC-805, Santa, Cruz) and Myc-tag (9E10, Roche).

To study direct interaction between PPP2R2B-Myc and endogenous PDK1, DLD1-PPP2R2B cells were treated with Dox for 24 h and cells were lysed and immunoprecipitated with anti-PDK1 and anti-Myc-tag.

Example 10

Experimental Procedures—Confocal Analysis

The cells were seeded on the glass slides in 12 well plate. After treatment with Dox for 48 hrs; cells were fixed with 3.7% paraformaldehyde in PBS and permeablized with 0.2% Triton-X100.

Cells were sequentially incubated with primary antibodies (anti-Myc or anti-p-PDK1(S241) and Alexa Fluor 488 or Alexa Fluor 546-conjugated secondary antibodies (Invitrogen) for 1 hour each and DAPI for nuclear staining for 15 mins.

They were then mounted in Fluorsave (CalBiochem) mounting medium. The stained cells were examined by Zeiss LSM510 confocal microscopy.

Example 11

Experimental Procedures—Protein Phosphatase Activity

For phosphatase assays, DLD1-PPP2R2B or DLD1 control cells were suspended in lysis buffer (50 mM Tris-HCl, pH 7.4, 7.5% Glycerol, 1 mM EDTA, 150 mM NaCl, 0.5% NP-40, 1 mM $Na_3VO_4$, Complete Protease Inhibitor), cleared from debris by centrifugation, incubated with c-Myc (9E10, Roche Inc.) followed by incubation with Anti-Mouse IgG Beads (Roche).

The beads were resuspended in PP2A phosphatase reaction buffer and analyzed for PP2A activity using Serine/Threonine Phosphatase Assay kit (Upstate) according to the manufacturer's specifications. Fluorescence was measured using a fluorescence microplate reader (Sunrise, Tecan).

Example 12

Experimental Procedures—Mouse Xenografts and Drug Treatment

The female athymice BALB/c nude mice (5-8 week-old) were housed in the Biological Resource Centre. Mice were implanted subcutaneously in both sides of flank with $3\times10^6$ DLD1-PPP2R2B or control DLD1 cells, respectively.

When tumors reached ~70 $mm^3$, the mice were divided two groups (6 mice per group) and the Doxycyclin was administrated by oral gavages at 100 mg/kg daily. Tumor progress was monitored with whole body weight and tumor size for every other day. For combination treatment with rapamycin and doxycycline, the same dose of doxycyclin was given at every other day and rapamycin was administered by intraperitoneal injection at 4 mg/kg at Day 3, 5, 7 and 11.

Tumor diameters were measured every 3-4 days with caliper and tumor volumes were calculated from 7-9 mice per data time point. All animal work was performed in accordance with animal experiments guidelines of Singapore.

Example 13

Loss of PPP2R2B Expression by DNA Hypermethylation in CRC

Given the low frequency of mutations found in PP2A family members in human malignance, including CRC, we sought to determine whether they are epigenetically inactivated in CRC.

Through interrogating expression data of a series of CRC cell lines we published previously (Jiang et al., 2008), we found PPP2R2B, encoding B55β, is the only subunit that is consistently downregulated or silenced in all examined CRC cell lines, but not in the normal colon mucosa sample (Table S1).

Figure 1B:
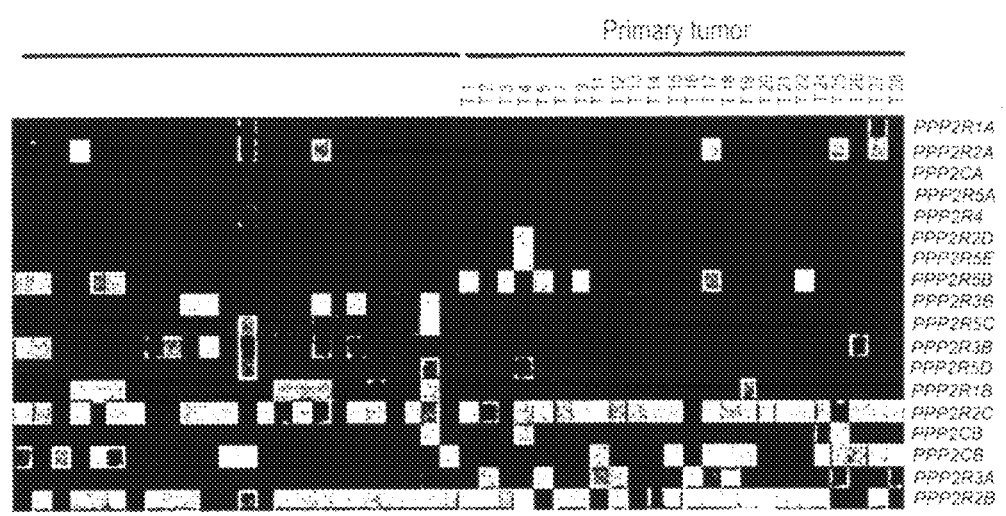

The significant downregulation of PPP2R2B was further validated using gene expression array data of 24 pairs of patient-derived CRC tumors and matched normal mucosa controls ($p<0.01$, FIG. 1A), and this appeared to occur in >90% of CRC samples (FIG. 1B and Table S2).

Figure 1C:
Figure 1D:
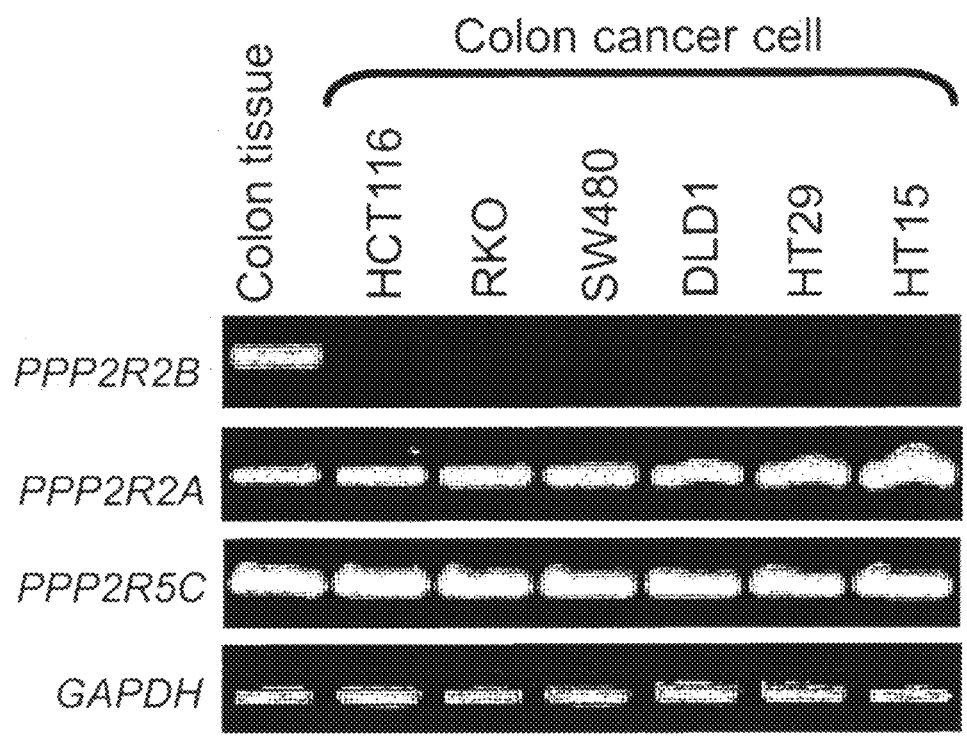

RT-PCR analysis confirmed the PPP2R2B downregulation in 6 randomly-selected CRC and matched controls, as well as in a series of CRC cells lines (FIG. 1C and FIG. 1D). By contrast, PPP2R2A, or PPP2R5C which has been previously reported to be downregulated in lung cancer (Chen et al., 2004), were not found to be downregulated in CRC.

Figure 1E:
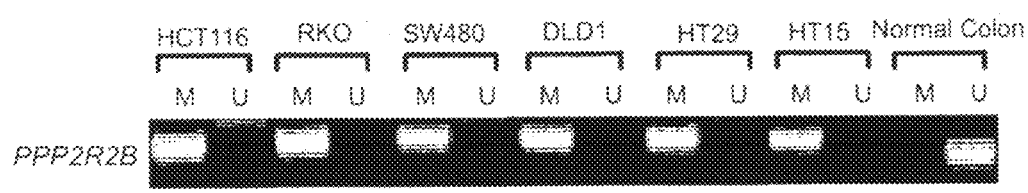
Figure 1F:
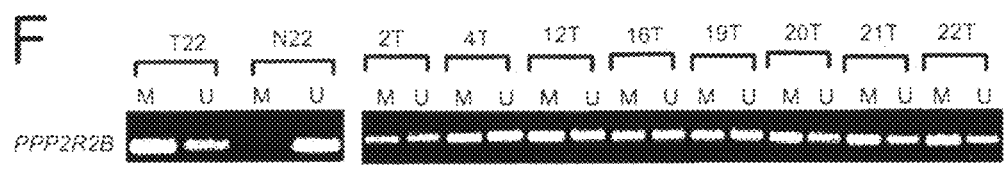

We next determined whether the loss of PPP2R2B expression in CRC is associated with promoter DNA hypermethylation. Methylation-specific PCR (MSP) analysis revealed a hypermethylated PPP2R2B promoter in CRC cell lines, as well as in all 8 examined CRC tumor samples, but not in their matched normal controls (FIG. 1E).

Figure 1G:
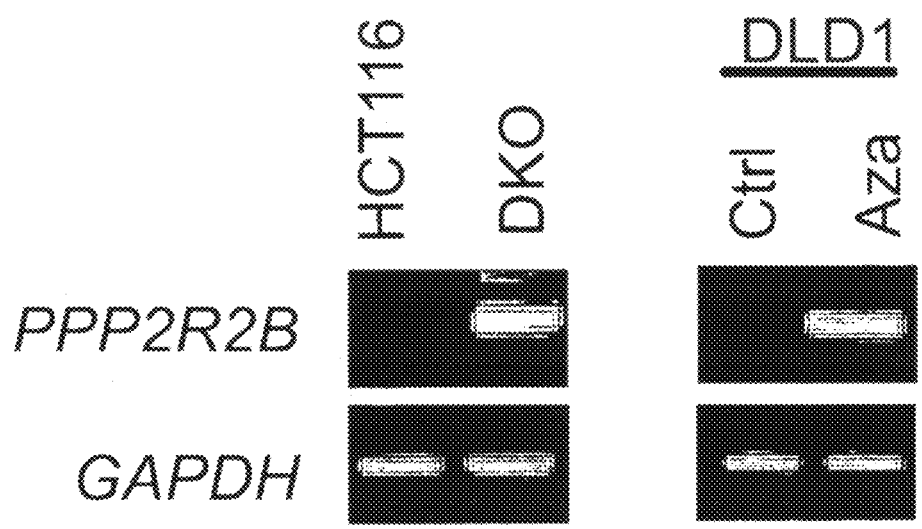
Figure 1H:
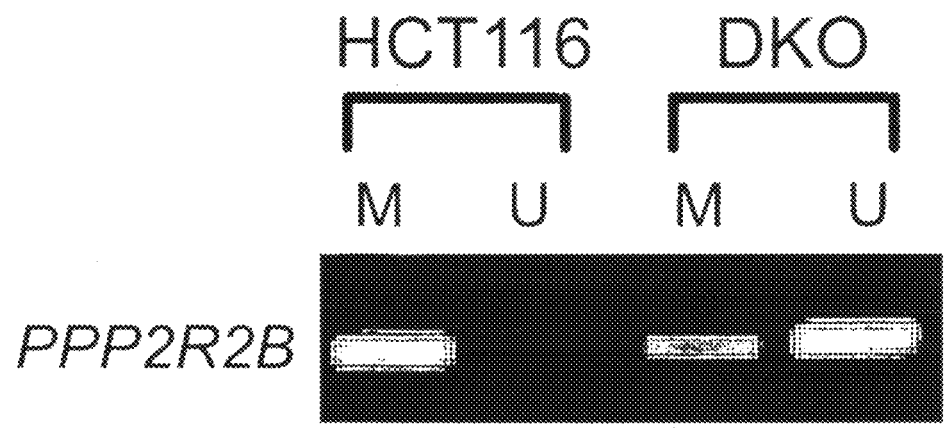
Figure 1I:
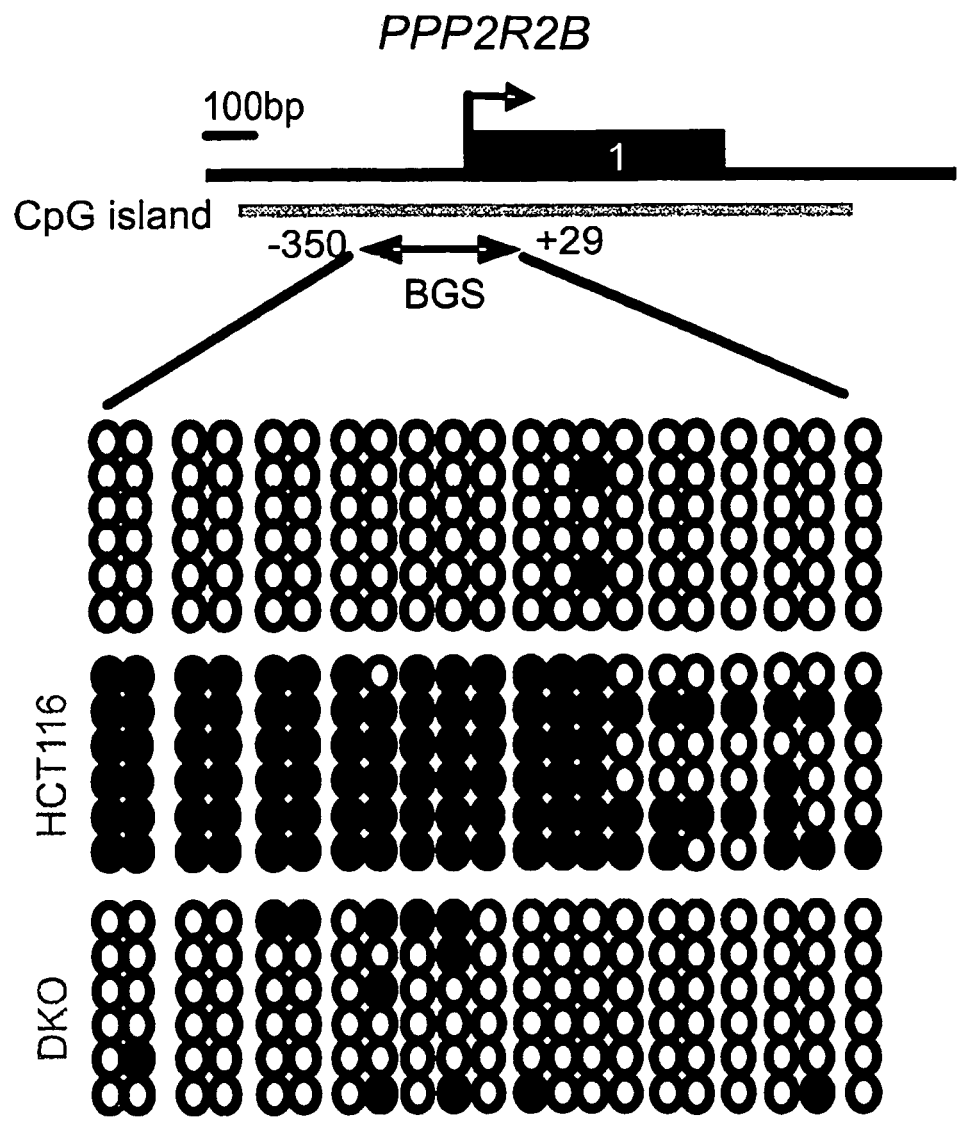

Furthermore, HCT116 cells deleted of both DNMT1 and DNMT3B (DKO) or DLD1 cells treated with 5-aza-dC exhibited re-expression of PPP2R2B (FIG. 1G), correlated with a demethylated PPP2R2B promoter in DKO, as demonstrated by both MSP and bisulfate genomic sequencing (FIG. 1H and FIG. 1I).

Figure 8:
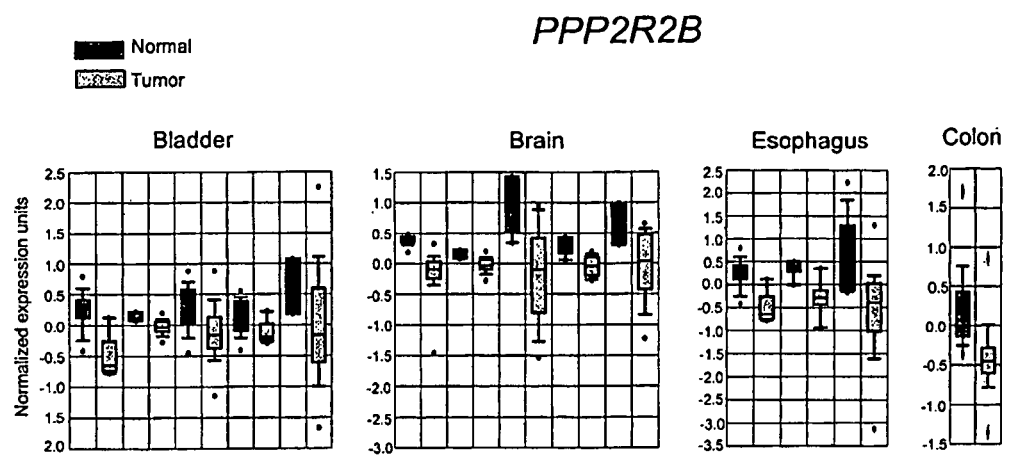
FIG. 8. PPP2R2B is significantly suppressed in multiple human cancers. ONCOMINE data analysis showing the normalized expression of PPP2R2B in malignant and corresponding normal tissues of bladder (Dyrskjot et al., 2004; Sanchez-Carbayo et al., 2006), brain (Rickman et al., 2001; Shai et al., 2003; Sun et al., 2006), esophagus (Wang et al., 2006) and colon (Ki et al., 2007). Representative data are shown across multiple independently published microarray studies from the ONCOMINE website.

Taken together, these results demonstrate that PPP2R2B is epigenetically lost in CRC through promoter DNA hypermethylation. Moreover, Oncomine data mining reveals that. PPP2R2B is also significantly downregulated in other human cancers, such as bladder, brain and esophagus carcinoma (FIG. 8).

Example 14

PPP2R2B Re-Expression in CRC Cells Results in Senescence, Decreased Cell Proliferation, and Xenograft Tumor Growth Inhibition Loss of PPP2R2B expression in cancer suggests it normally functions as a tumor suppressor. To investigate this possibility, we established stable DLD1 and HCT116 cell lines with doxycycline (Dox) inducible expression of a Myc-tagged PPP2R2B, designated as DLD1-PPP2R2B or HCT116-PPP2R2B.

Figure 2A:
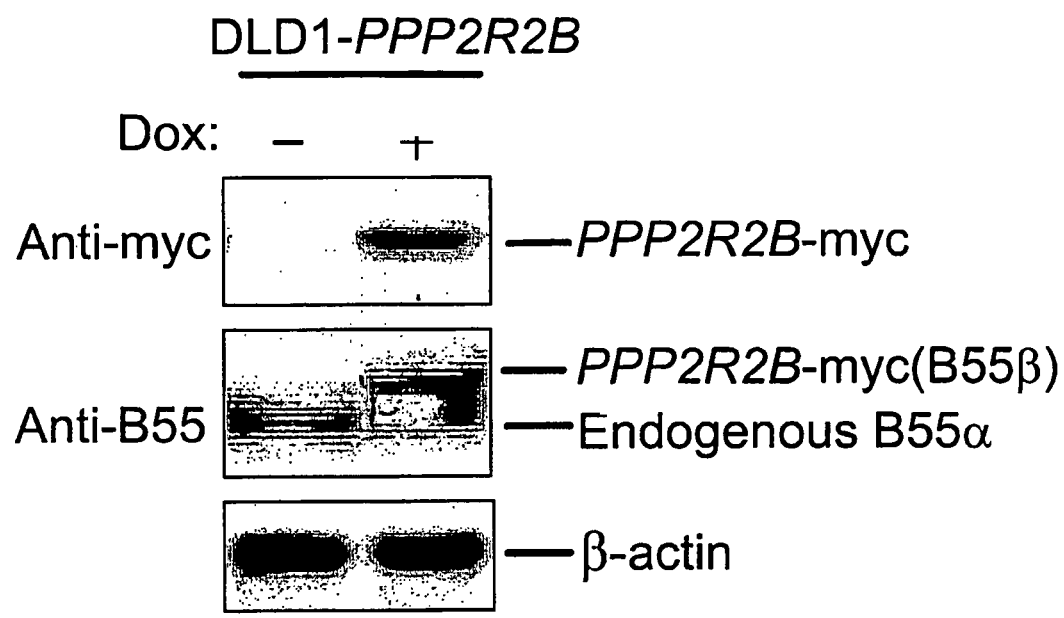
FIGS. 2A-2G. Gain- or loss-of-function analysis of PPP2R2B as a tumor suppressor FIGS. 2A. Immunoblot analysis of DLD1-PPP2R2B cells on endogenous B55α and ectopic B55β-Myc, using anti-Myc tag or anti-B55 subunit antibody. Cells were treated with or without 1.0 μg/ml Doxycycline (Dox) for 3 days.

As shown in DLD1-PPP2R2B cells, addition of Dox for 3 days resulted in PPP2R2B-Myc (B55β-Myc) expression in a level comparable to that of the endogenous B55α, as detected by an antibody recognizing B55α/β subunits (FIG. 2A). Furthermore, RT-PCR analysis shows that the expression level of PPP2R2B mRNA after Dox treatment in DLD1-PPP2R2B cells was similar to that in the normal colon tissue (data not shown).

Figure 2B:
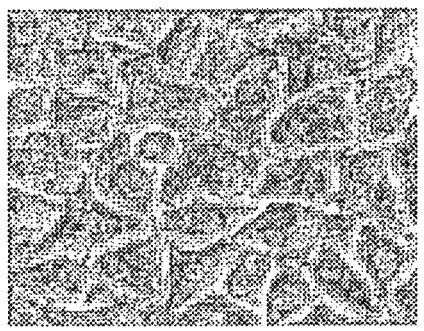
Figure 2B:
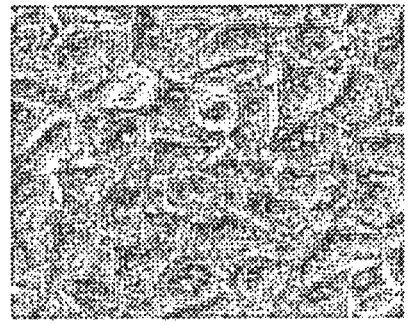
Figure 2B:
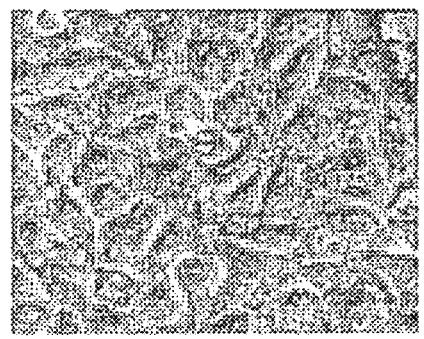
Figure 2B:

Thus, PPP2R2B-Myc is induced in CRC cells in a level that is physiologically relevant. Under this condition, restored expression of PPP2R2B resulted in a typical senescence phenotype, including enlarged and flattened cell morphology, as well as increased senescence-associated β-galactosidase (SA-β-Gal) (FIG. 2B).

Figure 2C:
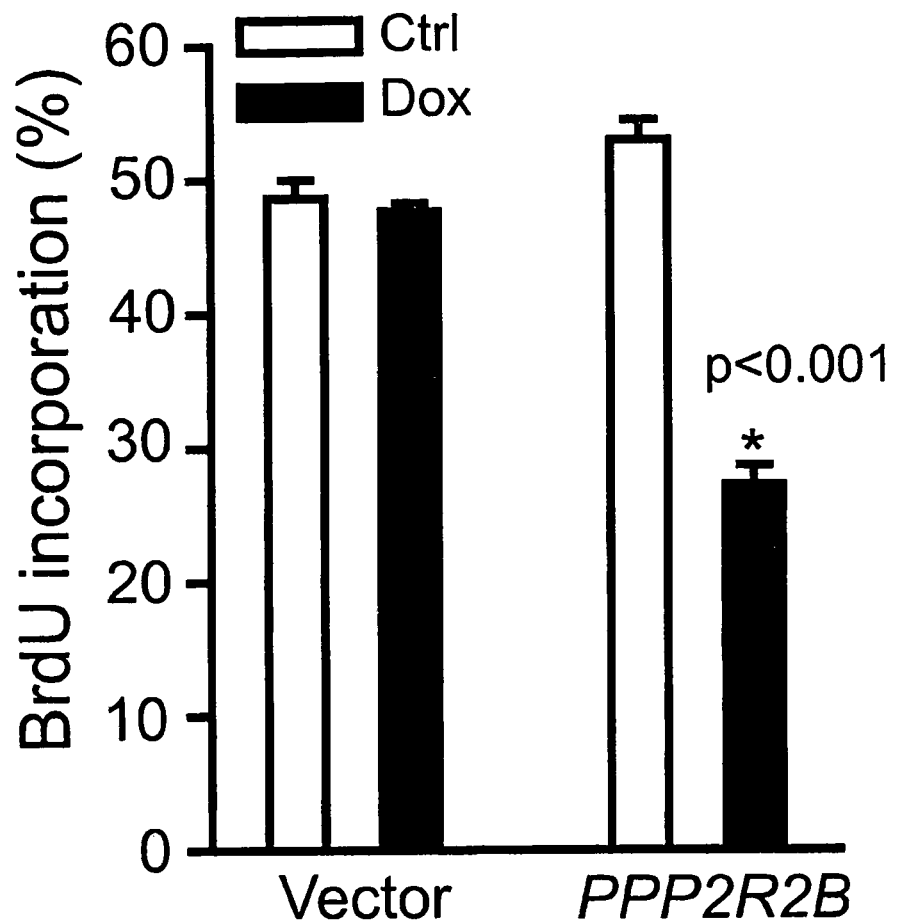
Figure 2D:
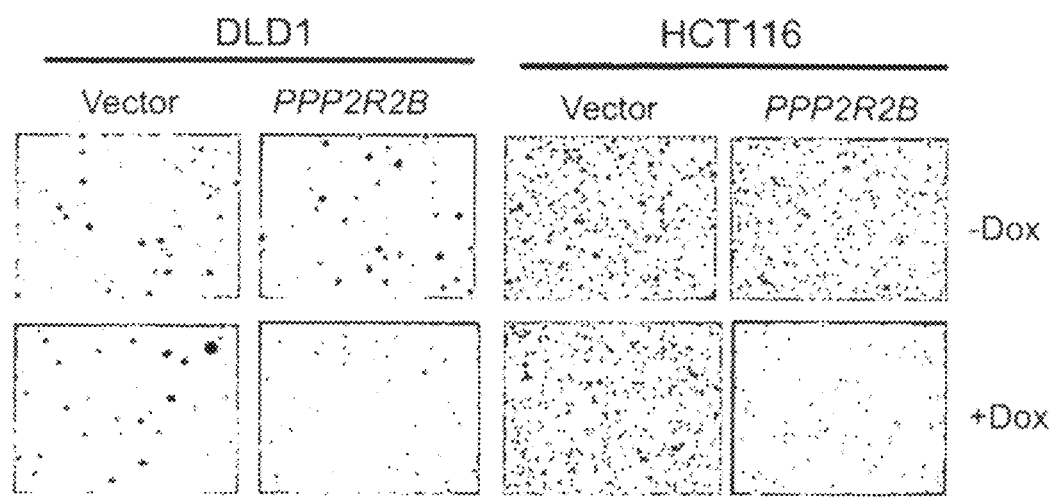

Accordingly, DNA synthesis as measured by BrdU incorporation decreased markedly following PPP2R2B expression by Dox (FIG. 2C), indicative of inhibition of cell proliferation. Furthermore, PPP2R2B restoration caused a strong inhibition of anchorage-independent growth in soft agar (FIG. 2D).

The strong growth inhibitory effect of PPP2R2B was further confirmed in two additional CRC cell lines by using retroviral transduction of both GFP and PPP2R2B, which resulted in a similar morphological changes (FIG. 9A) and inhibition of growth in soft agar (FIG. 9B).

To assess the capacity of PPP2R2B in tumor growth inhibition in vivo, Dox-inducible DLD1 cells expressing PPP2R2B or the empty vector were subcutaneously injected into nude mice and the formed tumor growth was monitored for three-weeks with or without daily Dox treatment.

Figure 2E:
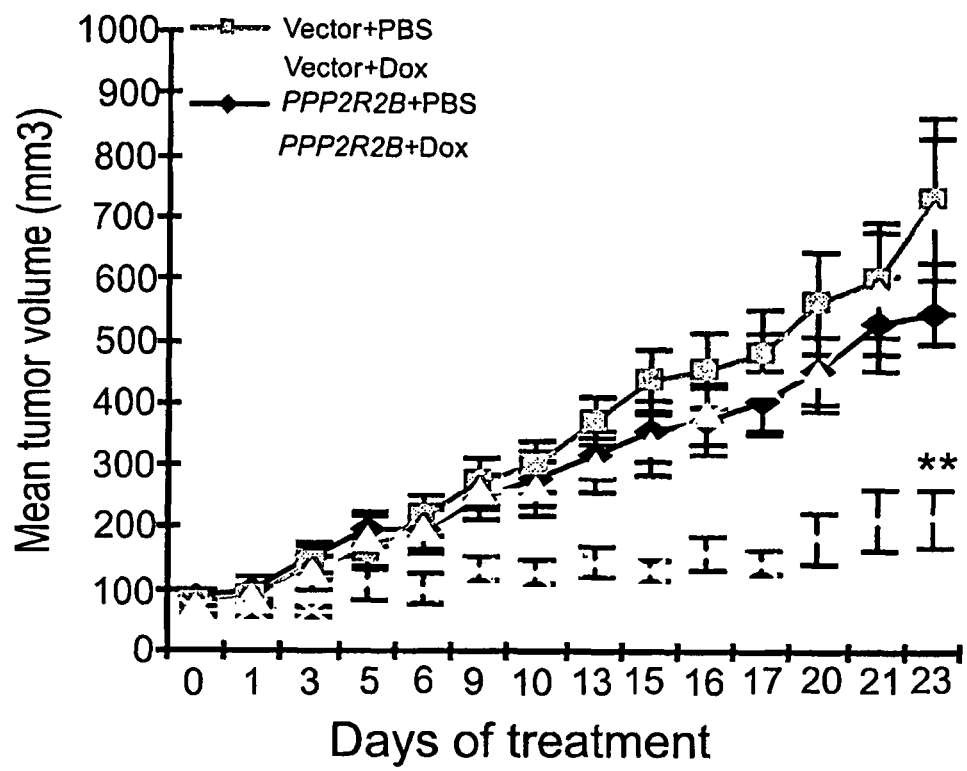

The data showed that the tumor growth derived from DLD1-PPP2R2B cells was markedly inhibited in mice treated with Dox, whereas the tumor growth from the DLD1 cells expressing the control vector was unaffected by Dox treatment (FIG. 2E). Thus, this result validated the growth inhibitory activity of PPP2R2B in a xenograft mouse model.

Example 15

PPP2R2B Knockdown Promotes Cell Transformation

We next addressed whether ablation of PPP2R2B is sufficient to promote cell transformation in immortalized human embryonic kidney (HEK) fibroblasts expressing hTERT and oncogenic Ras (HEK-TERV).

Figure 2F:
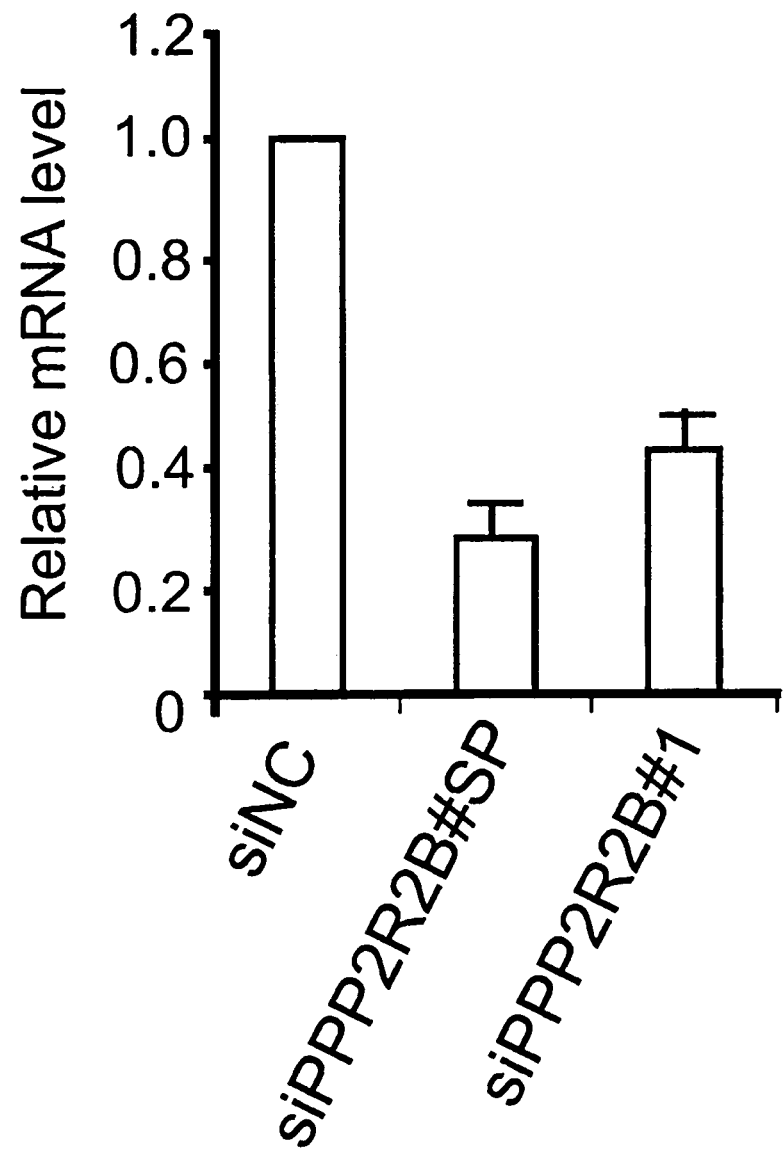
Figure 2G:
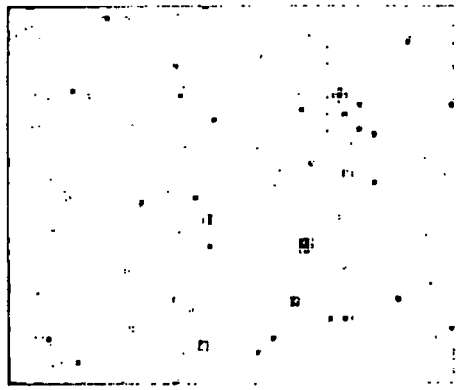
Figure 2G:
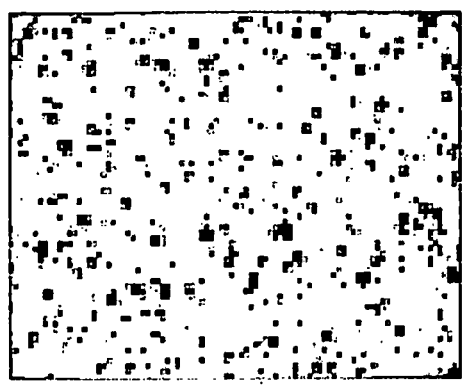
Figure 2G:
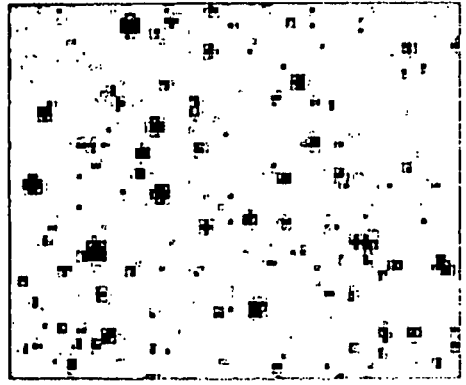
Figure 2G:
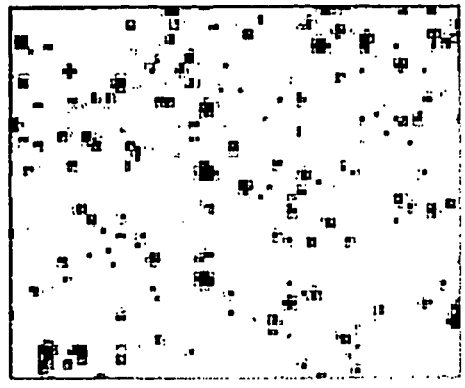

In this previously well-characterized transformation model, inhibition of PP2A by overexpression of small T antigen results in efficient transformation (Chen et al., 2004; Hahn et al., 2002; Sontag et al., 1993). Small interfering RNA (siRNA)-directed knockdown by targeting different regions of PPP2R2B mRNA resulted in enormous increase in anchorage-independent growth of HEK-TERV cells in a similar efficiency as that observed with overexpression of small T antigen (FIG. 2F and FIG. 2G).

On the basis of both of the gain- and loss-of-function data, we propose that PPP2R2B functions as a tumor suppressor and the loss of which facilitates oncogenic transformation.

Example 16

PPP2R2B-Associated PP2A Complex Modulates Phosphorylation of Myc and P70s6k in CRC Cells The PP2A B regulatory subunits guide the substrate specificity towards the dephosphorylation events in a cell and context-dependent manner (Virshup and Shenolikar, 2009). Several oncogenic proteins, including AKT, p70S6K, mTOR, β-catenin and Myc, have been previously identified to be the substrates of PP2A in various cell systems (Andrabi et al., 2007; Arnold and Sears, 2008; Peterson et al., 1999; Seeling et al., 1999; Yeh et al., 2004).

Figure 3A:
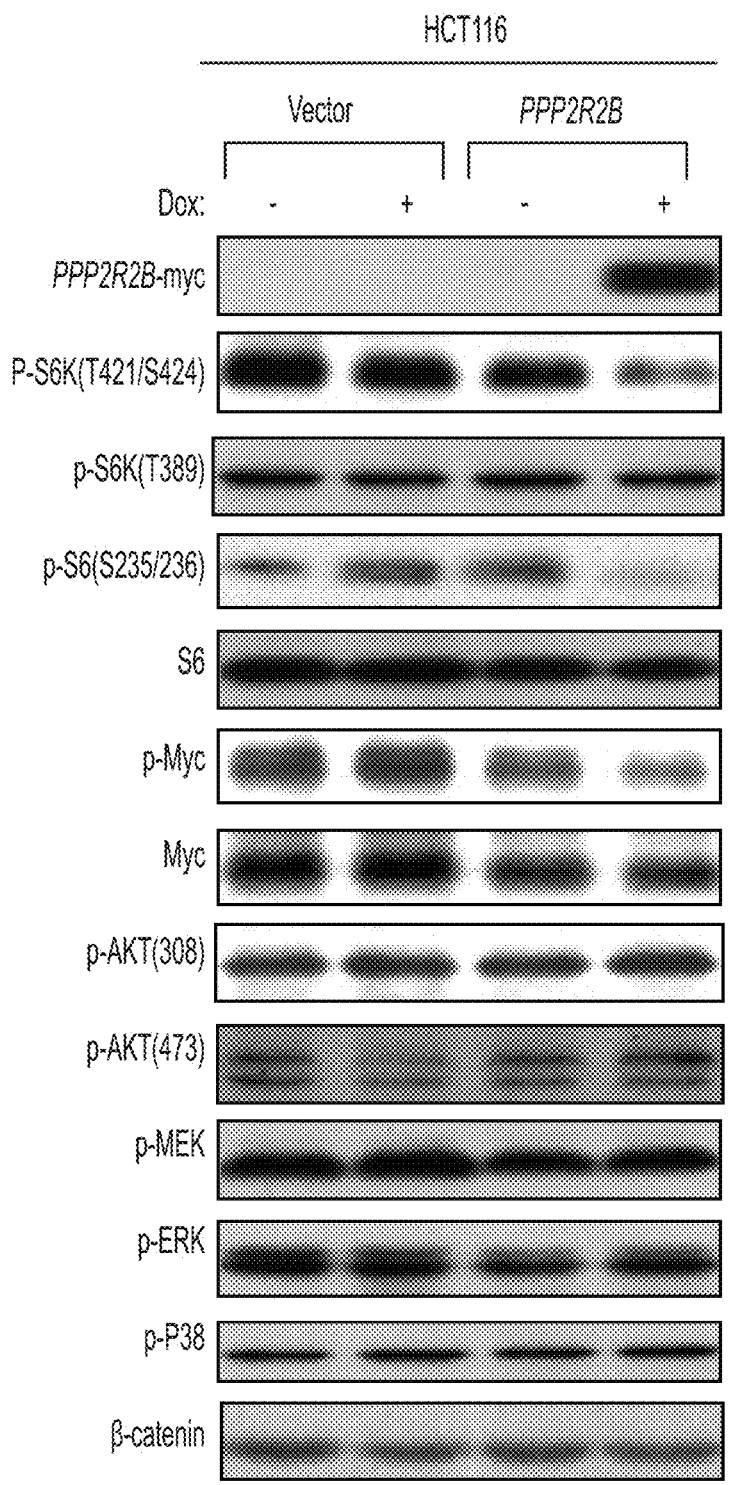
FIGS. 3A-3G. Restoration of PPP2R2B-PP2A complex results in inhibition of p70S6K and Myc phosphorylation FIG. 3A. Immunoblot analysis of HCT116-PPP2R2B or the vector control cells for indicated proteins in the presence or absence of Dox for 48 hr.

To dissect out the possible mechanisms responsible for the growth inhibitory effect of PPP2R2B, we began with the HCT116-PPP2R2B cells to probe several oncogenic signaling pathways known to be important in CRC that might be affected by PP2A (FIG. 3A). The analysis led to the identification of two phosphorylation events that are inhibited by PPP2R2B re-expression following Dox treatment.

The first one is phosphorylation of p70S6K. Using phosphorylation specific antibodies, we show that the phosphorylation at T421/S424 was markedly reduced upon PPP2R2B re-expression, whereas the phosphorylation at T389 appeared to be unaffected, suggesting a site-specific modulation of p70S6K by PPP2R2B.

The second one is c-Myc phosphorylation, as detected by using a phosphor-Myc antibody specific for T58/S62, which was also downregulated upon PPP2R2B re-expression. The other examined oncogenic signals, such as p-AKT, p-ERK, β-catenin and p-p38 were not noticeably affected by PPP2R2B re-expression (FIG. 3A).

Figure 3B:
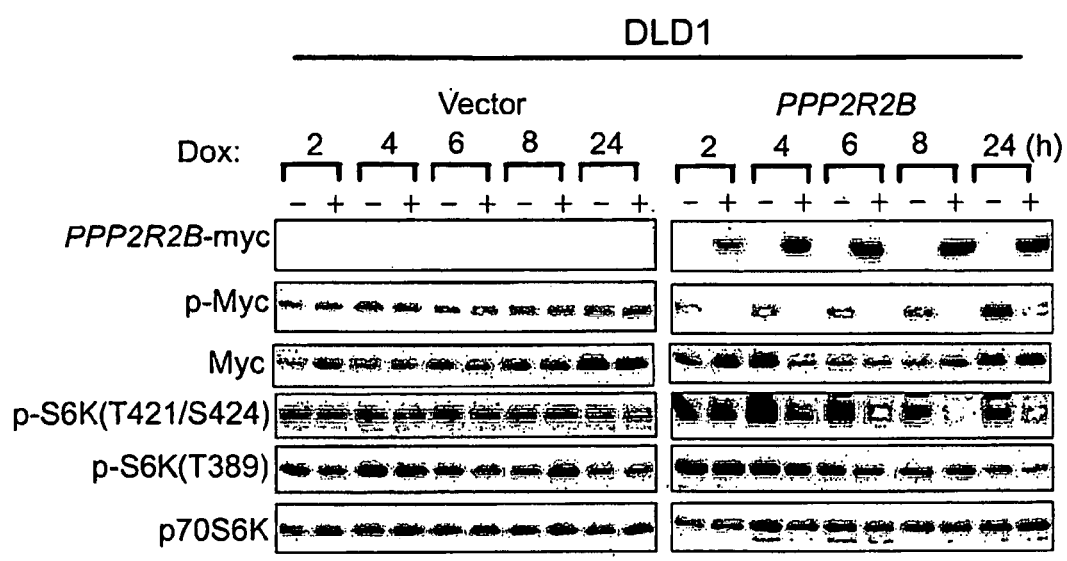

The effects of PPP2R2B on p70S6K and c-Myc (thereafter referred as Myc) were further confirmed in DLD1 cells in a time-course analysis (FIG. 3B). The data showed that Dox induction of PPP2R2B expression resulted in a rapid dephosphorylation of Myc and p70S6K (T421/S424, but not T389) in relative to the total p70S6K and Myc protein levels, suggesting that these changes are early effect of PPP2R2B and unlikely to be the secondary effect of growth inhibition.

Figure 3C:
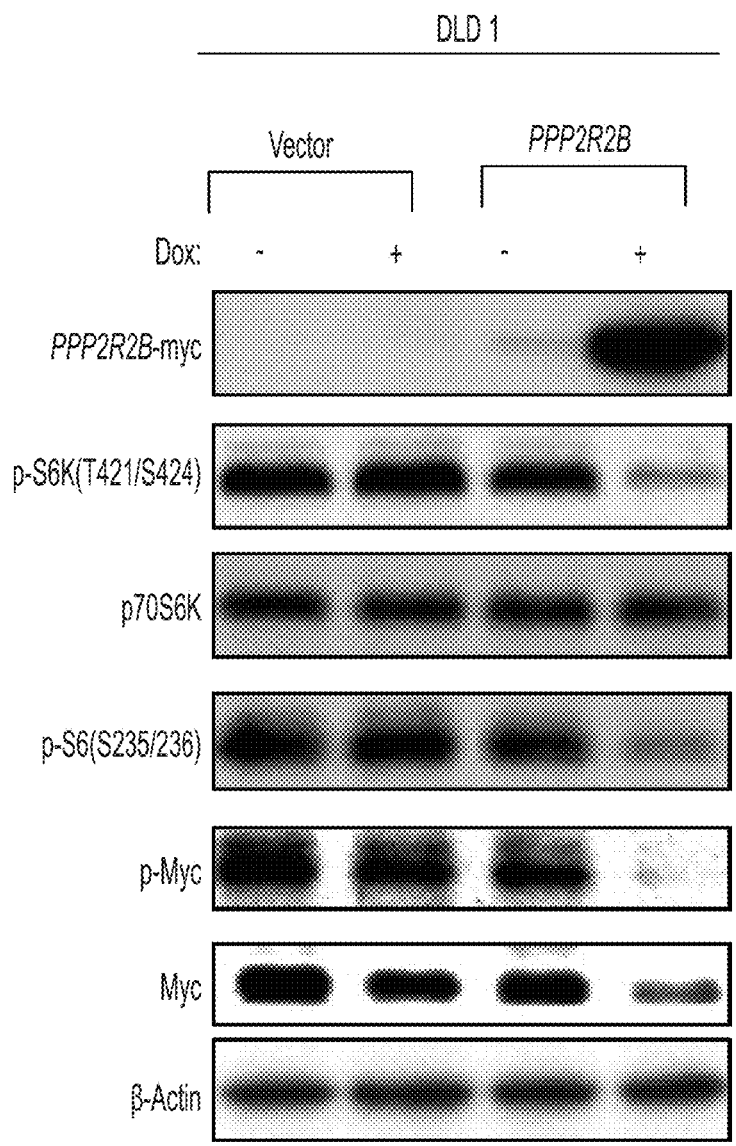
Figure 10A:
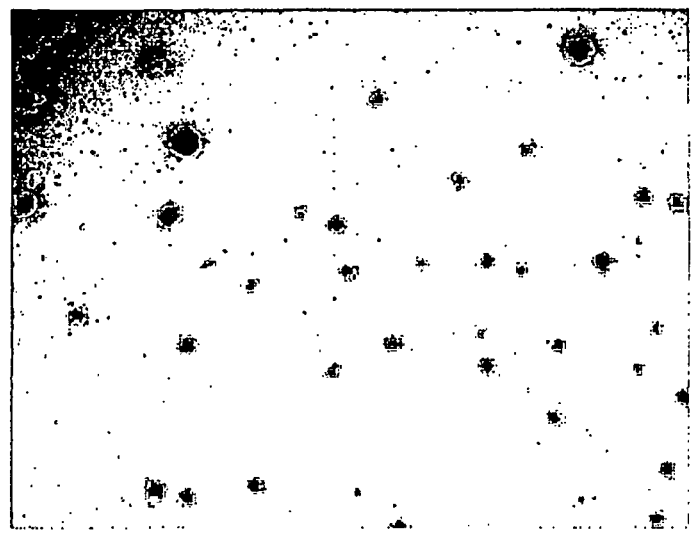
FIGS. 10A-10B. Ectopic expression of PPP2R2B inhibits the growth of NIH/3T3 cells transformed with Ras.
Figure 10A:
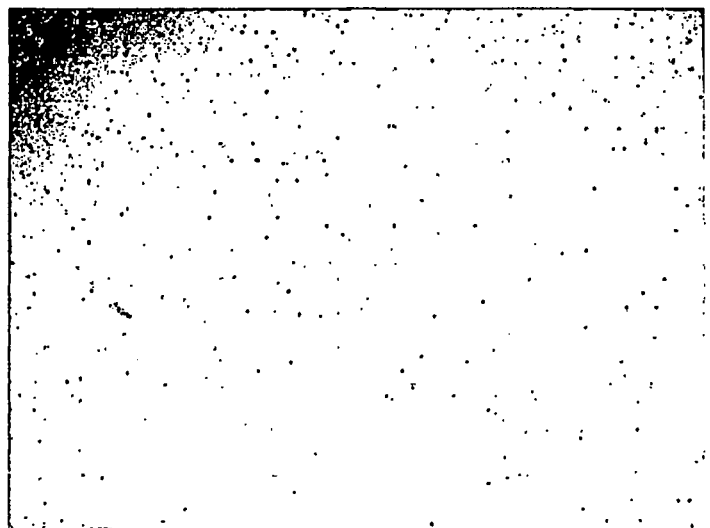
Figure 10B:
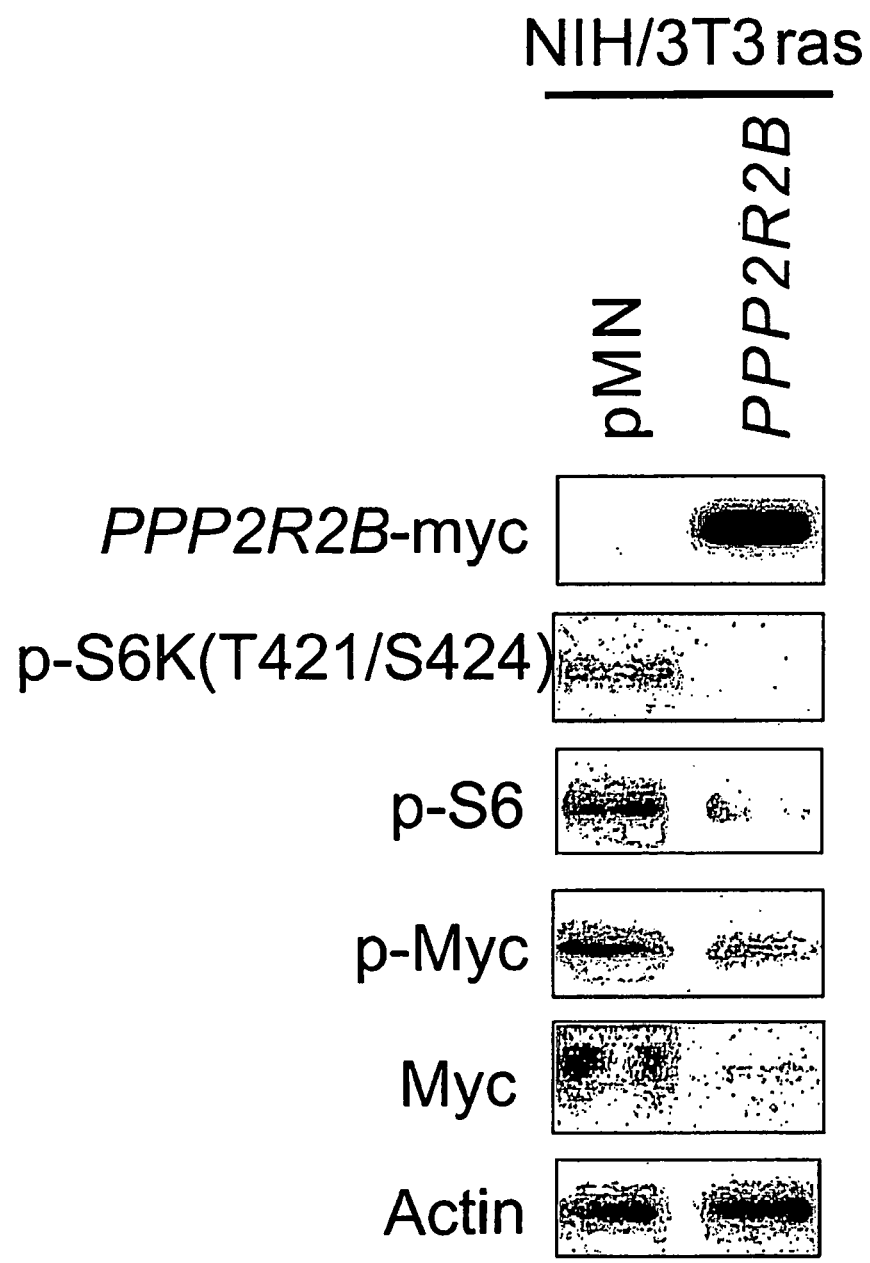

The decreased Myc phosphosphorylation eventually resulted in less protein accumulation by 48 h of Dox treatment (FIG. 3C), which is consistent with the previous finding that increased Myc phosphorylation at S62 correlates with Myc protein accumulation (Arnold and Sears, 2006; Junttila et al., 2007; Yeh et al., 2004). Thus, p70S6K and Myc are two downstream signals affected by PPP2R2B-PP2A complex, while no marked differences were observed in the expression or phosphorylation status of other oncogenic signaling pathways known to be important in colon cancer. We also confirmed the inhibitory effect of PPP2R2B expression on cell growth, phosphorylation of Myc and p70S6K in NIH-3T3-Ras transformed cells (FIG. 10A and FIG. 10B).

Of notice, PPP2R2B re-expression had no effect on AKT T308 phosphorylation, which is known to be targeted by PP2A/B55α or B56β complex in NIH3T3 cells (Kuo et al., 2008; Padmanabhan et al., 2009), neither on β-catenin phosphorylation which is a target of PP2Aα in CRC (Su et al., 2008). In addition, in human mammary epithelial cell cells, SV40 small t antigen(ST)-mediated PP2A inhibition is associated with increased AKT S473 phosphorylation and the mTOR-mediated p70S6K T389 phosphorylation (Andrabi et al., 2007; Chen et al., 2005; Zhao et al., 2003), and these changes were not seen here in this cellular context. These findings are consistent with the substrate specificity of different PP2A/B subunits in a tissue specific manner and show that PPP2R2B-associated PP2A complex (PP2A-B55β) distinguishes from the other PP2A complexes by affecting different downstream substrates.

Figure 3D:
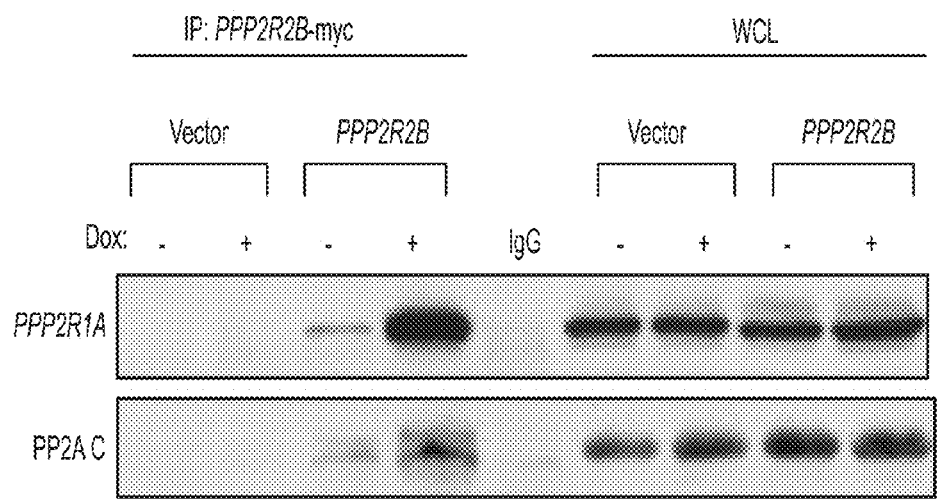
Figure 3E:
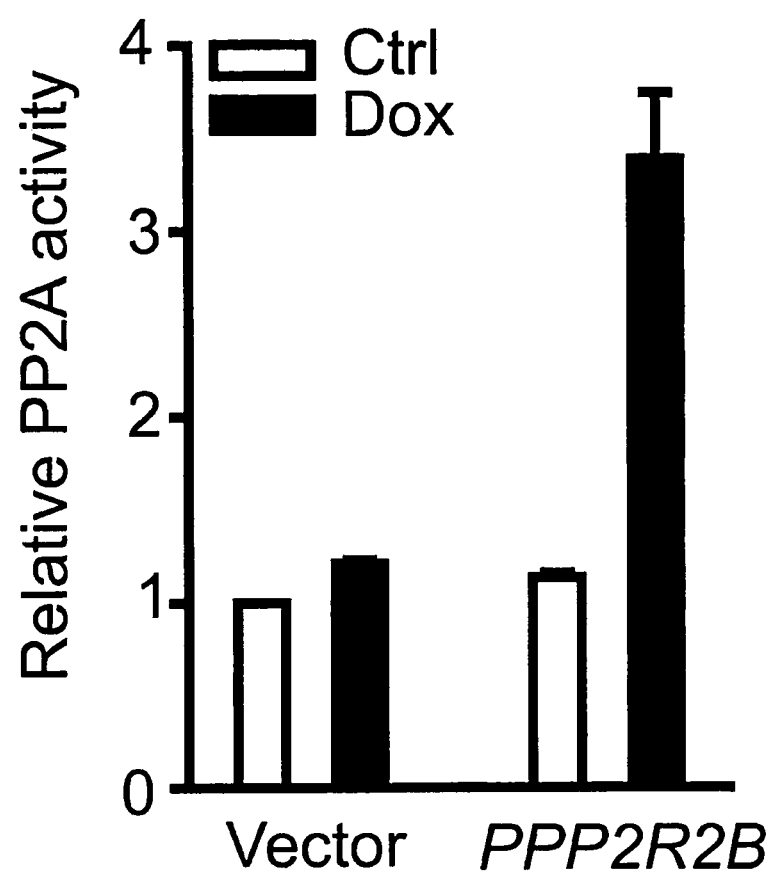

To demonstrate that ectopic PPP2R2B in fact interacts with other PP2A subunits to form an active PP2A complex, we performed the co-immunoprecipitation assays to show that the PPP2R2B indeed co-immunoprecipitates with both PP2A structural (A) and catalytic (C) subunits (FIG. 3D). Furthermore, in an in vitro PP2A assay using a synthetic phosphothreonine peptide RRA(pT)VA as a substrate (Chen et al., 2004), the immunoprecipitates of PPP2R2B from Dox-treated DLD1-PPP2R2B cells clearly displayed increased PP2A activity compared to the controls (FIG. 3E), validating that PPP2R2B re-expression restored the loss of the associated PP2A activity in CRC cells.

Figure 3F:
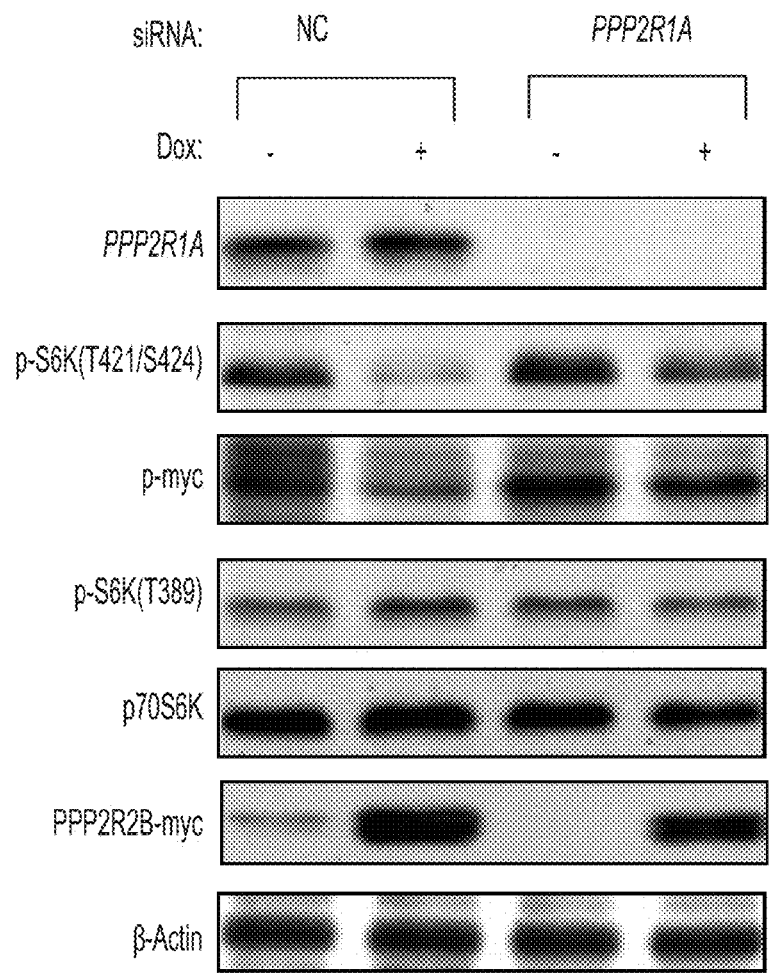
Figure 11A:
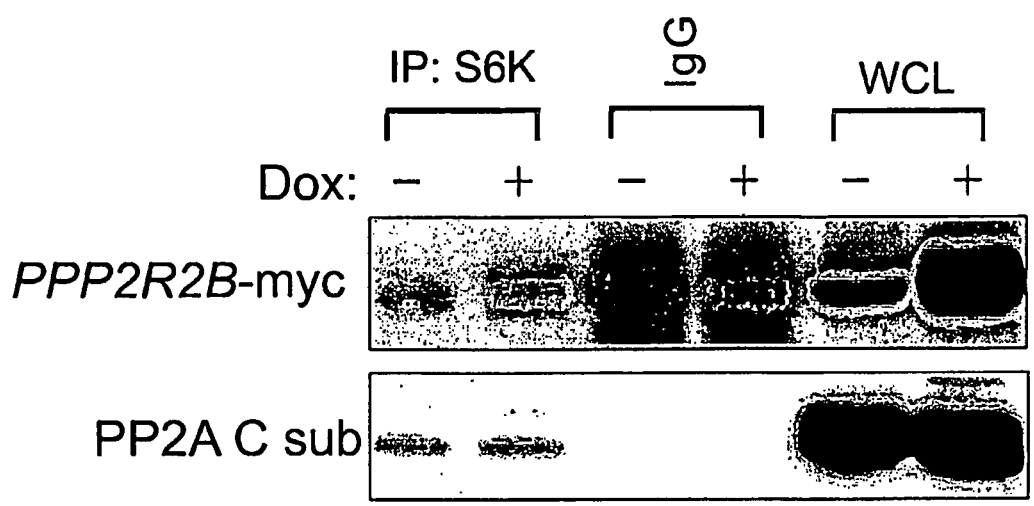
FIGS. 11A-11B. S6K interacts with PPP2R2B-associated PP2A complex.
Figure 11B:
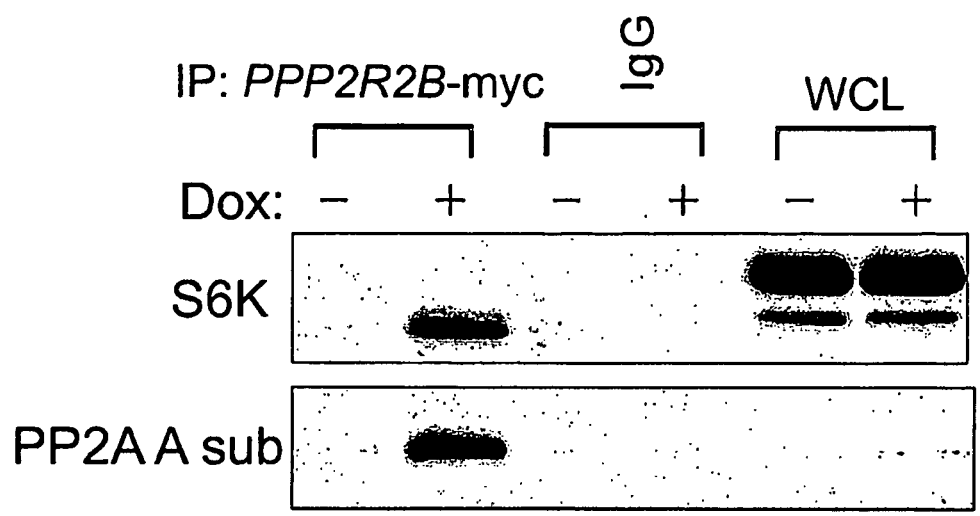

To confirm that dephosphorylation of p70S6K (T421/424) or Myc upon PPP2R2B re-expression requires PP2A activity, we depleted the A subunit of PP2A complex by siRNA in DLD1-PPP2R2B cells and found that this molecule manipulation clearly prevented the dephosphorylation of Myc and p70S6K by PPP2R2B (FIG. 3F). Together these experiments provided evidence demonstrating a functional role of PP2A-PPP2R2B complex towards modulating p70S6K and Myc phosphorylation. In addition, we have detected the p70S6K in PP2A-PPP2R2B immunoprecipitates (FIG. 11A and FIG. 11B), but we were unable to detect the physical interaction between Myc with PPP2R2B. Although another PP2A subunit B56α has been previously shown to interact and dephosphorylate Myc in HEK293 cells (Arnold and Sears, 2006; Junttila et al., 2007), PPP2R2B-PP2A complex (B55β) may modulate Myc phosphorylation indirectly in CRC cells.

Figure 3G:
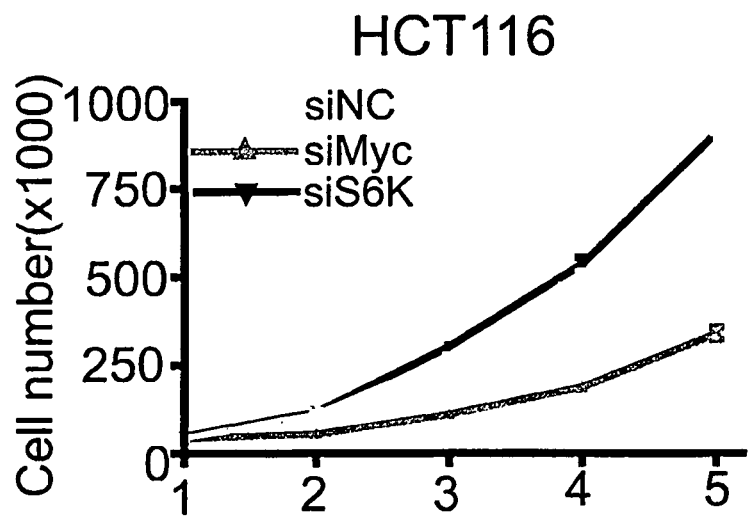
Figure 3G:
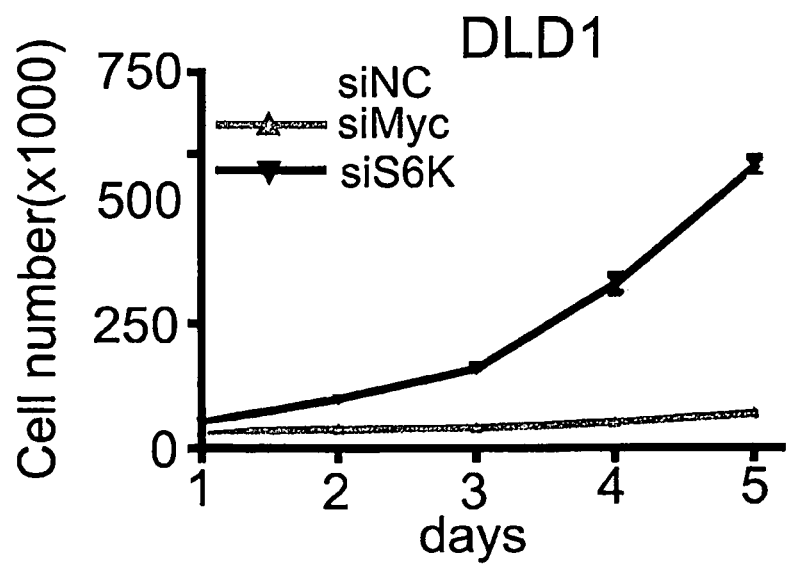

Finally, we evaluated the functional significance of Myc and p70S6K downregulation in CRC. We found that Myc knockdown strongly suppressed DLD1 cell viability, whereas p70S6K knockdown did not yield a significant effect (FIG. 3G). Thus, this data indicate a functional contribution of Myc inhibition, to the growth inhibitory effect of PPP2R2B. This is consistent with the established role of Myc in colorectal tumorigenesis (Korinek et al., 1997; Morin et al., 1997; Sansom et al., 2007).

Example 17

PPP2R2B Re-Expression Sensitizes mTORC1 Inhibitor Rapamycin

The mTOR kinase inhibitor rapamycin has a sporadic anticancer activity and its effect on mTOR downstream substrate p70S6K is often used as a surrogate marker to evaluate rapamycin response (Sawyers, 2008). The plausible connection between PPP2R2B and p70S6K signaling promoted us to investigate the possibility that PPP2R2B expression status may affect the cellular sensitivity to rapamycin.

Figure 4A:
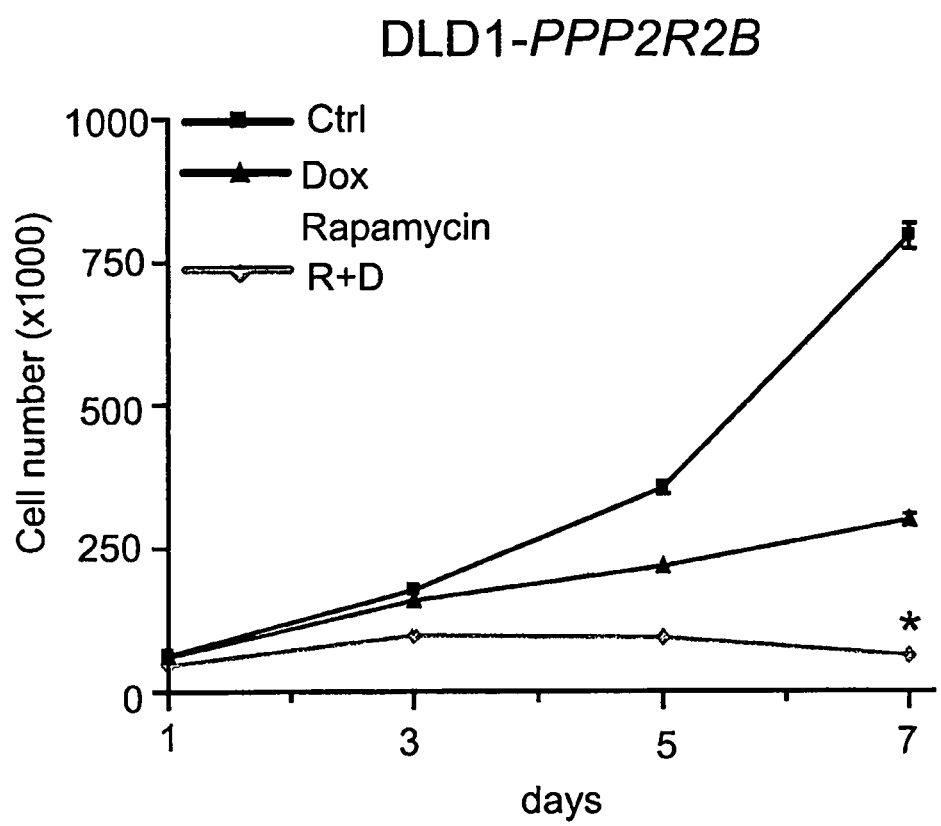
FIGS. 4A-4G. PPP2R2B re-expression in CRC sensitizes rapamycin both in vitro and in vivo, and overrides rapamycin-induced Myc phosphorylation.
Figure 4B:
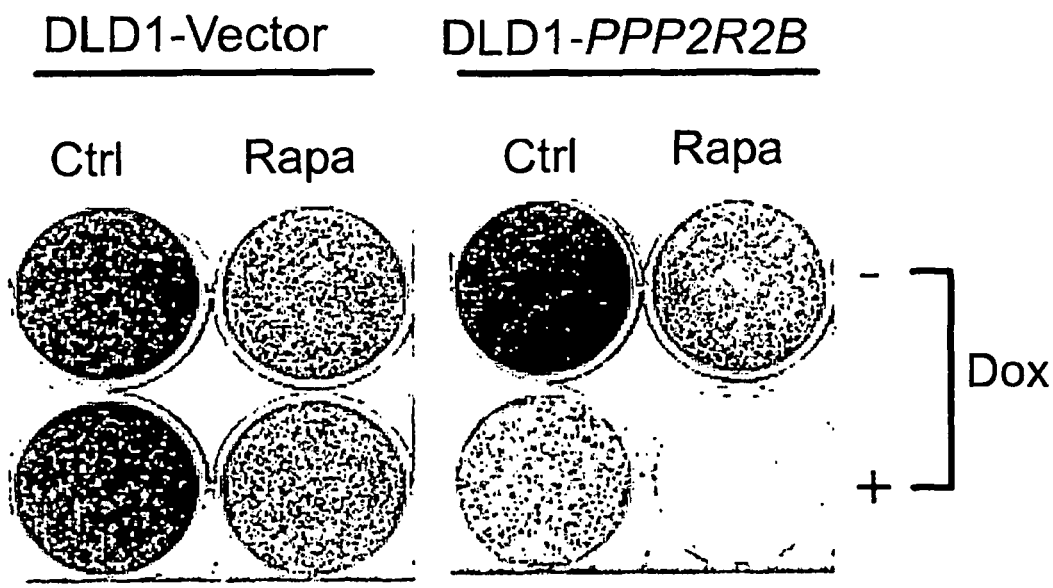
Figure 4C:
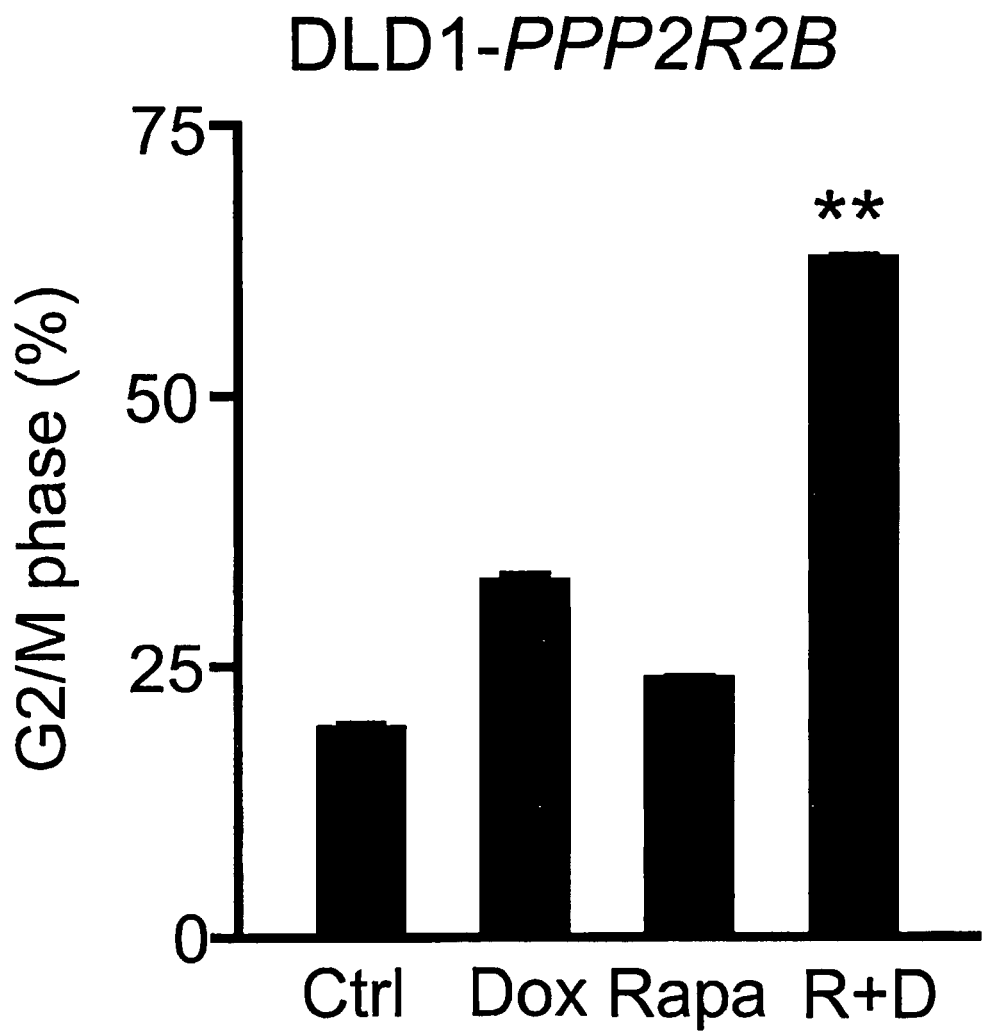
Figure 12:
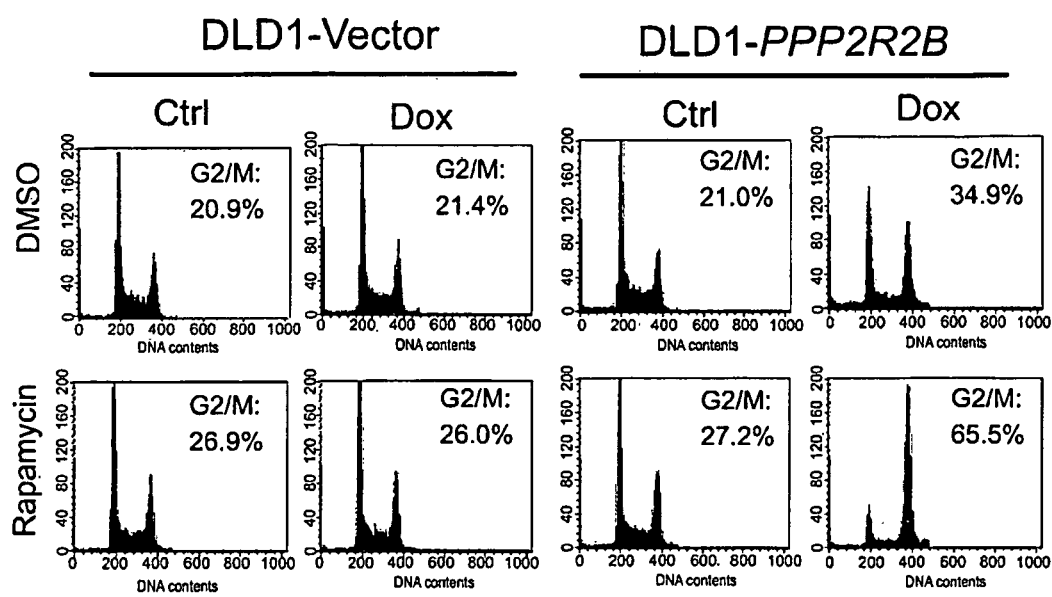
FIG. 12. PPP2R2B and rapamycin synergistically induce G2/M cell cycle arrest. FACS analysis of DLD1-PPP2R2B or vector control cells treated with Dox or rapamycin or both for 48 h. The percentages of cells arrested in G2/M are indicated.

We thus compared the effect of rapamycin on cell viability of DLD1-PPP2R2B cells in the presence or absence of Dox. The data showed that rapamycin-induced growth inhibition was much more effective when PPP2R2B was re-expressed following Dox treatment, as measured by either the cell viability assay for 5 days or the colony formation assay for 14 days (FIG. 4A and FIG. 4B). In addition, cell cycle analysis by flow cytometry shows that Dox induction of PPP2R2B expression resulted in cell cycle G2 arrest, which is further markedly augmented by adding rapamycin, indicating that PPP2R2B and rapamycin synergistically induced cell cycle arrest (FIG. 4C and FIG. 12).

Figure 4D:
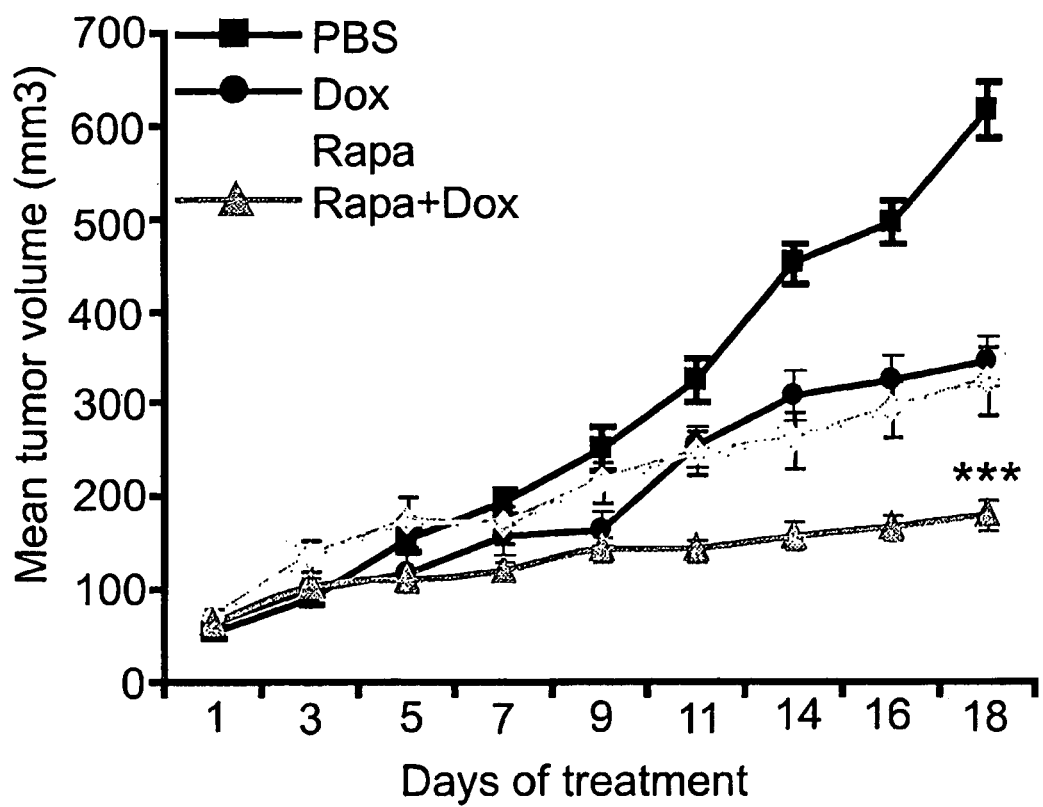

To verify the in vitro results in vivo, we studied the effects of Dox and rapamycin on the xenograft tumor growth in nude mice using DLD1-PPP2R2B and the control DLD1 cells. While the rapamycin or Dox treatment alone only moderately attenuated the tumor growth, their combination gave rise to a strong tumor growth inhibition in DLD1-PPP2R2B cells, but not in the control cells (FIG. 4D).

Collectively, these results obtained both in vitro and in vivo established that the PPP2R2B re-expression in CRC cells led to improved therapeutic effect of rapamycin. Thus, the data suggested that epigenetic loss of PPP2R2B may be a molecular event affecting the sensitivity of CRC to mTOR inhibitors.

Example 18

Figure 4E:
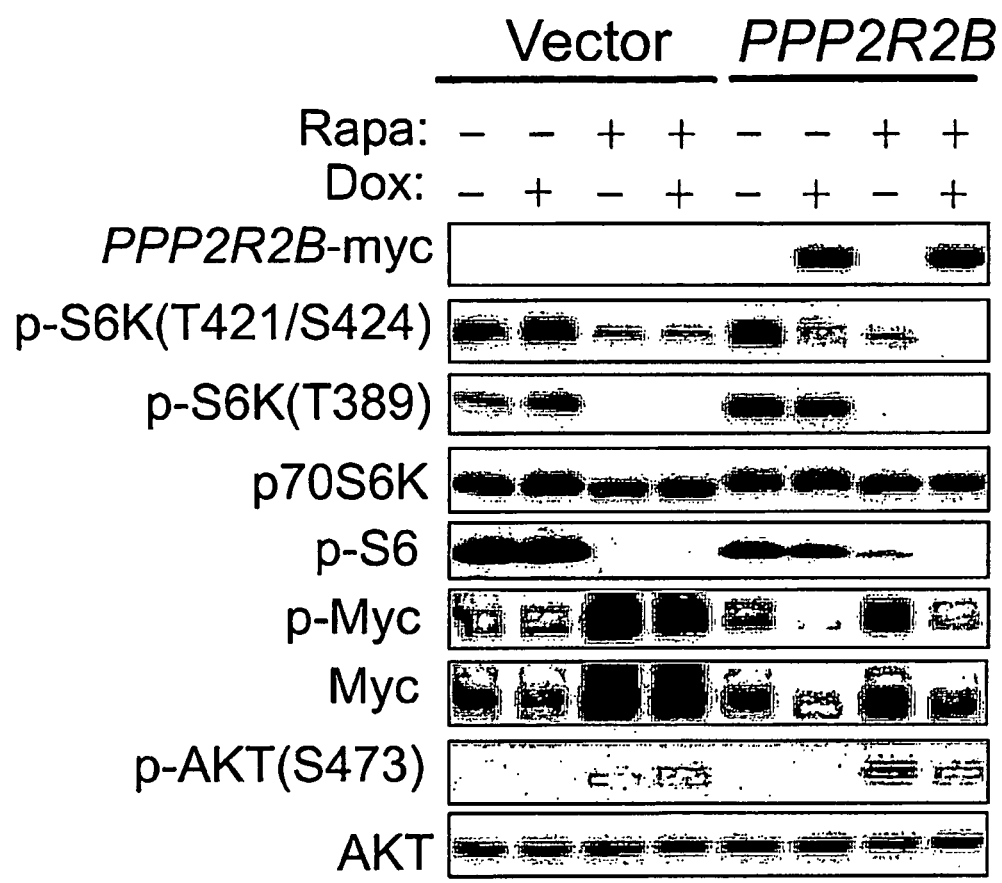

Rapamycin Induces Myc Phosphorylation and Protein Accumulation in CRC Cells, which is Overriden by PPP2R2B Re-Expression A feedback mechanism leading to PI3K activation and AKT S473 phosphorylation in mTORC2-dependent manner has been linked to rapamycin resistance in cancer (O'Reilly et al., 2006; Sarbassov et al., 2006). Indeed, rapamycin treatment of CRC cells resulted in the induction of AKT S473 phosphorylation, but this phosphorylation seemed to be unaffected upon PPP2R2B re-expression (FIG. 4E).

On the other hand, both p70S6K and S6 phosphorylation was effectively abolished by rapamycin treatment in both vector control and PPP2R2B expressing cells (FIG. 4E), thus excluding the possibility that PPP2R2B-induced rapamycin sensitization is associated with AKT S473 or p70S6K.

On the contrary, and intriguingly, we found that rapamycin treatment resulted in a strong induction of Myc phosphorylation and protein accumulation. This effect on Myc protein was not due to increased Myc mRNA (data not shown) and was nearly completely abolished upon PPP2R2B re-expression (FIG. 4E).

Figure 4F:
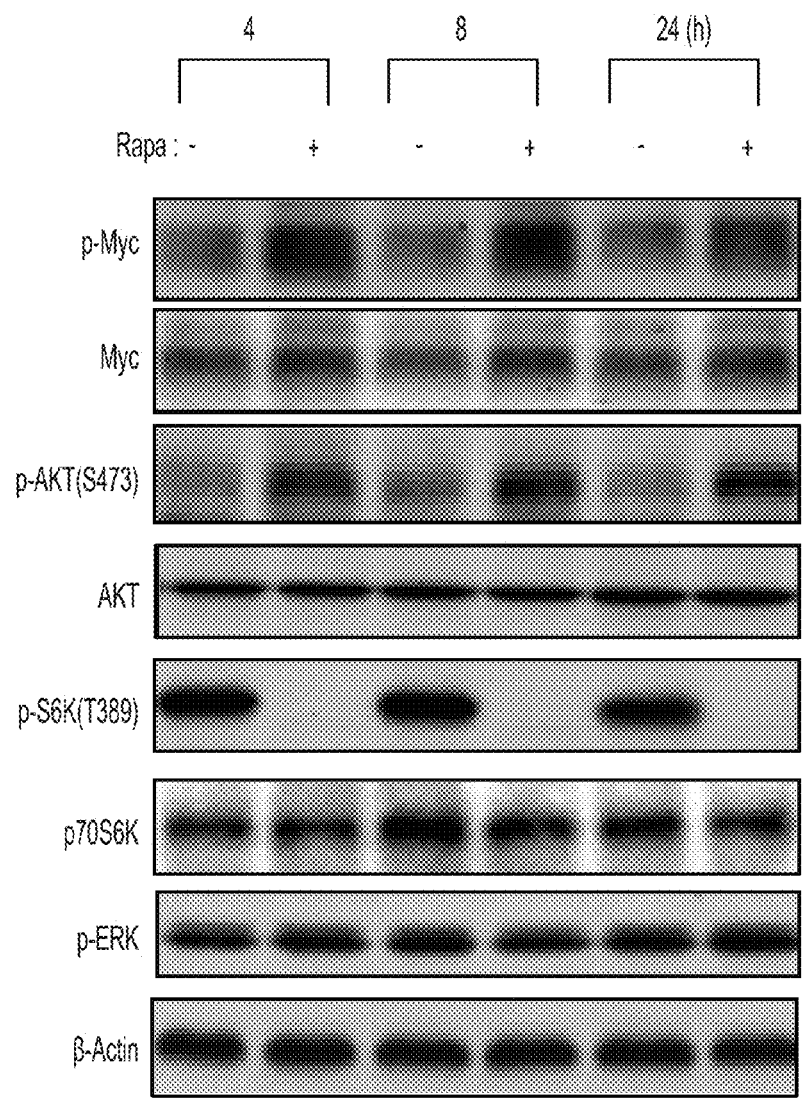

A time course analysis indicates that the Myc response occurred as early as 4 hours, in parallel with the induction of AKT S473 phosphorylation, revealing an additional feedback event in response to rapamycin (FIG. 4F).

Figure 4G:
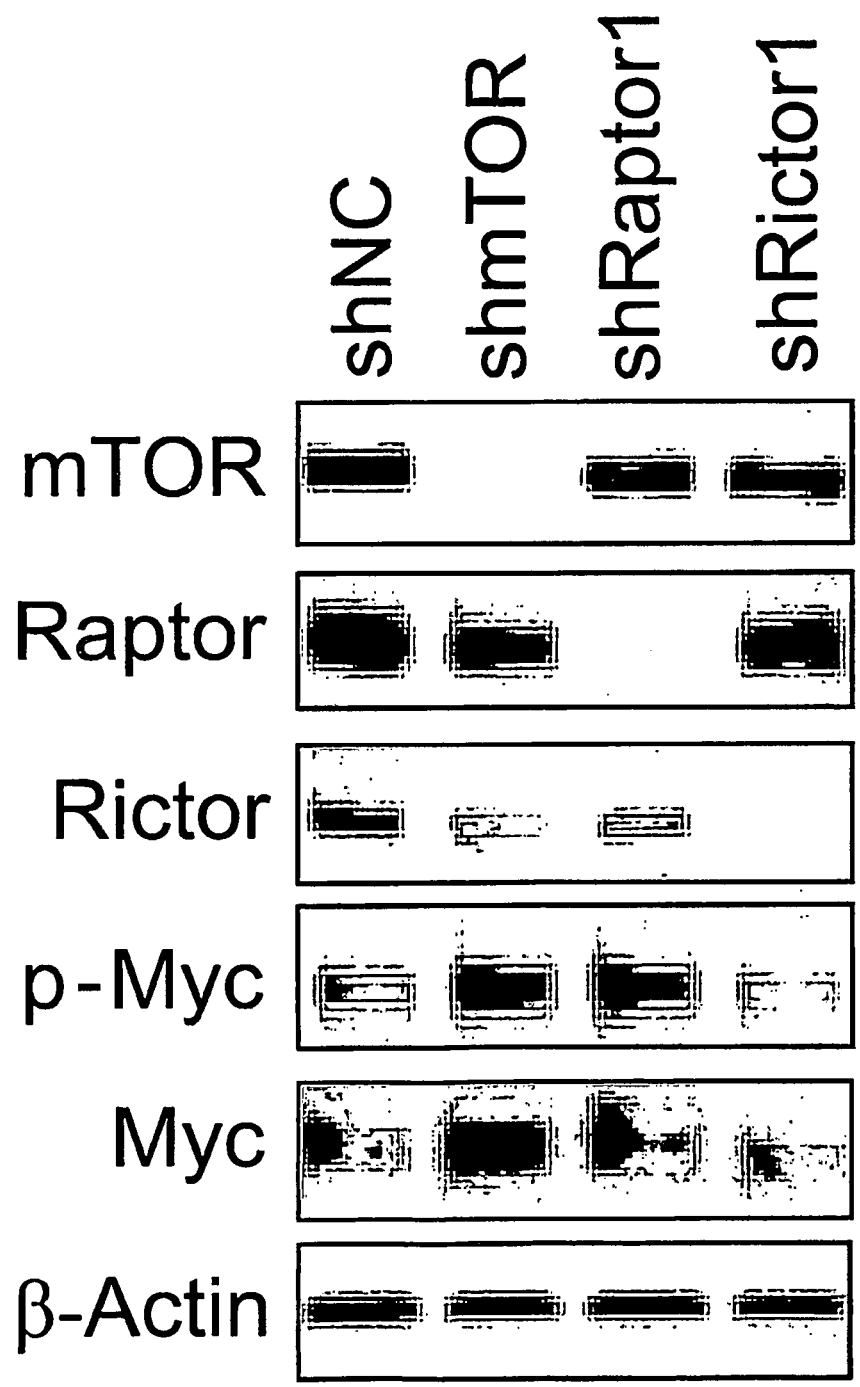

We further confirmed that the rapamycin-induced Myc phosphorylation and accumulation is indeed the result of mTORC1 inhibition, as knockdown of mTOR, or raptor, an essential component of mTORC1, but not mTORC2 component rictor, resulted in a similar induction of Myc phosphorylation (FIG. 4G).

Given the important role of Myc in CRC tumorigenesis, this observation immediately suggests a possible mechanism underlying the PPP2R2B-mediated sensitization to rapamycin.

Figure 13A:
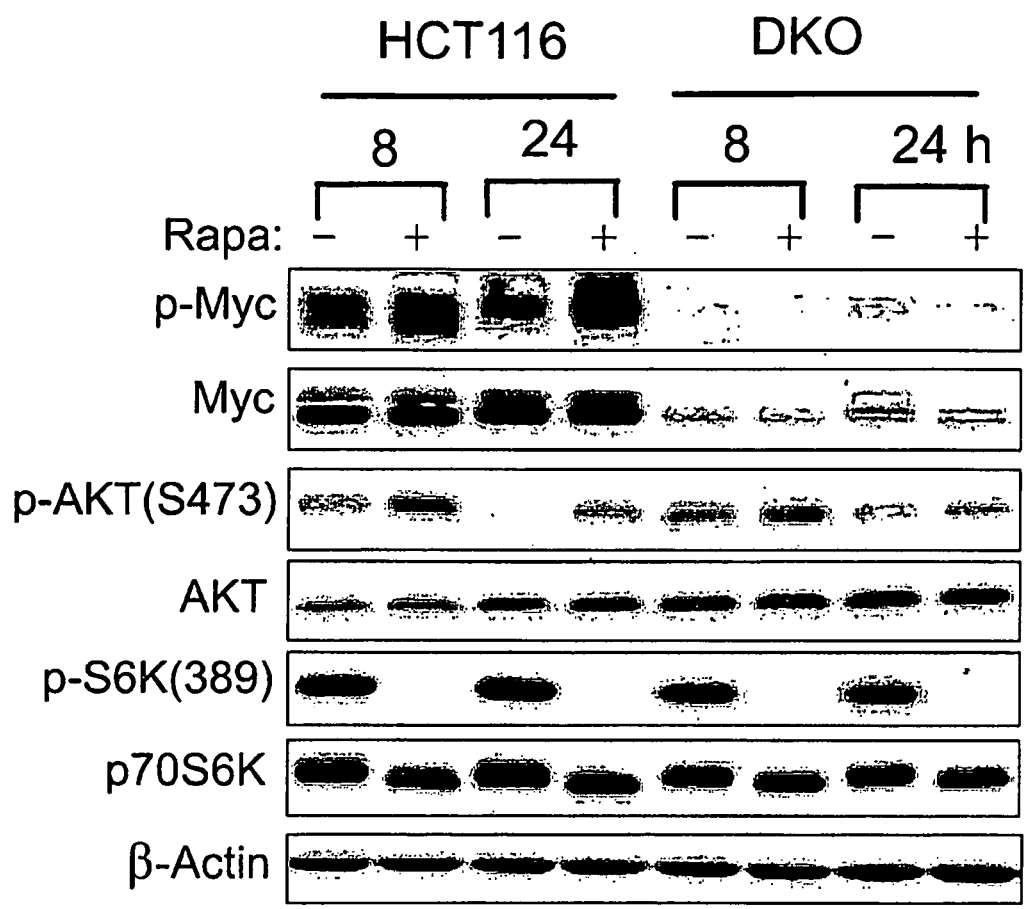
FIGS. 13A-13D. Rapamycin-induced Myc phosphorylation is associated with PPP2R2B expression and rapamycin sensitivity in colon cancer cells.

To substantiate the association of PPP2R2B expression with Myc response and rapamycin sensitivity, we compared the HCT116 cells with DNMTs-deficient HCT116 (DKO) cells in which PPP2R2B becomes re-expressed as a result of promoter demethylation (see earlier FIG. 1I). As in DLD1 cells, Myc phoshorylation was strongly induced by rapamycin in HCT116 cells, whereas in DKO cells, Myc was expressed in a low basal level, and did not respond to rapamycin (FIG. 13A). Of notice, AKT S473 phosphoylation, however, was similarly induced by rapamycin in both cell lines, regardless of PPP2R2B expression status (FIG. 13A).

Figure 13B:
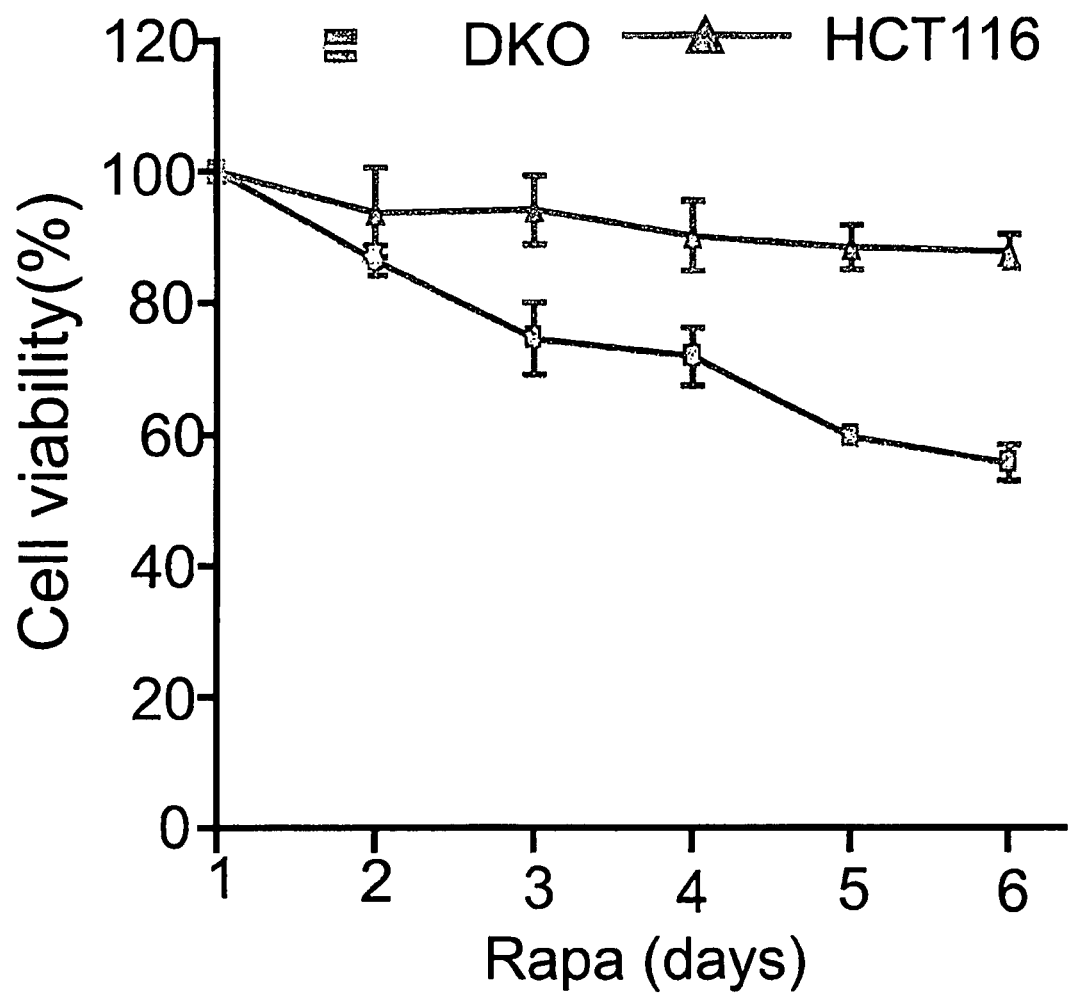

Accordingly, DKO cells which displayed no Myc response were more sensitive to rapamycin treatment as compared to the parental HCT116 cells (FIG. 13B). Taken together, the effect of PPP2R2B on Myc correlated well with the rapamycin response and support a role of PPP2R2B in regulating Myc phosphorylation and thus rapamycin sensitivity.

Figure 13C:
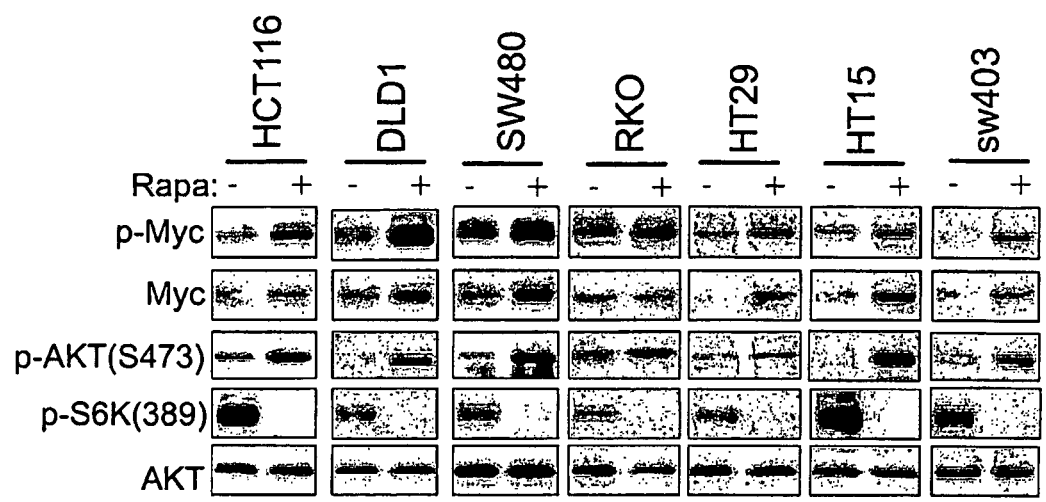
Figure 13D:
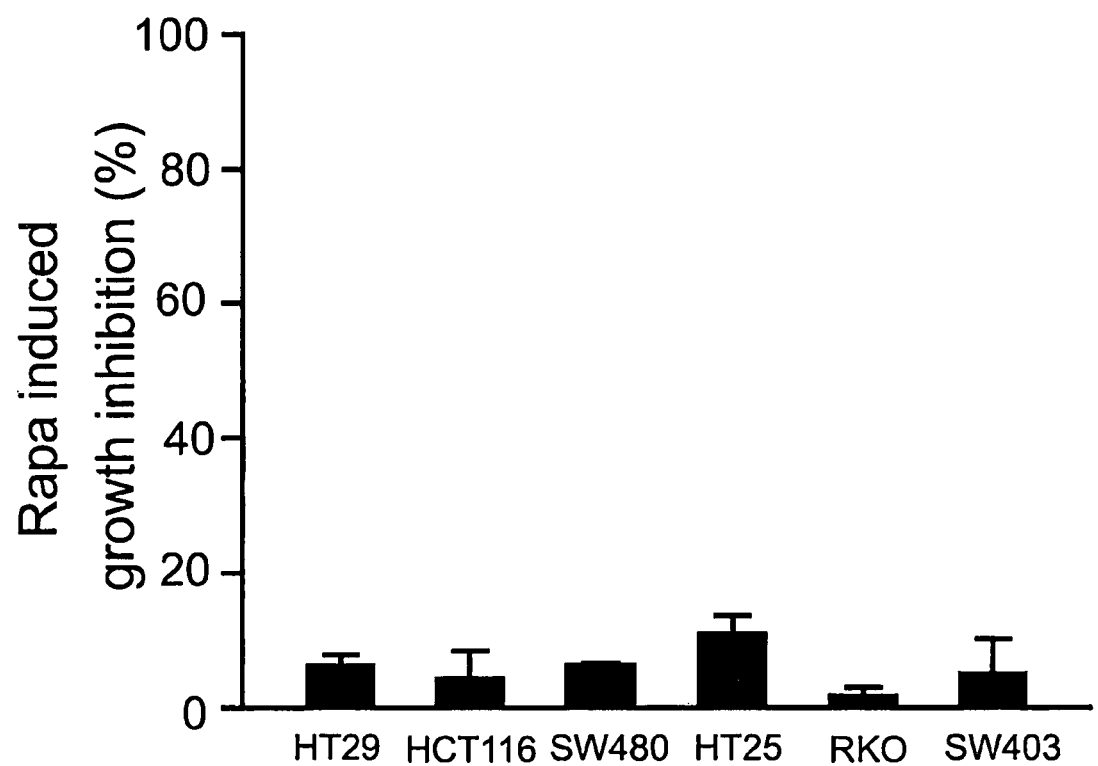

Moreover, corresponding to the consistent silencing of PPP2R2B in CRC, all the CRC cell lines we have examined exhibited a marked induction of Myc phosphorylation upon rapamycin treatment (FIG. 13C). Consistent with the Myc induction, all these CRC cell lines were in general resistant to rapamycin, showing the growth inhibition for less than 10% after 5 days treatment with 10 nM rapamycin (FIG. 13D), a concentration that often results in strong growth inhibition in other cancer cell lines (see later FIG. 14D). This indicates that lack of PPP2R2B in CRC cells is associated with the rapamycin resistance.

Figure 6A:
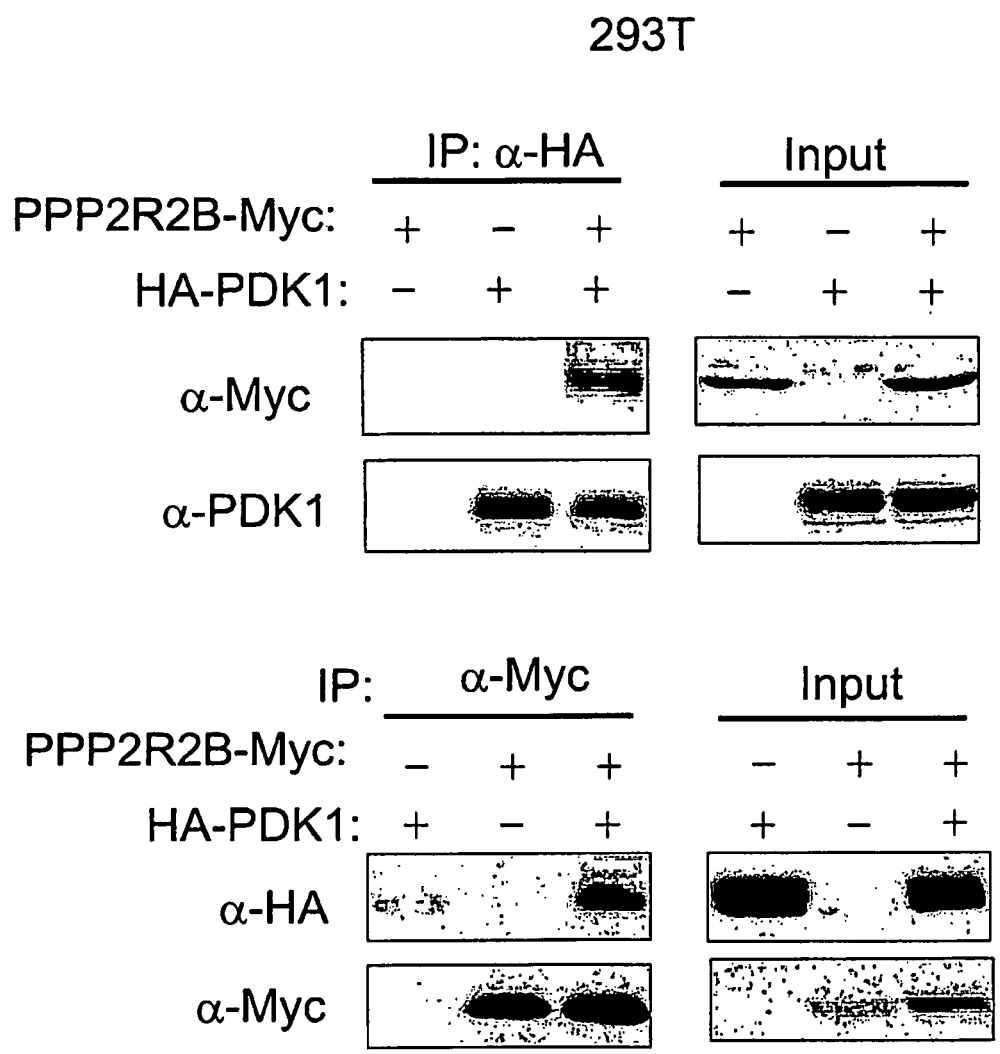
FIGS. 6A-6E. PPP2R2B binds to PDK1 and inhibits its activity that is upregulated in CRC.
Figure 7A:
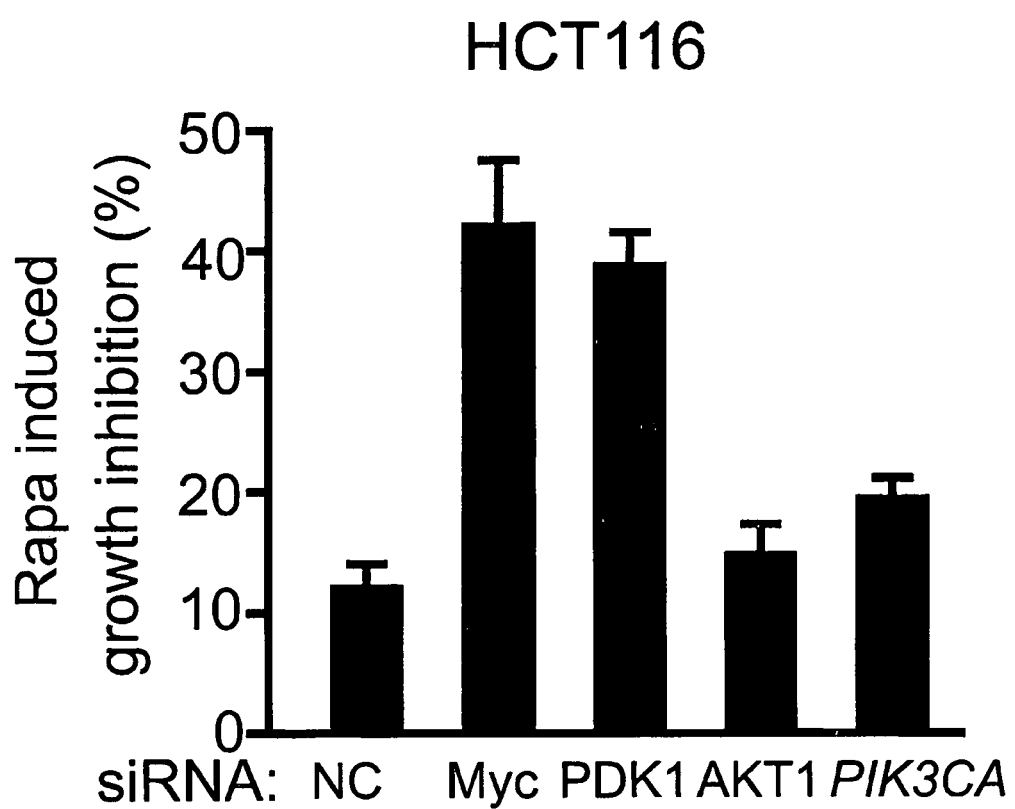
FIGS. 7A-7F. Inhibition of PDK1-Myc signaling overcomes rapamycin resistance.
Figure 14A:
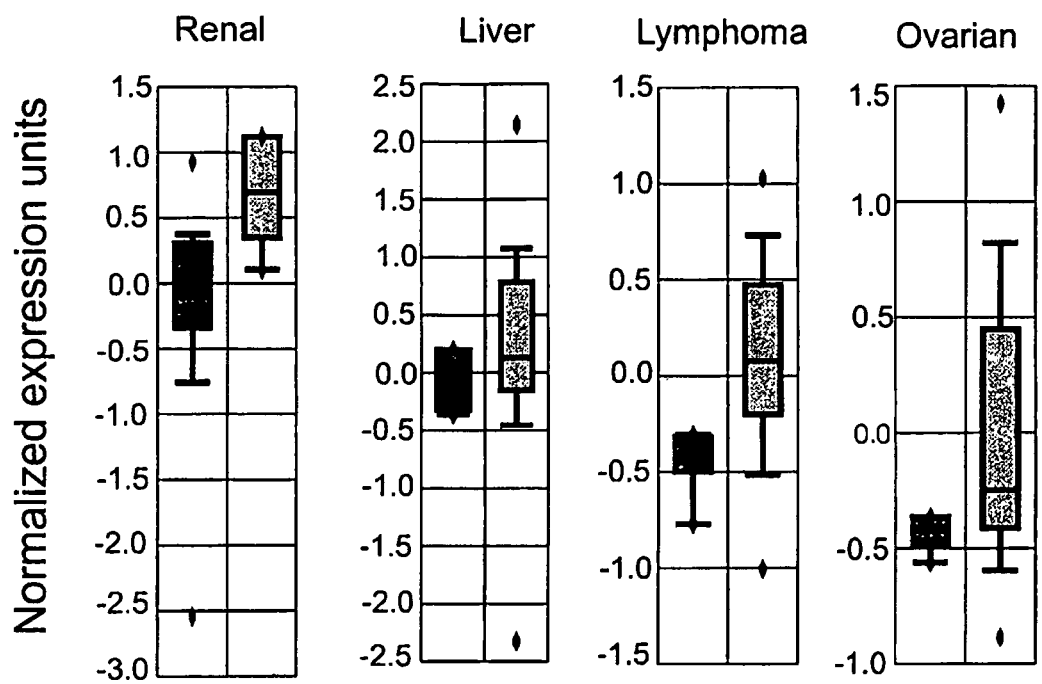
FIGS. 14A-14D. Rapamycin does not induce Myc phosphorylation and is more sensitive in cancer cells expressing PPP2R2B.
Figure 14B:
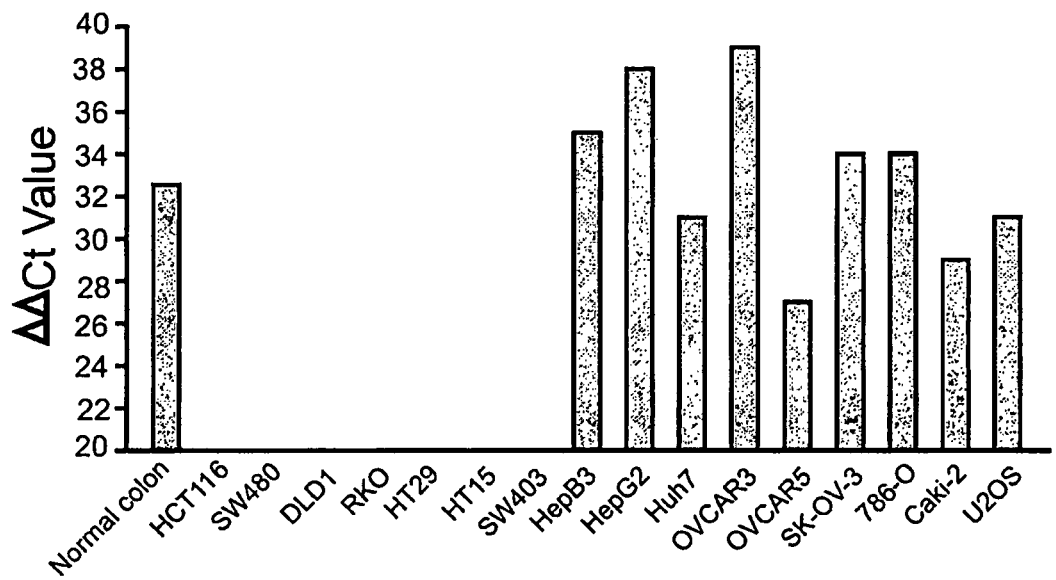

In contrast to colon cancer, the Oncomine database (Rhodes D R., et al, 2004) revealed increased expression in several other human malignancies, including renal, liver, and ovarian cancers (FIG. 6S7A). Real time Taqman assay validated the PPP2R2B expression in a series of cell lines derived from above tumors, including HepG2 and HepB3 cells form hepotoma; 786-O and Caki2 cells from renal carcinoma; OVCAR3, OVCAR5, and SK-OV-3 cells from ovarian carcinoma; as well as U2OS cells from osteosarcoma, as opposed to the silenced expression of PPP2R2B in CRC lines (FIG. 14B).

Figure 14C:
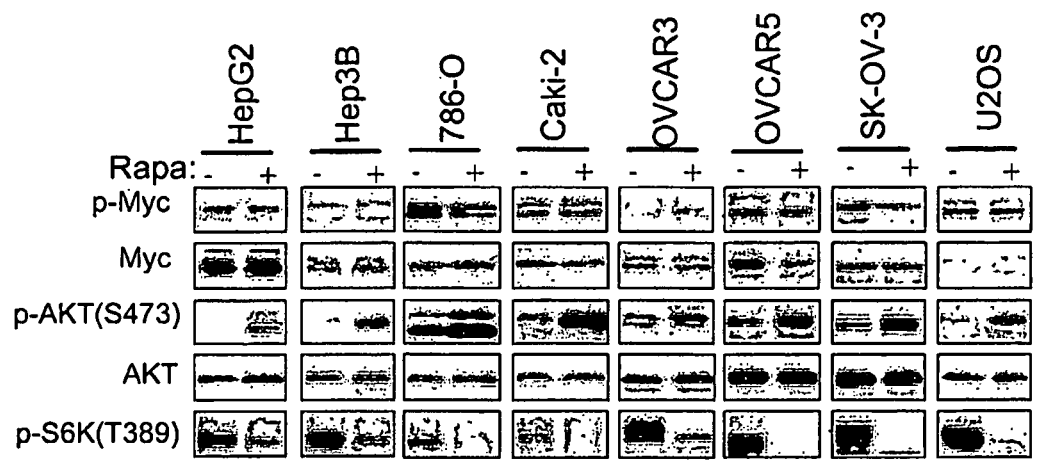
Figure 14D:
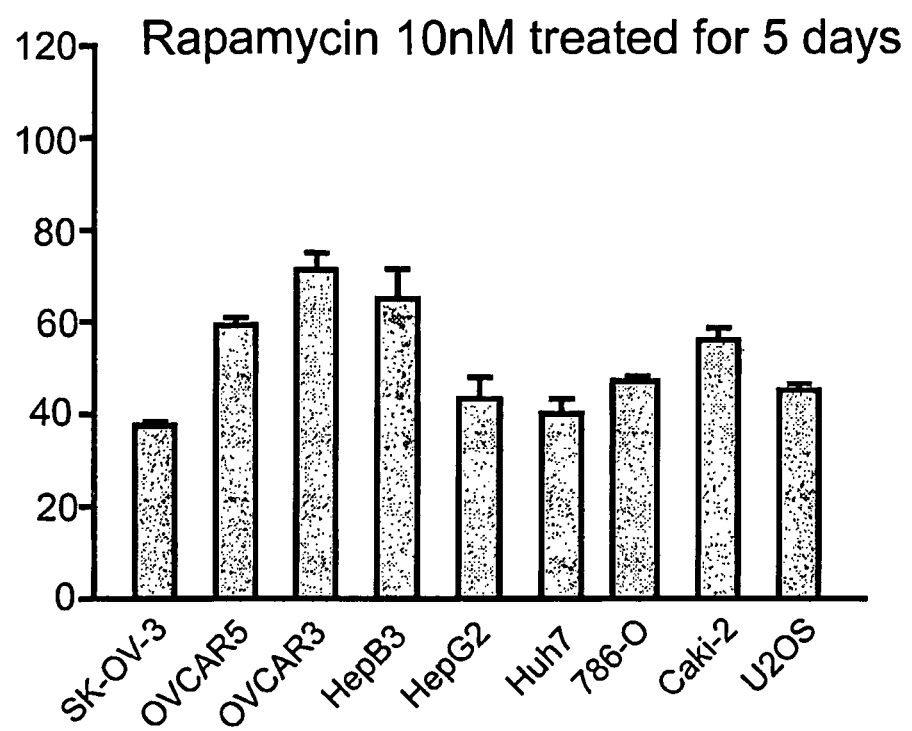

Of significant notice, none of these PPP2R2B-expressing cancer cell lines showed an induction of Myc phosphorylation in response to rapamycin, despite a consistent induction of AKT S473 phosphorylation in all cases (FIG. 14C). Moreover, these cell lines were much more sensitive to rapamycin in general, as compared to CRC cell lines (FIG. 14D). These results together have provided evidence to show:

(1) the PPP2R2B silence or expression in cancer cells correlates with the sensitivity or resistance to rapamycin;

(2) This correlation is associated with at least in part the ability of rapamycin to induce Myc phosphorylation.

Example 19

Rapamycin-Induced Myc Phosphorylation is PDK1-Dependent, but PIK3CA-AKT Independent mTORC2-dependent AKT S473 activation depends on receptor tyrosine kinase (RTK) signaling upon growth factor stimulation, and PIK3CA (encoding p110α) is required for this process (Guertin and Sabatini, 2007; Sekulic et al., 2000), and PIK3CA (encoding p110α) is required for this process (Jia et al., 2008; Knight et al., 2006; Zhao et al., 2006).

Figure 5A:
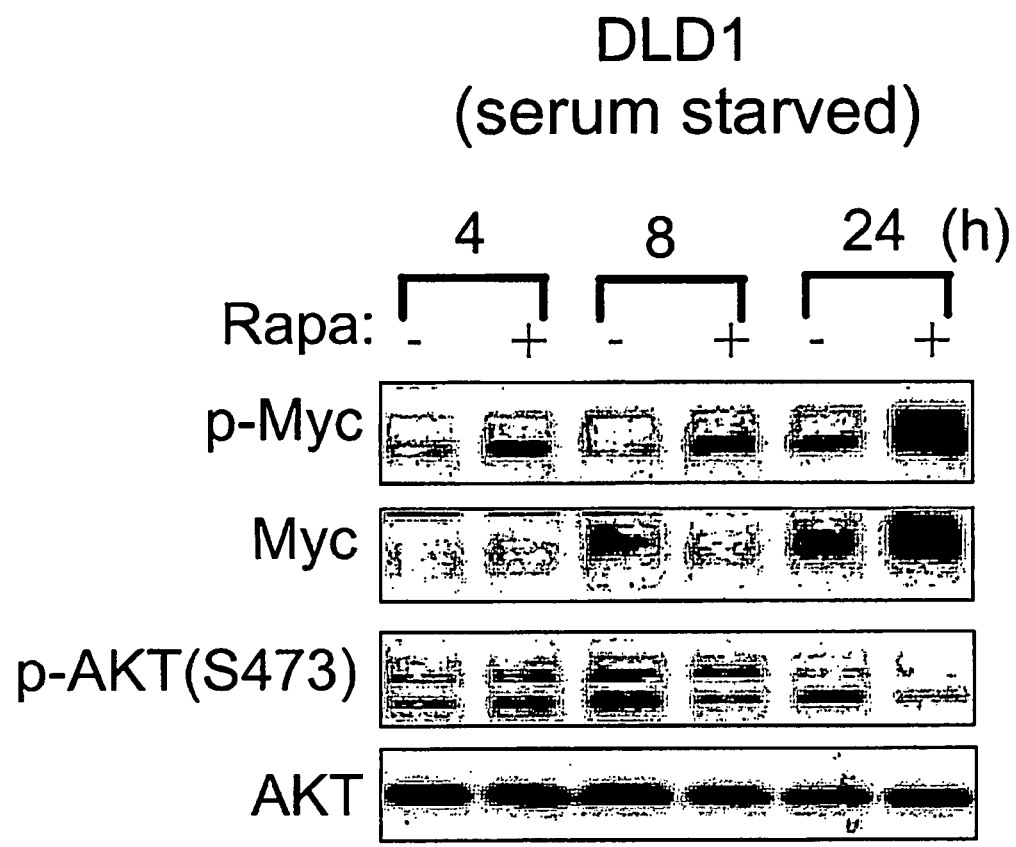
FIGS. 5A-5F. Rapamycin induced Myc phosphorylation requires DK1, but not PIK3CA-AKT.
Figure 5B:
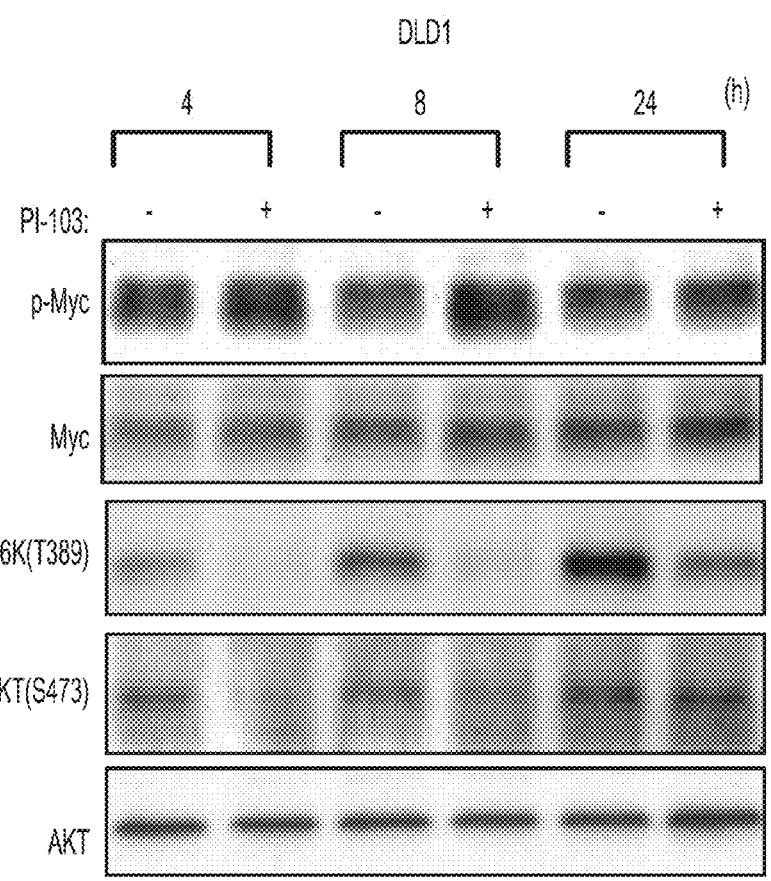

We found that serum starvation abolished rapamycin-induced AKT S473 phosphorylation, but had no significant effect on rapamycin-induced Myc phosphorylation (FIG. 5A). In addition, PIK-103, a dual PIK3CA and mTORC1 inhibitor (Fan et al., 2006), reduced AKT 5473 phosphorylation, but enhanced Myc phosphorylation (FIG. 5B). These findings suggest that rapamycin induces Myc phosphorylation through a distinct mechanism that does not depend on PIK3CA.

Figure 5C:
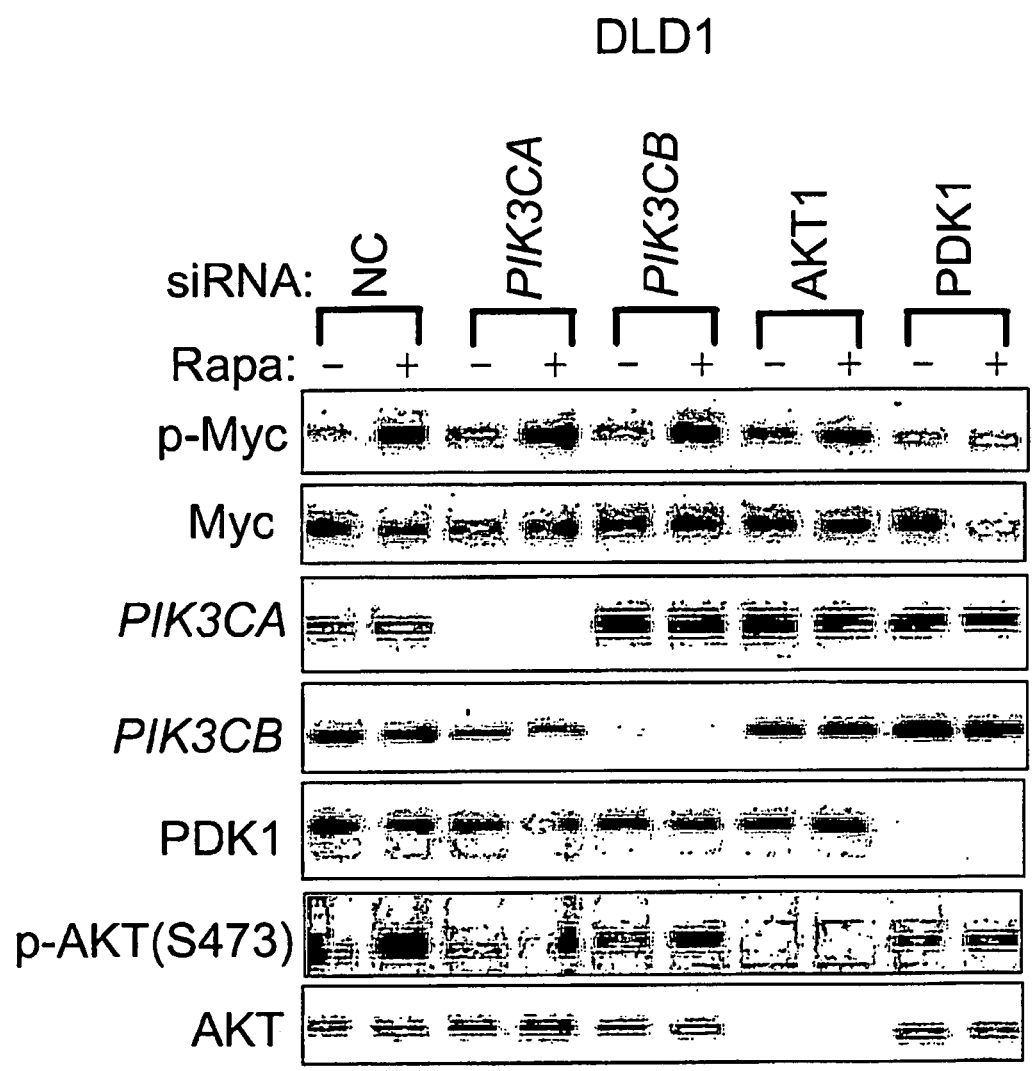
Figure 5D:
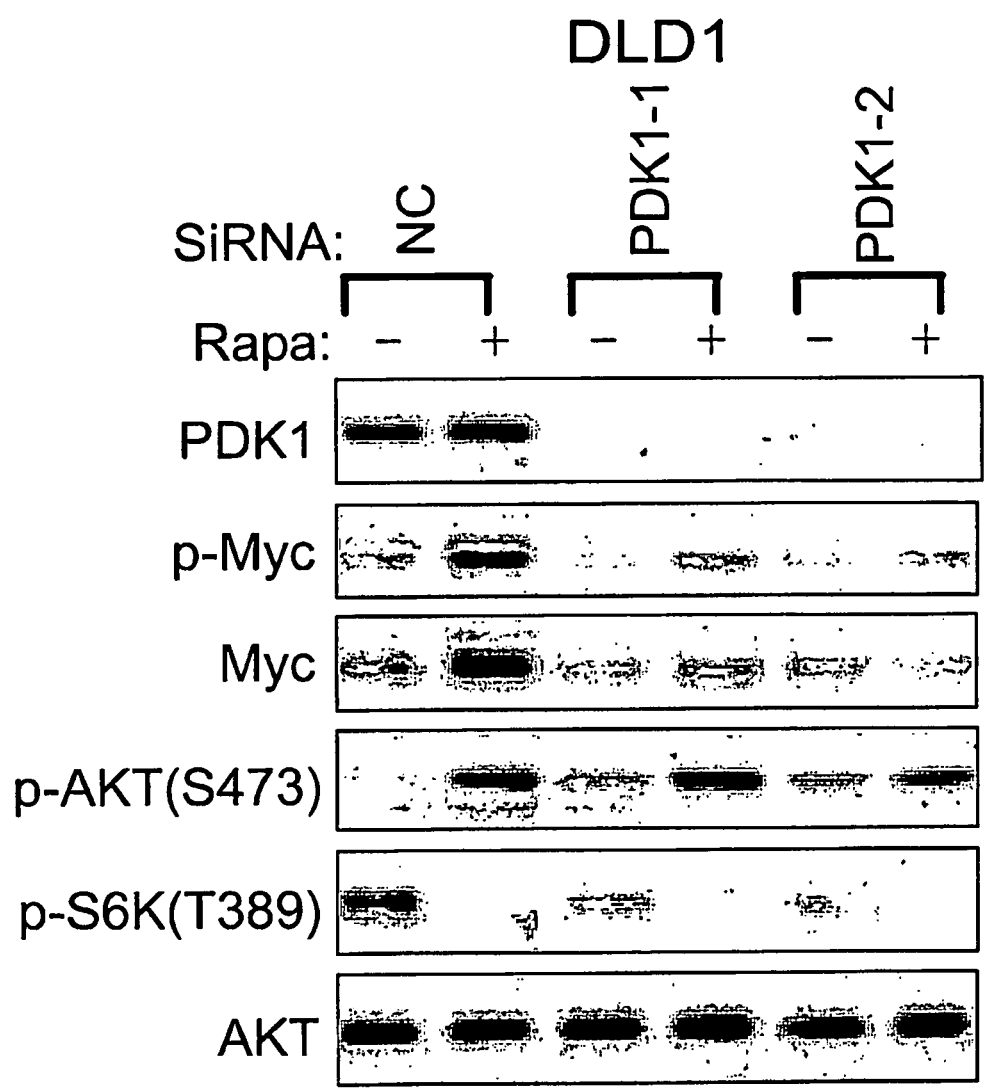
Figure 5E:
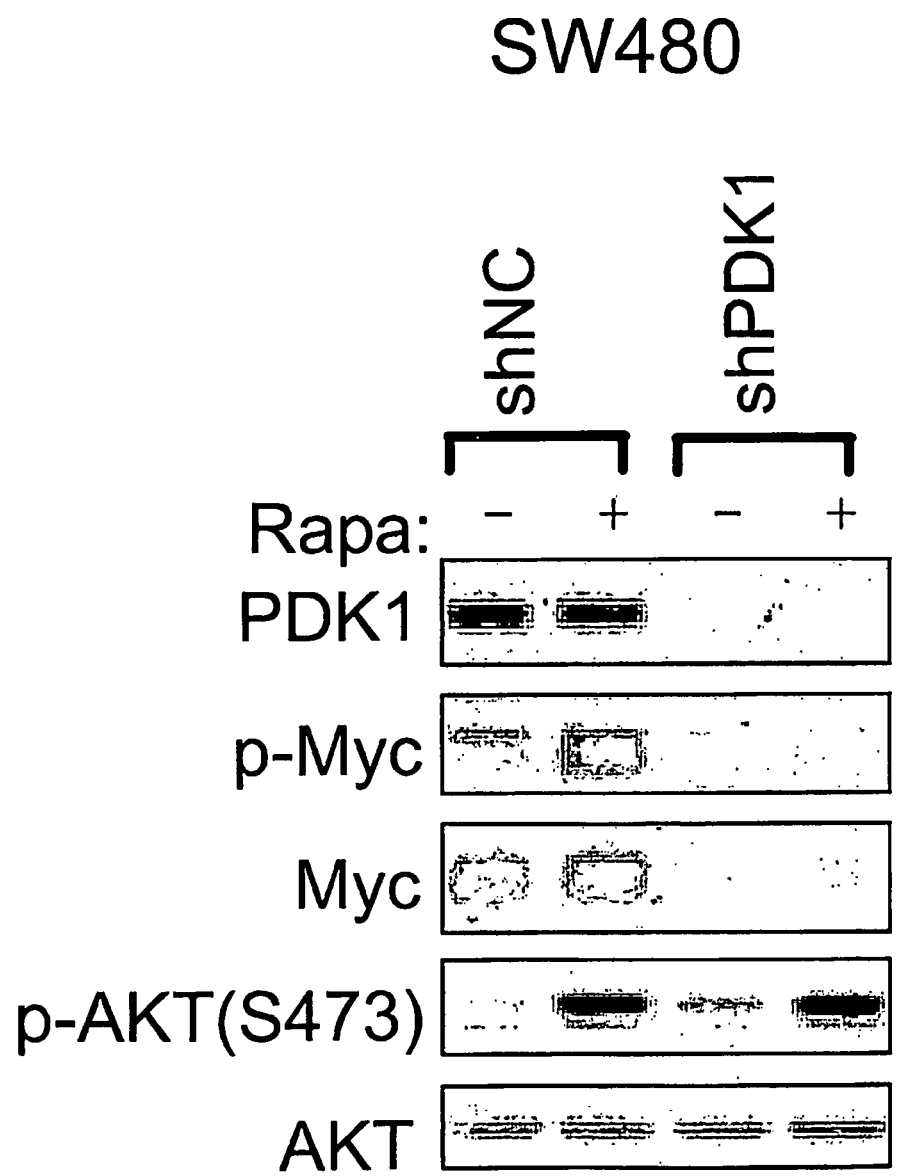

To further elucidate the upstream signals leading to rapamycin-induced Myc phosphorylation, we knocked down several major components in the PI3K and mTOR pathway. The results show that PDK1 knockdown effectively inhibited rapamycin-induced Myc phosphorylation, while knockdown of PIK3CA, PIK3CB, or AKT1 had no such an effect (FIG. 5C). Further experiments with two additional PDK1 siRNAs and a PDK1 shRNA in DLD1 and SW480 cells confirmed its effect on Myc phosphorylation (FIG. 5D and FIG. 5E); but of notice, PDK1 knockdown had no discernable effect on AKT-S473 phosphorylation, which however can be clearly abolished by PIK3CA knockdown (FIG. 5C). Conversely, ectopic Myc showed enhanced phosphorylation and accumulation when co-expressed with ectopic PDK1, further supporting a role of PDK1 in upregulation of Myc.

Figure 5F:
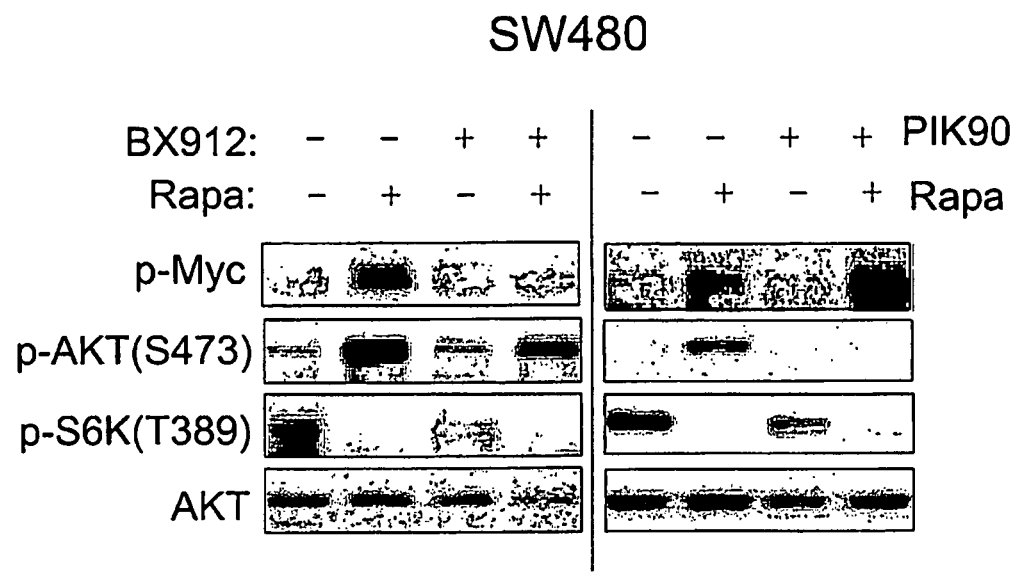

To substantiate this finding, we made use of specific small molecule inhibitor of PDK1, BX912 (Feldman et al., 2005) and a specific PIK3CA inhibitor PIK90 (Fan et al., 2006; Knight et al., 2006). Consistent with PDK1 knockdown, BX912 treatment abolished rapamycin-induced Myc phosphorylation (FIG. 5F), but had no much effect on AKT S473. By contrast, PIK90 was unable to inhibit rapamycin-induced Myc phosphorylation; but effectively abolished the AKT S473 phosphorylation (FIG. 5G).

Taken together, these results provided convincing evidence to show that rapamycin induces a PDK1-dependent Myc phosphorylation, in parallel to PIK3CA-sensitive AKT S473 phosphorylation.

Example 20

PPP2R2B Binds to and Inhibits PDK1 Activity

We next tested the possibility that PPP2R2B may directly interact with PDK1 and modulate its activity.

Figure 6B:
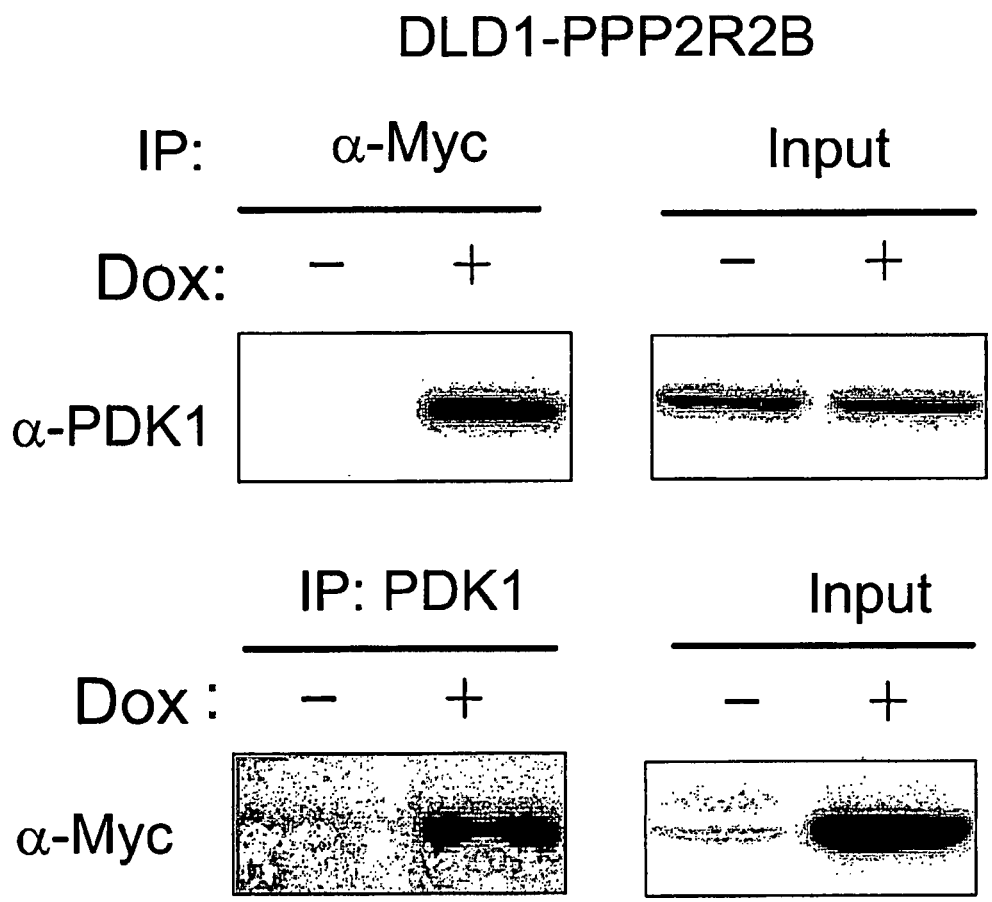

Co-transfection of PPP2R2B and PDK1 plasmids in 293T cells confirmed this hypothesis and showed that ectopic PDK1 co-immunoprecipated with the PPP2R2B-Myc and vice versa (FIG. 6A). This was further confirmed in DLD1-PPP2R2B cells in which Dox-induced PPP2R2B co-immunoprecipitated with endogenous PDK1 (FIG. 6B).

Figure 15A:
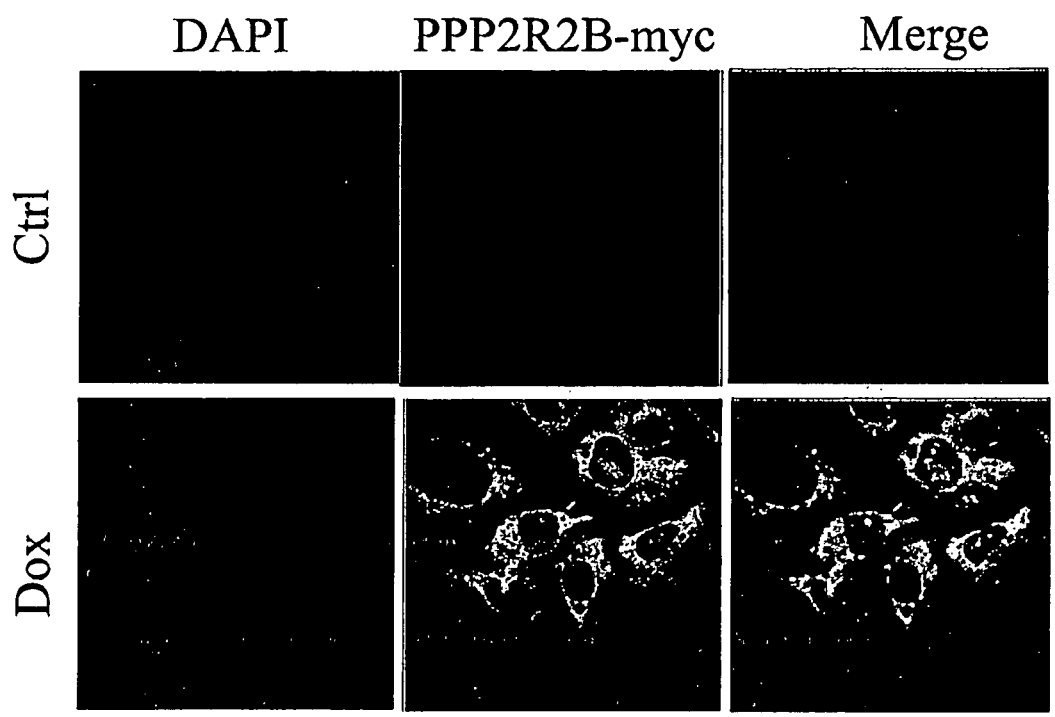
FIGS. 15A-15C. Subcellular localizations of PPP2R2B, PDK1, and Myc in DLD1 cells.
Figure 15B:
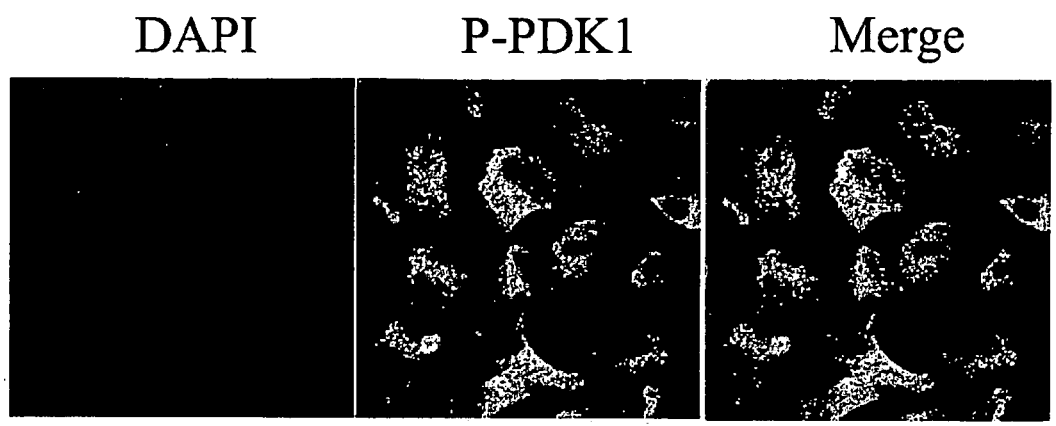

It is known that PDK1 needs to be recruited from the cytosol to the plasma membrane to activate its downstream targets (Kikani et al., 2005). Both PPP2R2B and PDK1 are predominately located in the cytoplasm (FIG. 15A and FIG. 15B). Thus, the cytoplasmic interaction of PDK1 with PPP2R2B may affect its membrane recruitment.

Figure 6C:
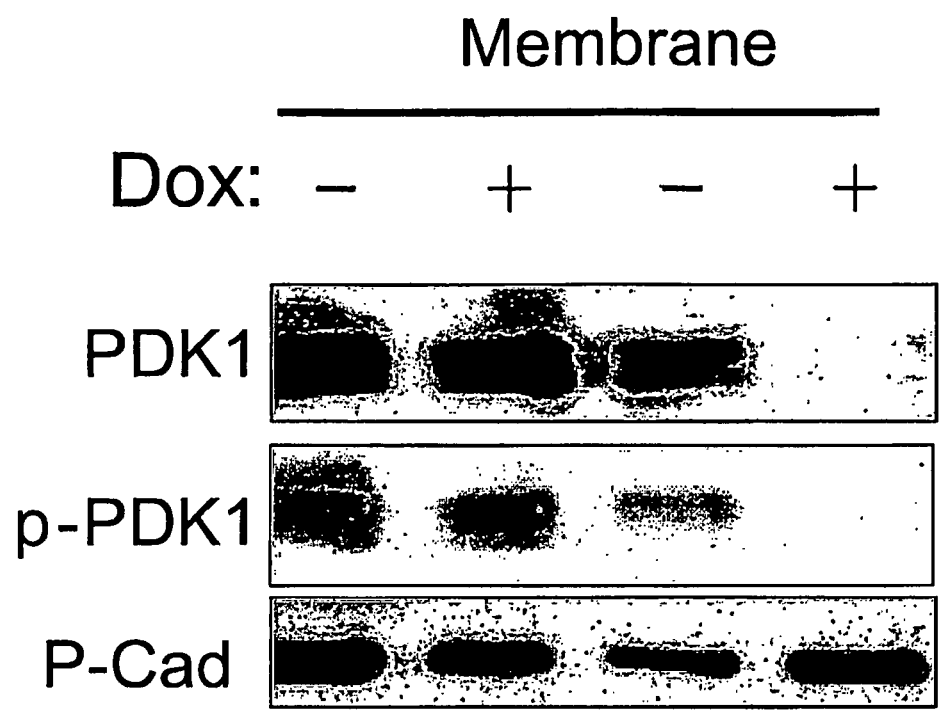
Figure 6D:
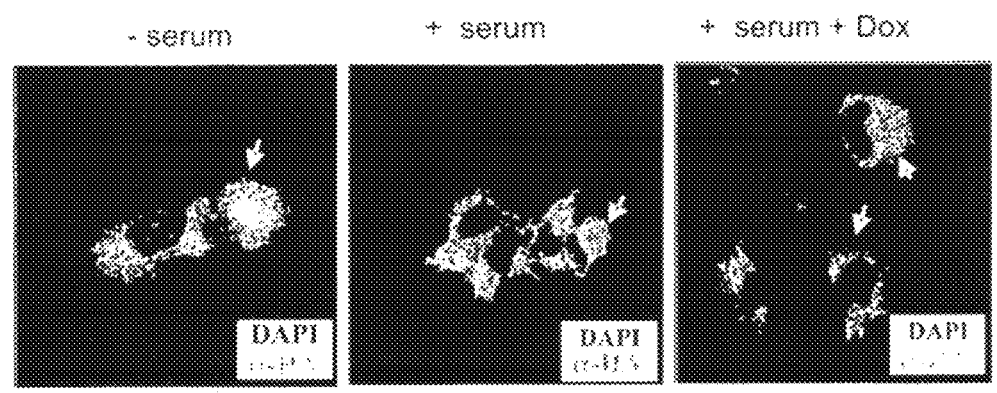
Figure 15C:
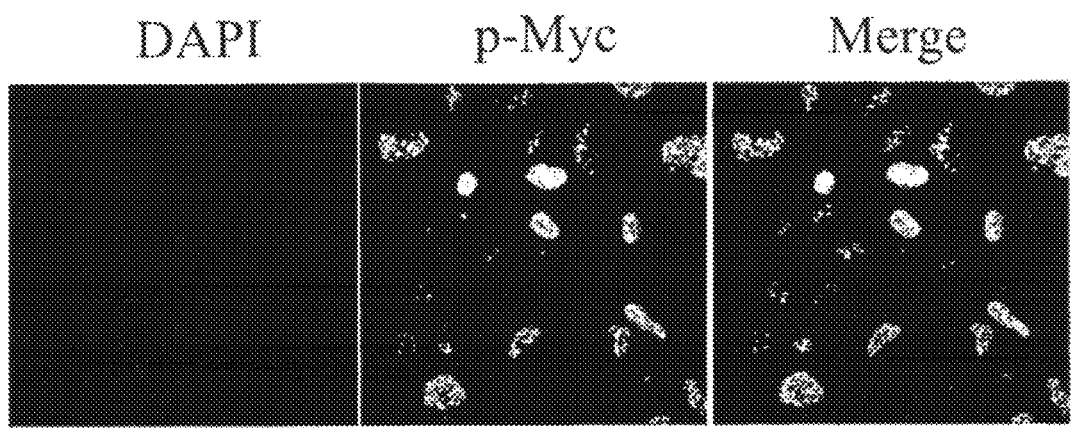

Indeed, upon Dox treatment of DLD1-PPP2R2B cells, we detected the downregulation of both total and phosphorylated PDK1 in plasma membrane (FIG. 6C). Moreover, in DLD1-PPP2R2B cells under serum starvation, ectopic PDK1-HA was mainly detected in the cytosol, but expressed in both cytosol and cell membrane upon serum stimulation, which was abolished when cells were treated with Dox to induce PPP2R2B (FIG. 6D). Taken together, the results demonstrate that PPP2R2B-PP2A complex binds to and inhibits PDK1 membrane recruitment for activation. Because Myc is accumulated mainly in the nucleus in response to rapamycin (FIG. 15C), the effect of cytoplasmic PPP2R2B-PDK1 on Myc is more likely to be indirect and may route through a PDK1 downsteam kinases substrates.

Figure 6E:
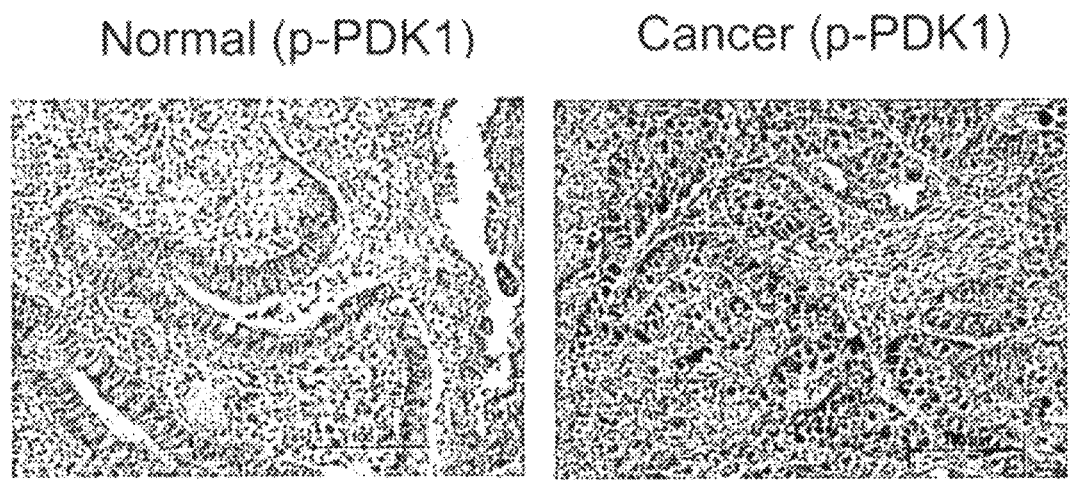

PPP2R2B is lost in >90% of CRC. We next assessed whether PDK1 activity is consistently upregulated in primary CRC tissues, which has not been previously assessed. Immunohistochemical (IHC) staining on primary tumor and normal tissues fixed on tissue microarray (TMA) slides containing normal tissues and human colorectal cancer tumors. The result showing a strong staining of phosphorylated PDK1 as compared to the normal tissues in human colorectal cancer (FIG. 6E).

Although the mutations of PIK3CA and PTEN, which occurs in 30% and 20% of CRC, respectively, may also account for the induction of PDK1, the loss of PPP2R2B may provide additional mechanism explaining the uniform PDK1 upregulation in CRC.

This finding strongly suggests that PDK1 may be an ideal therapeutic target for CRC.

Example 21

Inhibition of PDK1 and Myc, but not PIK3CA and AKT, Sensitizes Therapeutic Response of Rapamycin We next evaluated how the two distinct signaling pathways contribute to rapamycin resistance.

Figure 7B:
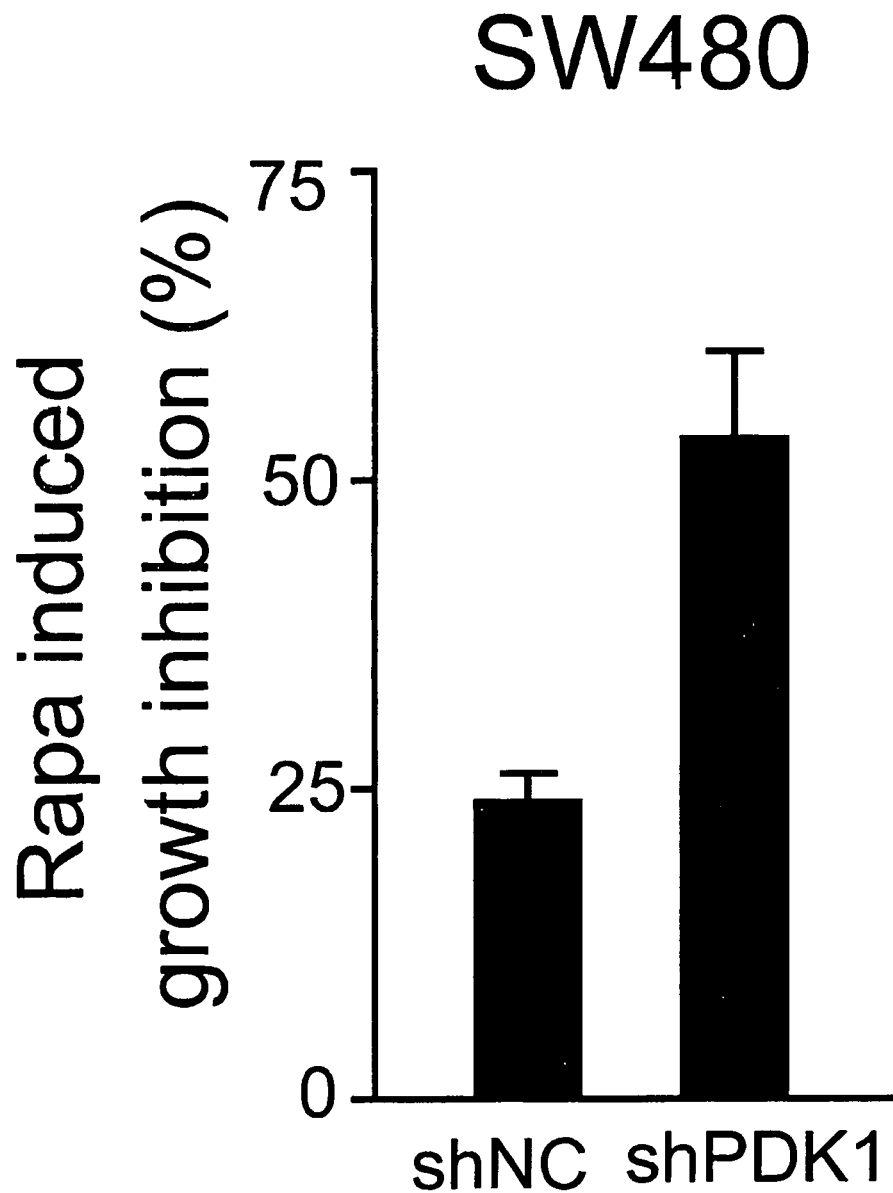

PDK1 or Myc knockdown resulted in markedly increased sensitivity of rapamycin in HCT116 cells, while PIK3CA or AKT knockdown did not give rise to a similar effect (FIG. 7A). The effect of PDK1 ablation on Myc and rapamycin sensitivity was further validated in SW480 cells expressing a retroviral PDK1 shRNA (FIG. 7B).

These results support a causal relationship between PDK1-Myc induction and rapamycin resistance in CRC cells. Moreover, the data argue for a more important role of PDK1-Myc signaling, as compared with PIK3CA-AKT signaling, in rapamycin resistance in CRC cells.

Identification of PPP2R2B-regulated PDK1 suggests a practical approach for overcoming rapamycin resistance, which may be achieved through pharmacological inhibition of PDK1.

Figure 7C:
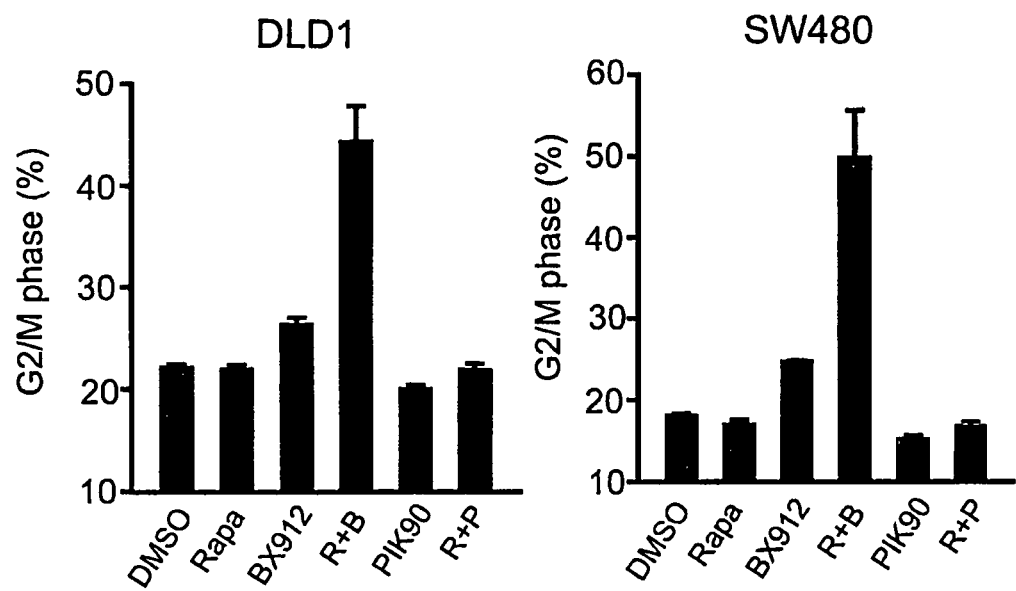
Figure 16A:
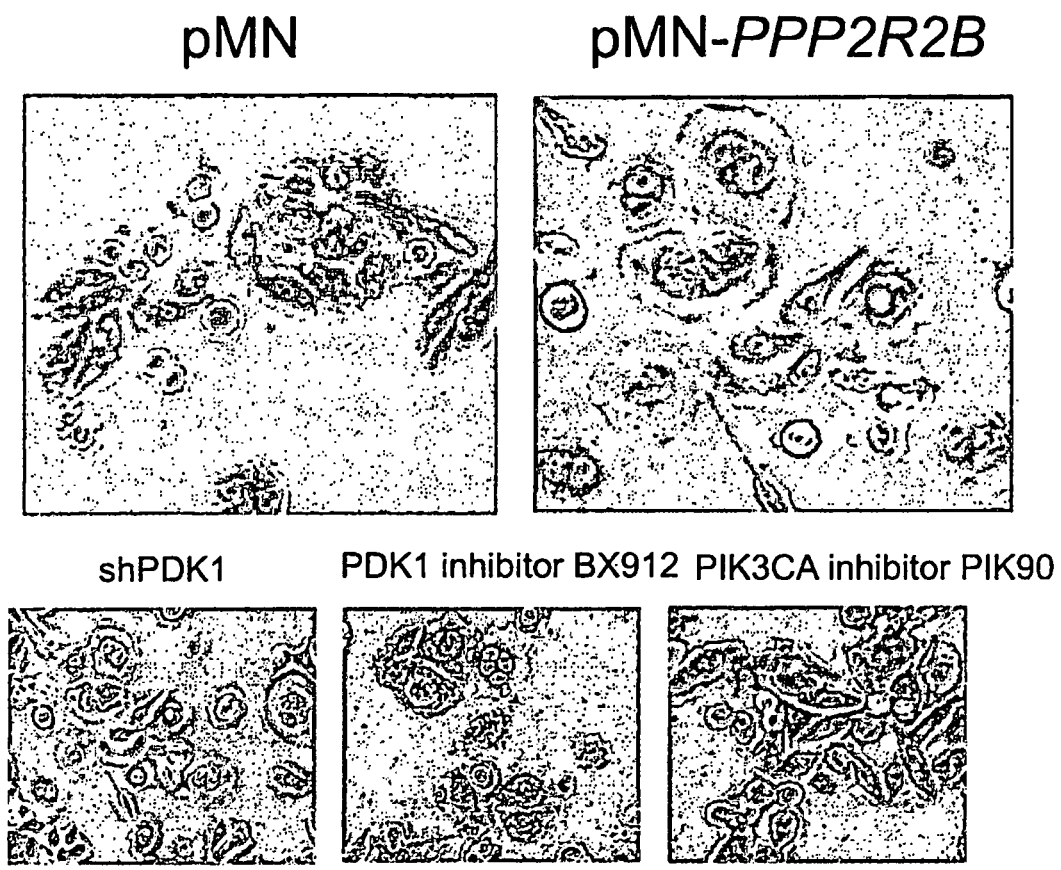
FIGS. 16A-16B. Pharmacological effects of PDK1 inhibitor BX912 and shPDK1 in colon cancer cells.
Figure 16B:
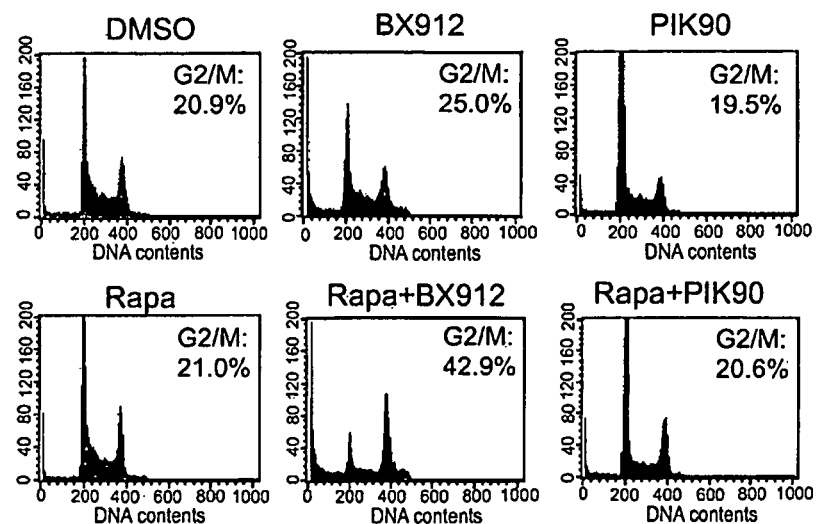
Figure 16B:
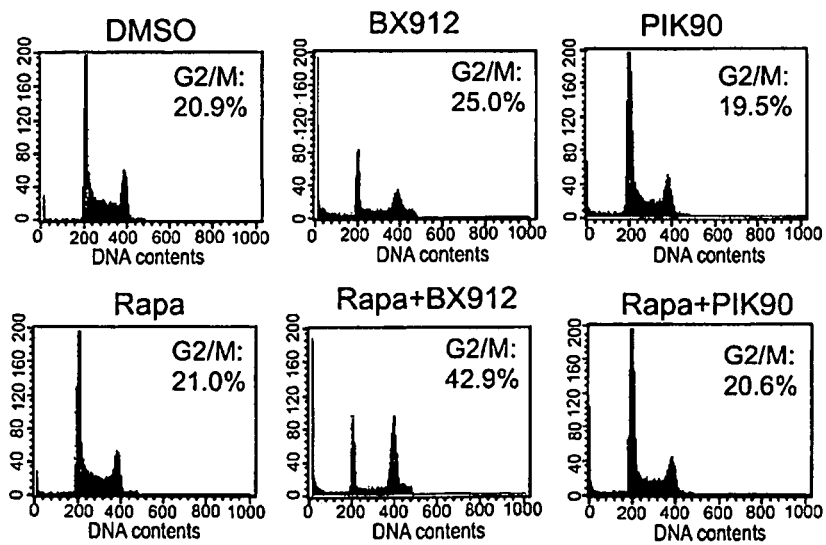

We found that PDK1 shRNA or BX912, but not PIK90, induced a morphological change similar to that seen upon PPP2R2B re-expression (FIG. 16A). Moreover, BX912, but not PIK90, synergized with rapamycin to induce strong G2/M arrest in CRC cells (FIG. 7C and FIG. 16B), which is again remarkably consistent with the synergistic effect of PPP2R2B and rapamycin on G2/M (see earlier FIG. 4C).

Figure 7D:
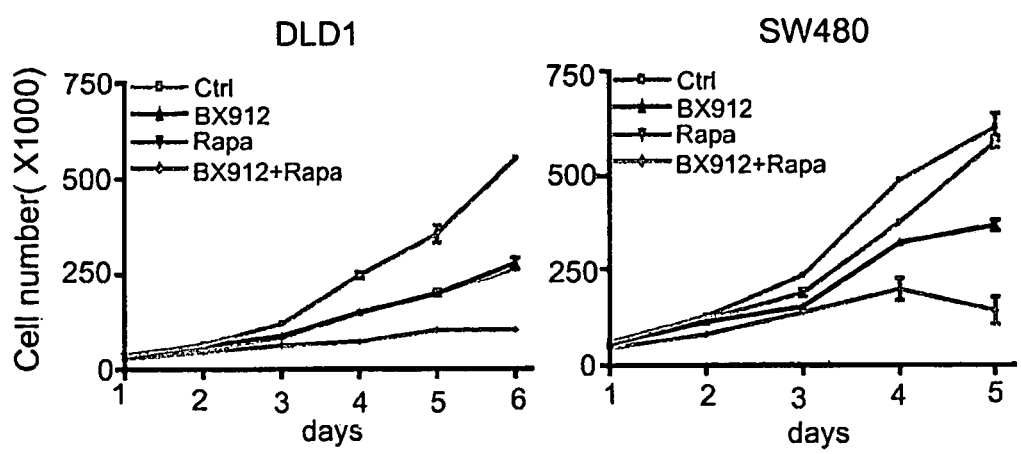
Figure 7E:
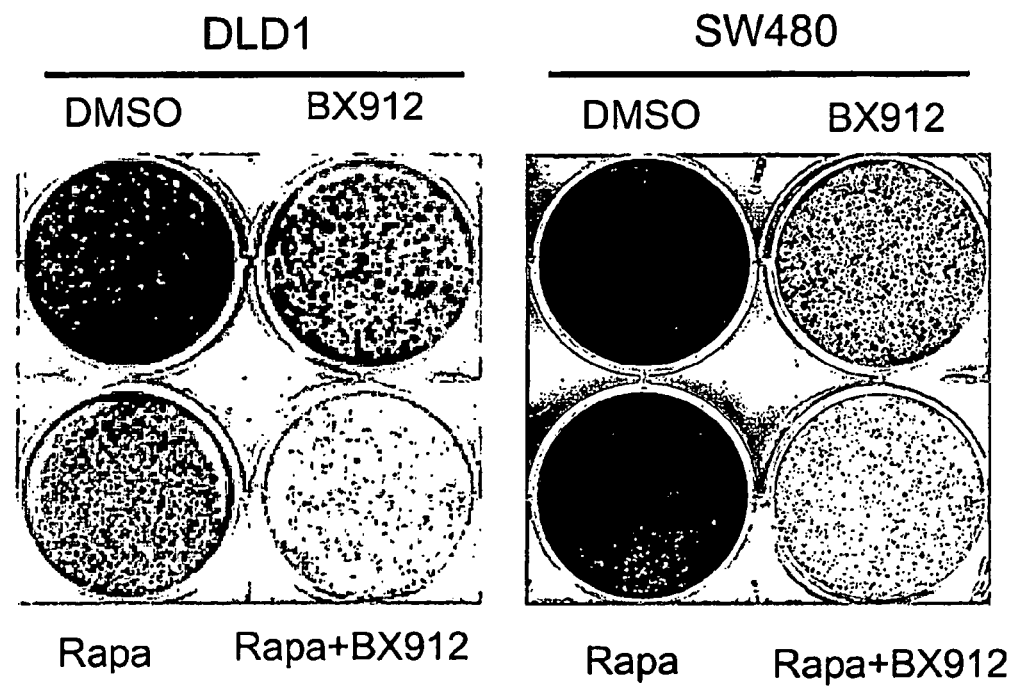

Thus, pharmacologic inhibition of PDK1, but not PIK3CA, has phenocopied the effect of PPP2R2B re-expression, further supporting the genetic interaction between PPP2R2B and PDK1. As such, we observed a synergistic loss of cell viability between BX912 and rapamycin in CRC cells in both a 5-day cell viability assay (FIG. 7D) and a 2-week colony formation assay (FIG. 7E).

Figure 7F:
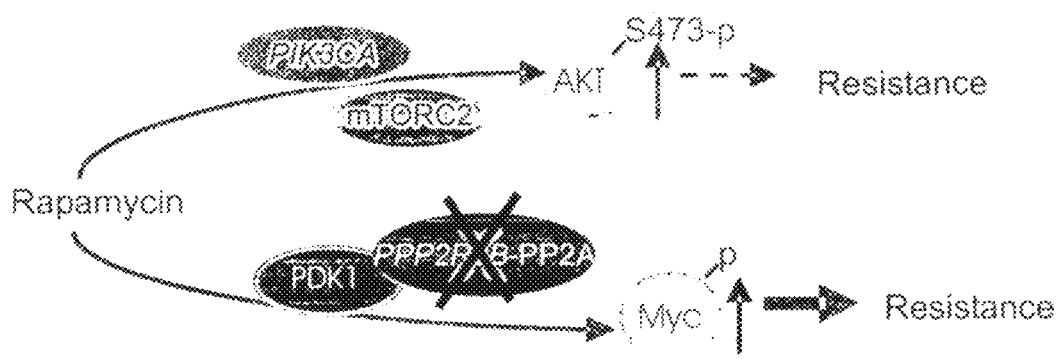

These findings support a model in which the loss of PPP2R2B in CRC results in activation of PDK1-dependent Myc phosphorylation in response to rapamycin treatment, leading to rapamycin resistance in a PIK3CA-AKT independent manner (FIG. 7F). Pharmacologic inhibition of PDK1 can overcome rapamycin resistance by preventing the Myc phosphorylation, pointing out a potential combination strategy for CRC treatment.

Example 22

Discussion

In this paper, we have identified a specific PP2A tumor suppressor complex transcriptionally inactivated in both CRC cell lines and patient-derived CRC samples.

Functional analysis reveals its inhibition of PDK1-Myc axis as a potential tumor suppressor mechanism. Remarkably loss of this regulation in CRC conferred a strong activation of oncogenic Myc phosphorylation in response to mTORC1 inhibitor rapamycin, leading to rapamycin resistance.

This study provides an illustration of epigenetic control of important oncogenic signaling pathways and identifies a molecular determinant and potential biomarker of rapamycin sensitivity. Additionally, the pathway elucidated provides a therapeutic approach to alleviate the rapamycin resistance.

Example 23

Discussion—PPP2R2B-associated PP2A Complex as a Tumor Suppressor

We have demonstrated here that a PP2A regulatory B subunit, PPP2R2B, is epigenetically inactivated by DNA hypermethylation in colorectal cancer, and provided evidence that PPP2R2B can act as a tumor suppressor.

Despite the fact that the tumor suppressor function of PP2A had been well-demonstrated in transformed model system (Chen et al., 2005; Chen et al., 2004; Sablina et al., 2007; Zhao et al., 2003), PP2A subunits have been found to be mutated or deleted only in 8-15% of human cancers. This makes it difficult to reconcile PP2A's role as a bona fide tumor suppressor with little evidence showing the profound and widespread alterations of PP2A subunits in human cancers.

Our study now identifies that the epigenetic loss of a specific subunit of PP2A, encoded by PPP2R2B, occurs uniformly in >90% of colorectal tumor samples. In addition to colorectal cancer, PPP2A2B may also be downregulated in other cancers such as bladder, brain and esophagus carcinoma, as revealed by Oncomine database.

Thus, considering the low frequency of PP2A mutations among various subunits (<15%), the epigenetic mechanism leading to gene repression may play a more dominant role in PP2A inactivation in human cancer like CRC.

Example 24

Discussion—the Molecular Mechanism of PPP2R2B-PP2A Mediated Tumor Suppression

Due to the substrate diversity of PP2A regulatory subunits, it is not surprising to see numerous oncogenic signaling pathways affected in various tissues or cellular contexts. We hypothesize that the loss of PPP2R2B associated specific PP2A complex may promote the deregulation of certain oncogene signaling pathways required for CRC cell survival and proliferation.

We identify Myc as a crucial downstream target of PPP2R2B that plays a role in mediating the tumor suppressor effect of PPP2R2B. This is in agreement with a crucial role of Myc in CRC tumorigenesis (Sansom et al., 2007). Although PPP2R2B has no discernable effect on Wnt pathway in CRC cells, it regulates Myc phosphorylation and protein accumulation. Thus its effect on Myc is consistent with the strong growth inhibition effect of PPP2R2B on CRC cells that are addicted to Wnt pathway for growth advantage.

Although a distinct PP2A subunit B56α has been shown to associate with Myc and regulates its stability (Arnold and Sears, 2006; Junttila et al., 2007), we were unable to detect the interaction between PPP2R2B-PP2A (B55β) with Myc. Indeed, we show that PPP2R2B regulation of Myc routes through PDK1 as PPP2R2B binds to PDK1 and affects PDK1 activity towards Myc phosphorylation.

PDK1 is considered as master regulator of PI3K signaling as no upstream kinase has been identified thus far. Thus identification of protein phosphatase-based regulation seems to be consistent with a regulatory mechanism of this master kinase regulator.

Thus, in addition to PIK3CA or PTEN mutations that occur in 50% of CRC, loss of PPP2R2B might provide a more prevalent mechanism leading to deregulation of PDK1. We thus identified an epigenetic mechanism contributing to the activation of the PDK1-Myc signaling in CRC.

Example 25

Discussion—the Role of PDK1-Myc Vs. PIK3CA-AKT in Rapamycin Resistance

Our study reveals a novel function of PDK1 toward Myc regulation in response to rapamycin. This PDK1-Myc signaling is independent of PIK3CA-AKT and may constitute an alternative feedback mechanism leading to rapamycin resistance.

Although we demonstrate Myc as a downstream target of PDK1, PDK1 may not regulate Myc directly. It is possible that PDK1 may route through other downstream kinases to affect Myc phosphorylation. The precise feedback mechanism leading to the induction of Myc phosphorylation by rapamycin remains unclear and warrants further investigation.

Although PIK3CA and mTORC2-dependent AKT 5473 phosphorylation has been suggested to be one crucial mechanism accounting for the rapamycin resistance in certain contexts (O'Reilly et al., 2006; Sarbassov et al., 2006), this pathway in CRC may not be as critical as rapamycin-induced Myc phosphorylation for rapamycin resistance, as knockdown of PIK3CA or AKT, does not sensitize rapamycin. As such, we propose an AKT-independent signaling module comprised of PDK1 and Myc phosphorylation contributing to rapamycin resistance in CRC, due to loss of PPP2R2B. This notion seems to be consistent with a recent finding that AKT is often not required for proliferation of cancer cells with activated PI3K pathway (Vasudevan et al., 2009). Thus, the identification of a PDK1-Myc signaling regulated by PPP2R2B widens our understanding of cancer cell growth control and rapamycin resistance and emphasizes the importance of epigenetic mechanisms in regulating oncogenic signaling and therapeutic response.

Example 26

Discussion—Clinical and Therapeutic Implications

Several rapamycin analogs have been under the clinical development (Easton and Houghton, 2006; Faivre et al., 2006; Granville et al., 2006).

Unfortunately, clinical updates indicate that rapamycin shows promise against only a few cancers, particularly mantel cell lymphoma, endometrial cancer, and renal cell carcinoma.

Overall, the therapeutic response to rapamycin is highly variable, indicating the strong need for biomarkers that are capable of predicting the therapeutic effect of rapamycin. Our data suggest PPP2R2B promoter methylation may be an epigenetic event that impacts the sensitivity of cancer cells to mTOR inhibitors.

This finding may have important implications for clinical trials of rapamycin derivatives in human cancer: PPP2R2B could serve as one of the predictive markers for patient selection, while Myc phosphorylation can be used a surrogate marker to evaluate the drug response.

Finally, our data support PDK1 as a therapeutic target in CRC as removal of PDK1 reduces Myc signaling and alleviate rapamycin resistance. This notion was further illustrated using a small molecule PDK1 inhibitor BX912, which is able to abolish rapamycin-induced Myc phosphorylation and thus synergizes with rapamycin in CRC. Notably, the PDK1 inhibitor as an anti-cancer agent has been shown to be effective in vitro and in vivo in cancer (Maurer et al., 2009; Peifer and Alessi, 2008) and is currently under clinical development. Therefore, we propose that its combination with rapamycin-based mTORC1 inhibitors may become a useful option for targeted therapy of CRC.

Example 27

PLK1 as a Crucial Kinase Mediating PDK1-Directal Transformation

We have shown above that PDK1 induces Myc phosphorylation and this effect may be mediated indirectly by additional kinases. To identify the kinases in the PDK1 route that might be crucial for Myc phosphorylation, we performed small molecule kinase inhibitor screens in HEK-PDK1 and HEK-control cells to identify those that are more selectively affect PDK1 cells than the control cells.

Figure 17:
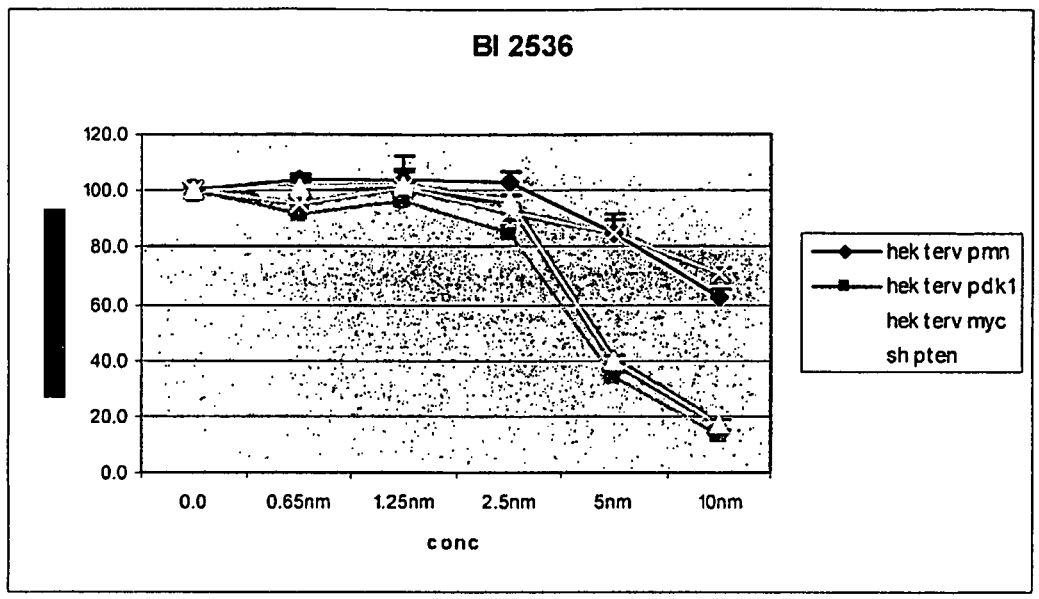
FIG. 17. PLK1 inhibitors BI2536 and GW843682X more selectively decrease the cell viability of PDK1 or Myc-transformed cells, compared to control or PTEN stable knockdown induced transformation. The cell viability assay was carried out in the presence of PLK1 inhibitors for 4 days.
Figure 17:
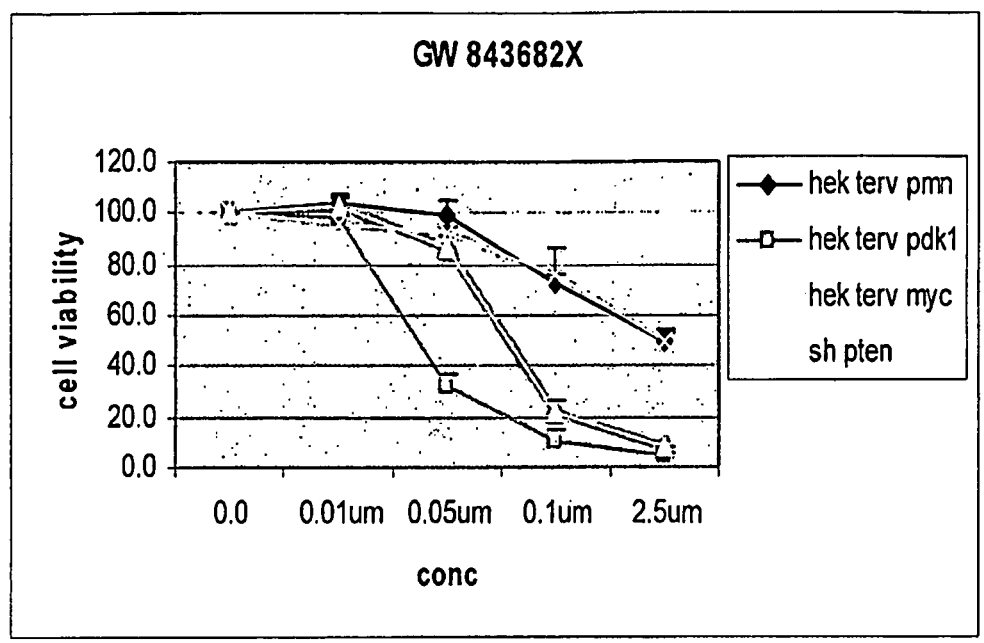

Two PLK1 kinase inhibitors BI2136 and GW843682X exhibited selective growth inhibition effect on HEK-PDK1 cells as compared to the HEK-vector control cells (PMN). More careful dose-response analysis in HEK-PMN control, HEK-PDK1, HEK-Myc and HEK-shPTEN (PTEN knockdown by small hairpin RNA) cells further validated this finding and showed that BI2536 and GW843682X more selectively inhibit the proliferation of PDK1 or Myc-transformed HEK cells, but HEK-PMN and HEK-shPTEN cells (FIG. 17).

This finding indicates that PLK1 may be crucial for growth advantage of PDK1-transformed cells, but not required for cells transformed with PI3K-AKT activation (PTEN knockdown).

Figure 18:
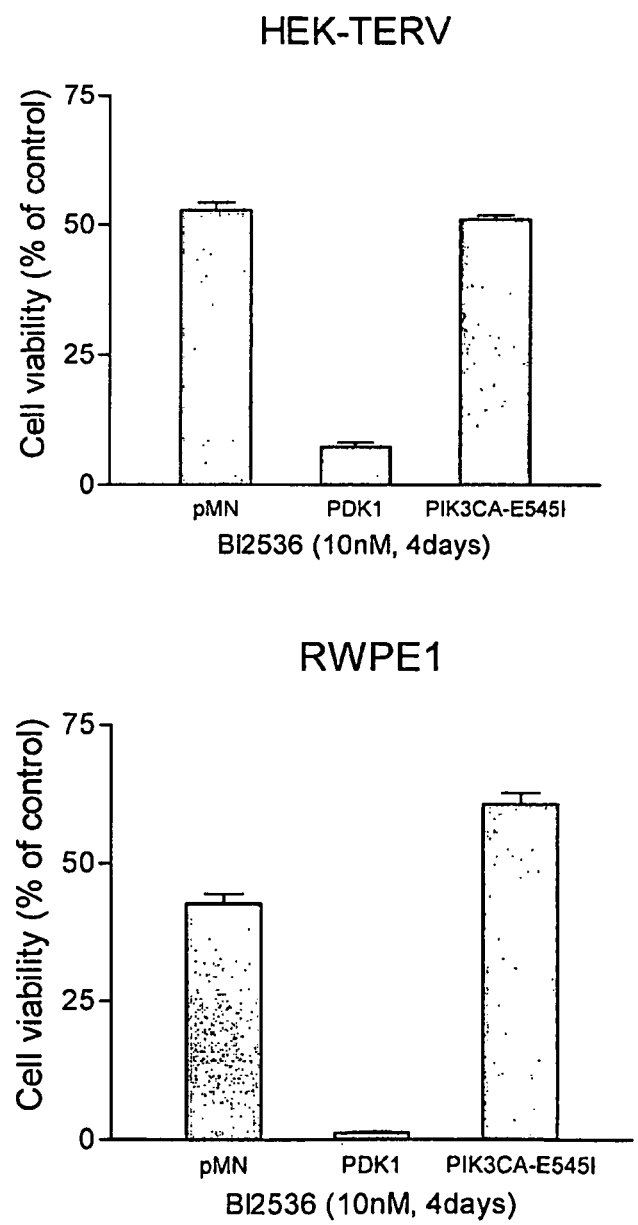
FIG. 18. The PLK1 inhibitor BI2536 preferentially inhibits the proliferation of PDK1 transformed cells, but has less effect on control cells (PMN) and PI3K transformed cells (E545) in both HEK-TERV and RWPE1 systems FIG. 19. Apoptotic assay in HEK-TERV cells treated with PLK1 inhibitor BI2536 10 nM for 24 h.

This conclusion was further validated in another cellular model using prostate epithelial cells (RWPE) transformed with PDK1 or P3KE545K (constitutively activated PI3K) (FIG. 18).

Figure 19:
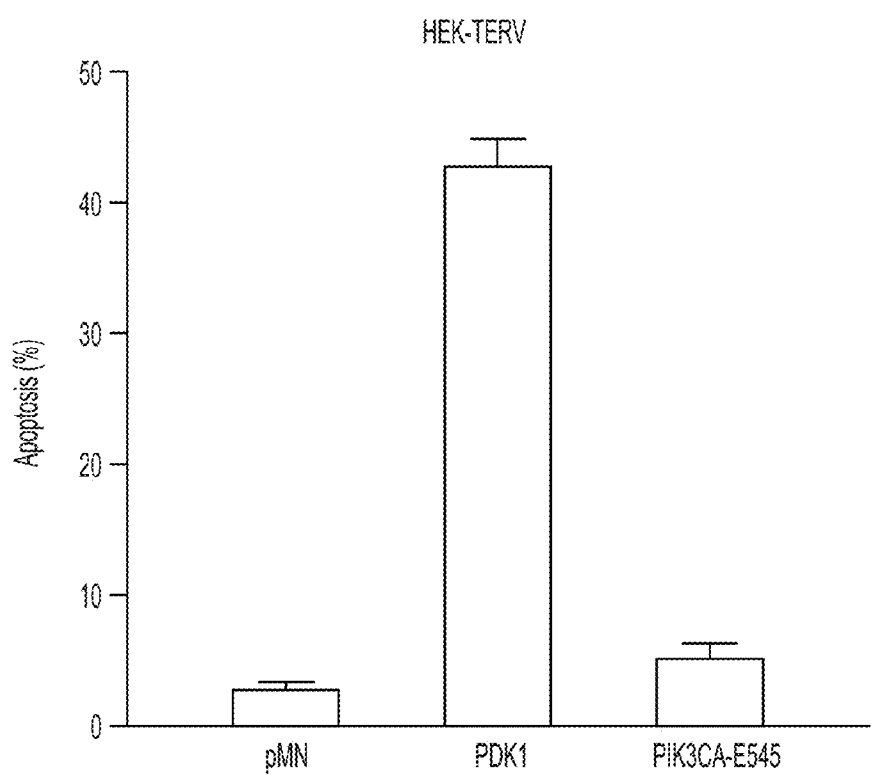
Figure 20A:
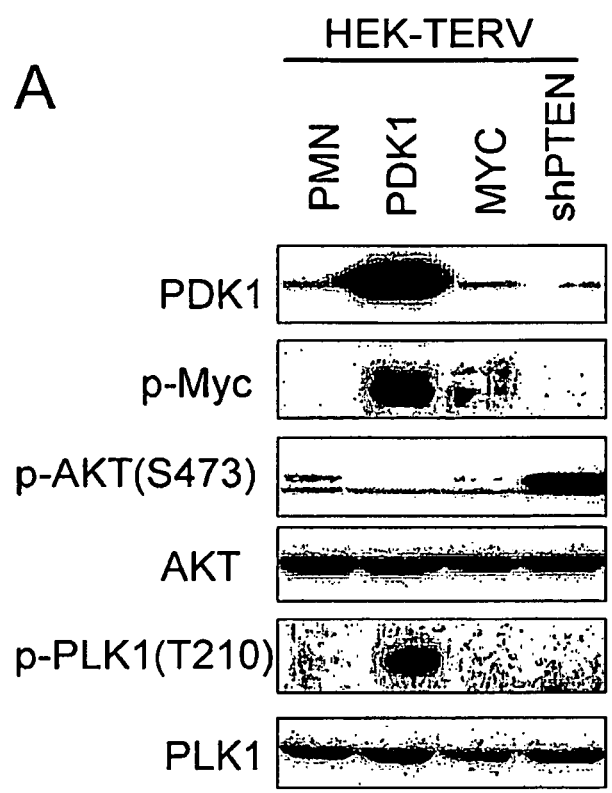
FIGS. 20A-20B. PDK1 induces PLK1 and Myc phosphorylation in multiple epithelial cells.
Figure 20B:
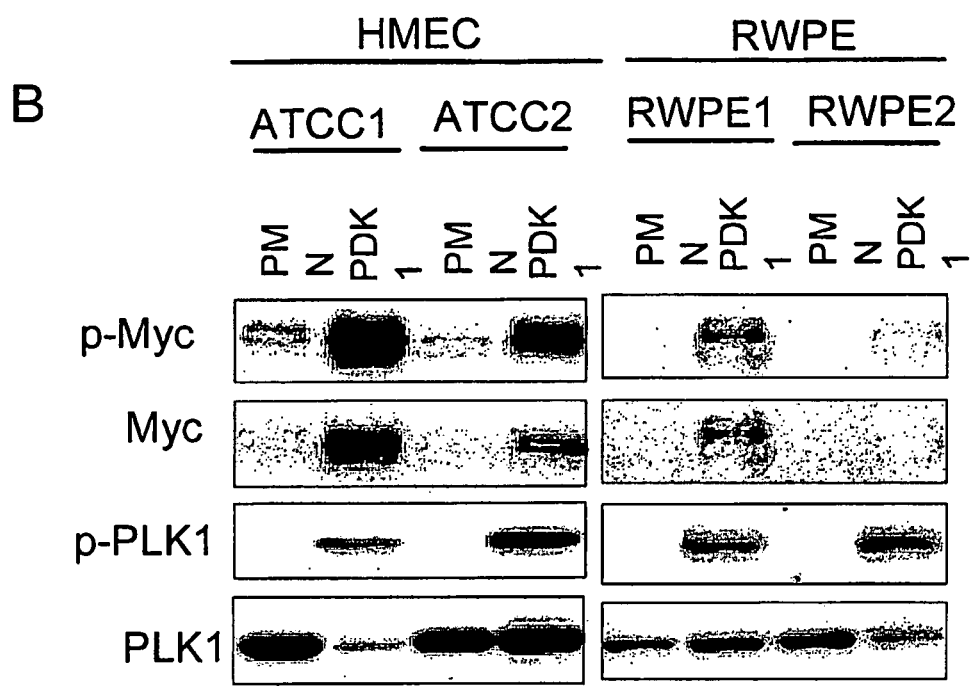

Furthermore, PLK1 inhibitor BI2536 selectively induced apoptosis in PDK1-transformed cells, but not in control or PI3K (E545)-transformed cells (FIG. 19). Taken together, these findings suggest a crucial role of PLK1 in PDK1-driven transformation.

Example 28

PDK1 Induces PLK1 Phosphorylation in Multiple Cellular Systems

Consistent with the above effects of PLK1 inhibitors on PDK1-transformed cells, Western blot analysis shows the induction of PLK1 phosphorylation, concomitant with induced Myc phosphorylation in PDK1 transformed HEK, RWPE and HMEC cells, but not in shPTEN cells.

These findings indicate that PDK1 activation results in PLK1 and Myc phosphorylation, but activation of PI3K-AKT pathway failed to do so.

Example 29

PLK1 is an Upstream Kinase Modulates Myc Phosphorylation

Figure 21:
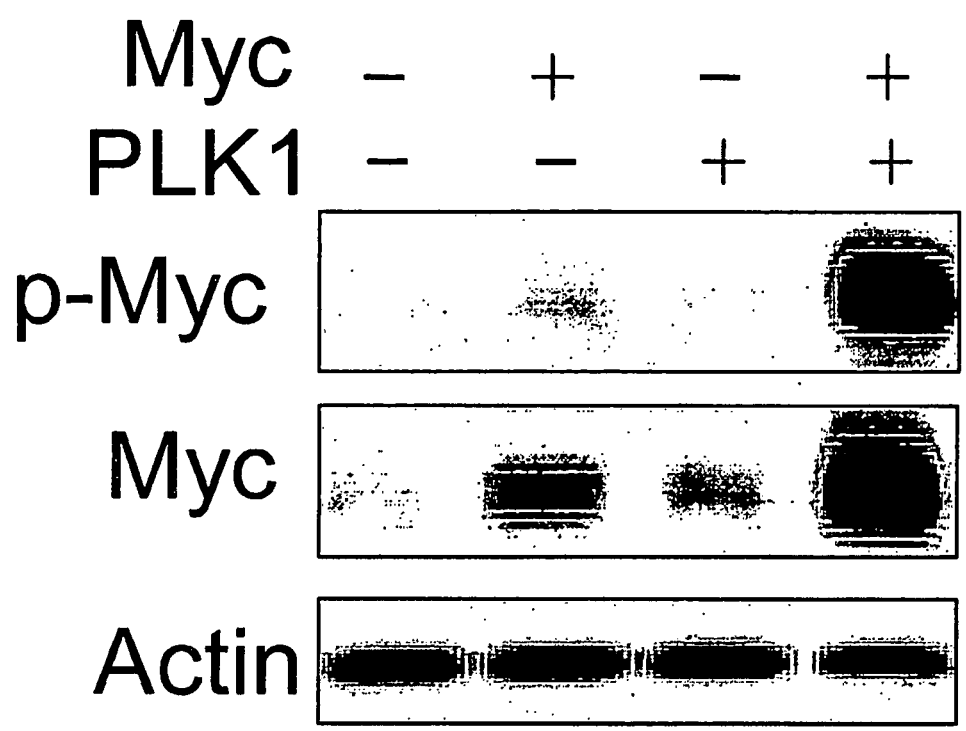
FIG. 21. PLK1 overexpression induces Myc phosphorylation and accumulates Myc protein in 293T cell.

To assess whether PLK1 overexpression is sufficient to induce Myc phosphorylation, we cotransfected 293T cells with PLK1 and Myc plasmids. The result shows that ectopic expression of PLK1 includes strong Myc phosphorylation (FIG. 21).

Figure 22:
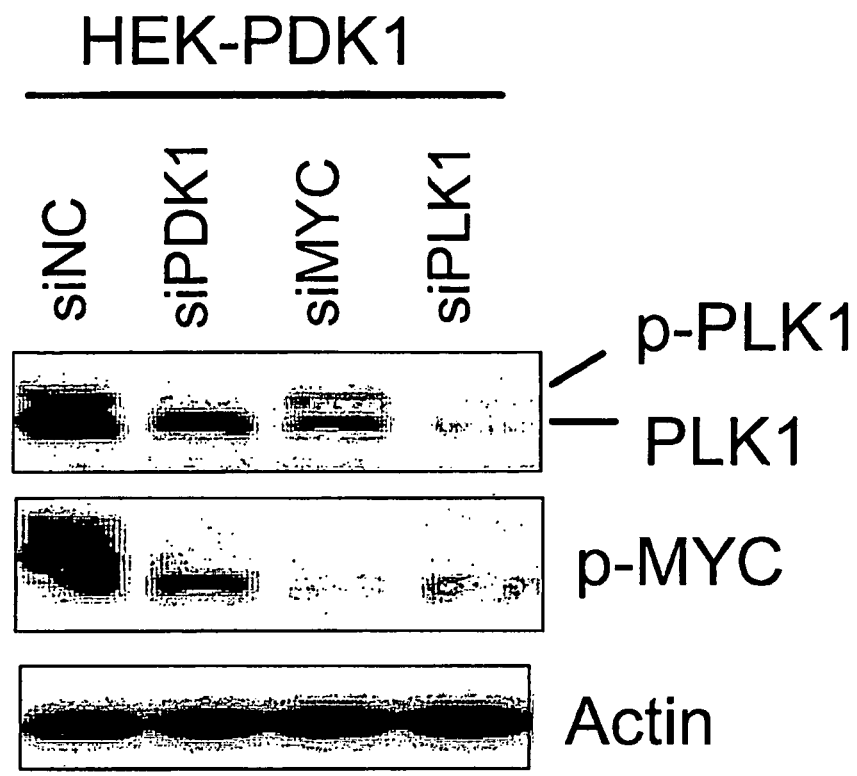
FIG. 22. PLK1 knockdown by siRNA suppresses Myc phosphorylation in HEK-PDK1 cells.

This validated PLK1 as an upstream regulator of Myc phosphorylation in PDK1-driven transformation. Conversely, knockdown PLK1 with siRNA abolished Myc phosphorylation in PDK1-transformed cells (FIG. 22).

Example 30 mTOR Inhibitor BEZ235-Induced Myc Phosphorylation in Colon Cancer Cells can be Abolished by PLK1 Inhibitor and Combination of PLK1 Inhibitor BI2536 with BEZ235 are Synergistic in Growth Inhibition and Apoptosis We have previously shown that mTOR inhibitor rapamycin induces PDK1-dependent Myc phosphorylation in colon cancer cells, which results in resistance to rapamycin.

Further more, we show that PDK1 inhibitor can block rapamycin-induced Myc phosphorylation and sensitizes rapamycin treatment.

Figure 23:
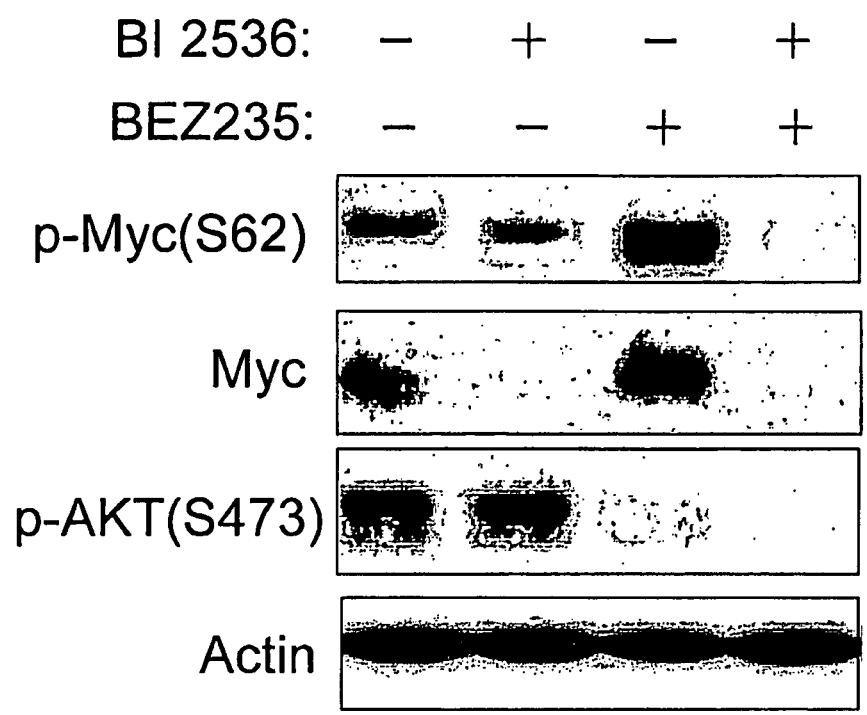
FIG. 23. BEZ 235-induced Myc phosphorylation required PLK1. Immunoblot analysis of Myc and AKT phosphorylation in DLD1 cells treated with PLK1 inhibitor BI2536 (10 nM), mTOR inhibitor BEZ 235 (100 nM) or indicated combination for 48 hr FIG. 24. Cell viability of SW480 and DLD1 cells treated with BI 2536 (10 nM), BEZ 235 (10 nM) or both for indicated days.

Now we show that mTOR inhibitor BEZ235 can also induced Myc phosphorylation and PLK1 inhibitor abolished this Myc induction (FIG. 23).

Figure 24:
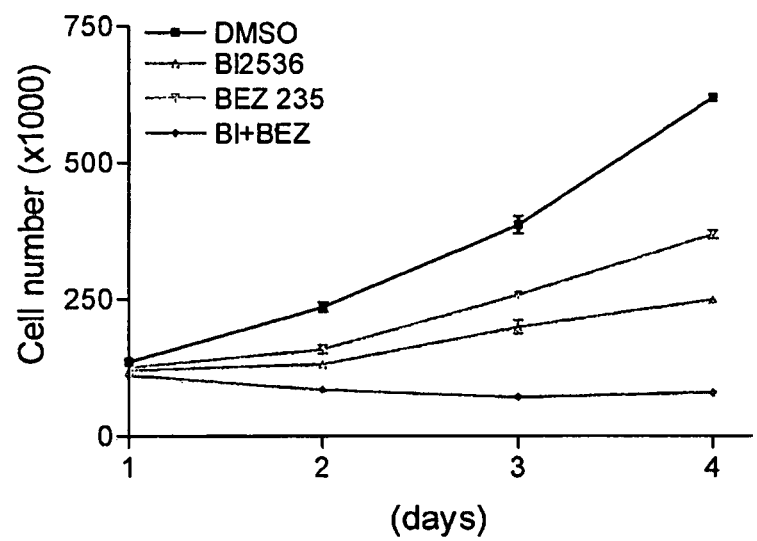
Figure 24:
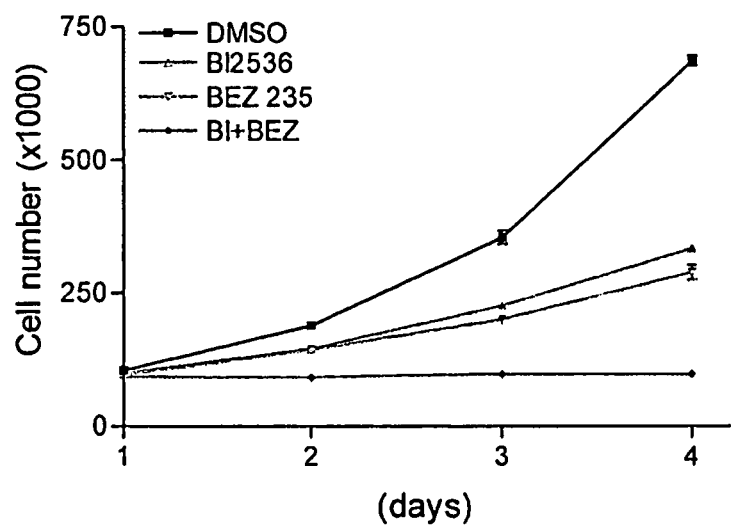
Figure 25:
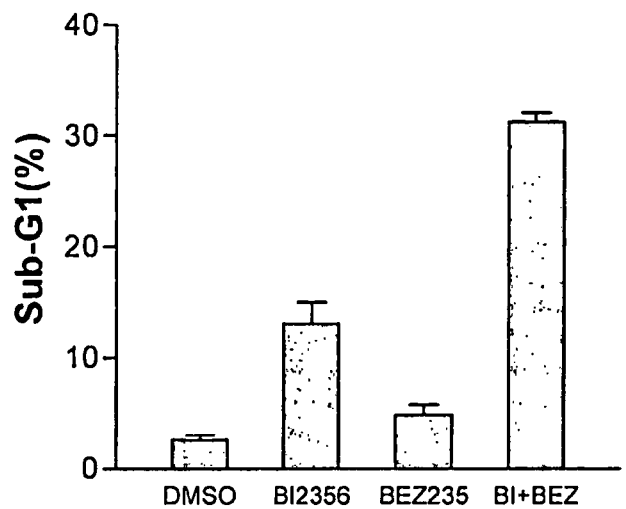
FIG. 25. Apoptotic assay in SW480 and DLD1 cells treated with BI2536 (10 nM), BEZ 235 (100 nM) or both for 48 hr.
Figure 25:
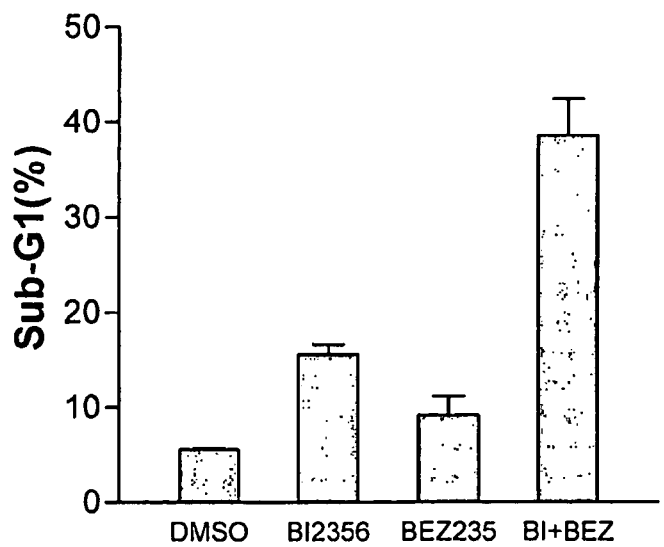
Figure 26:
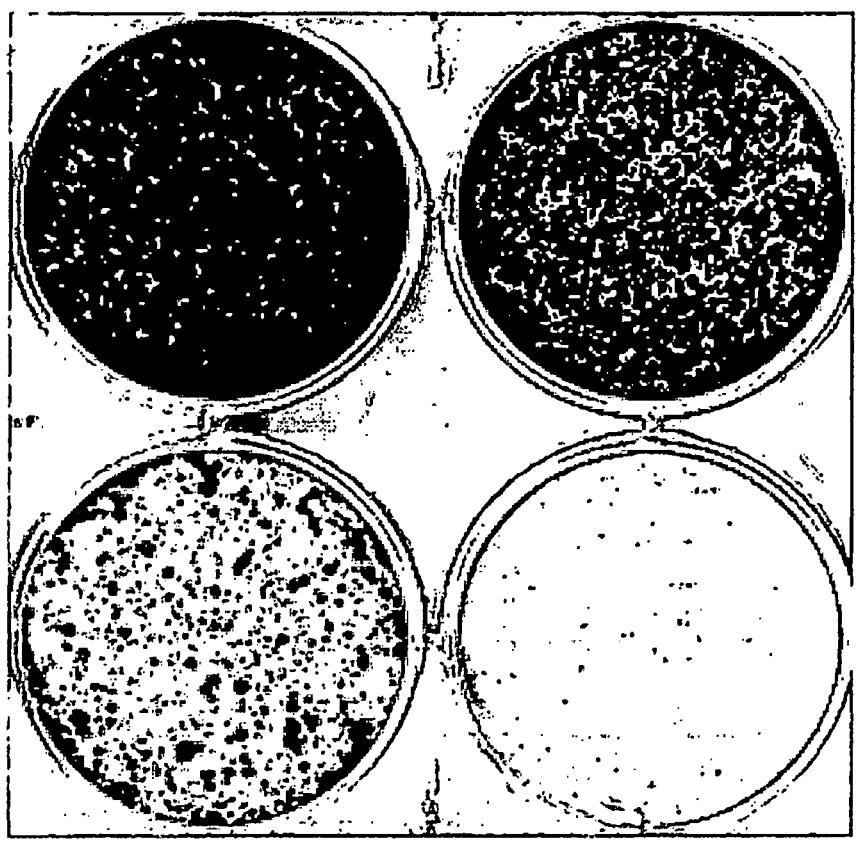
FIG. 26. Monolayer colony formation assay in DLD1 cells treated with BEZ 235 or BI2436 or combination for 12 days.

As a result, combination of BI2536 with BEZ235 triggers a strong synergistic growth inhibition (FIG. 24), apoptosis (FIG. 25) or long term colony formation (FIG. 26) in colon cancer cell lines SW480 and DLD1 cells.

Example 31

PDK1 Activates Cancer Stem Cell Program

Figure 27:
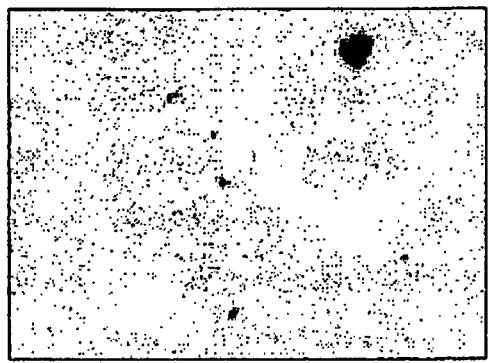
FIG. 27. PDK1 transformed cells generated a greater number of tumor spheres as compared with pMN control cells, PIK3CA-E545K or shPTEN-transformed cells.
Figure 27:
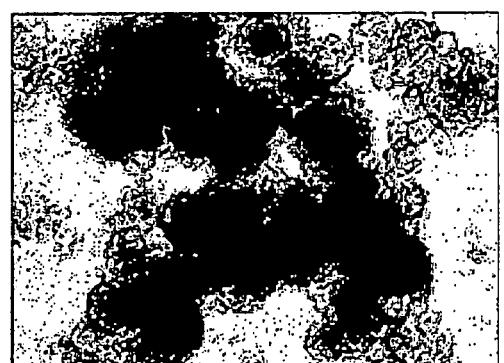
Figure 27:
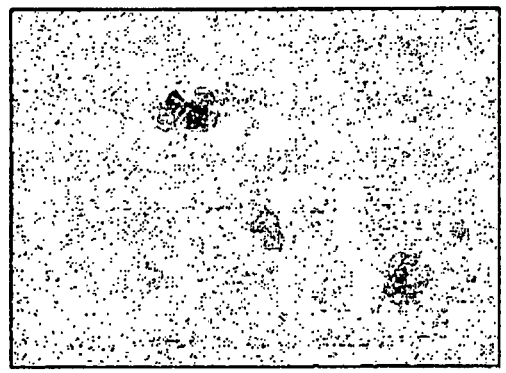
Figure 27:
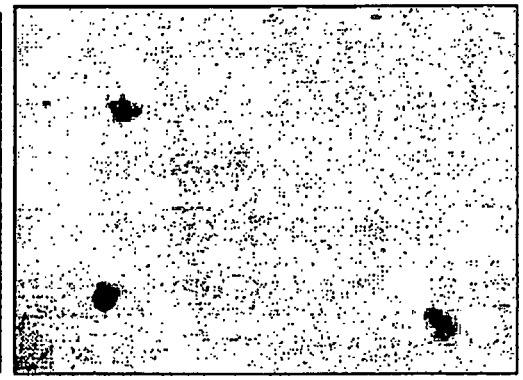
Figure 28:
FIG. 28. The PLK1 inhibitor BI2536 blocks the tumor sphere formation in HEK-PDK1 cells. The cells were treated with or without 5 nM BI2536 for 7 days.
Figure 28:
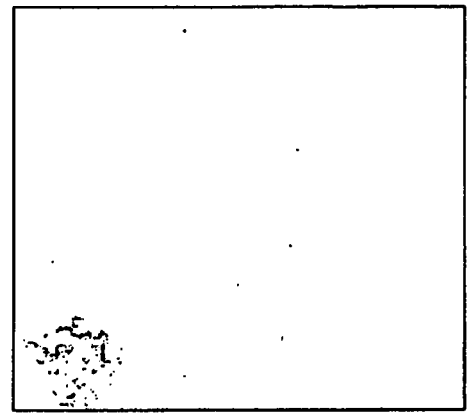
Figure 29:
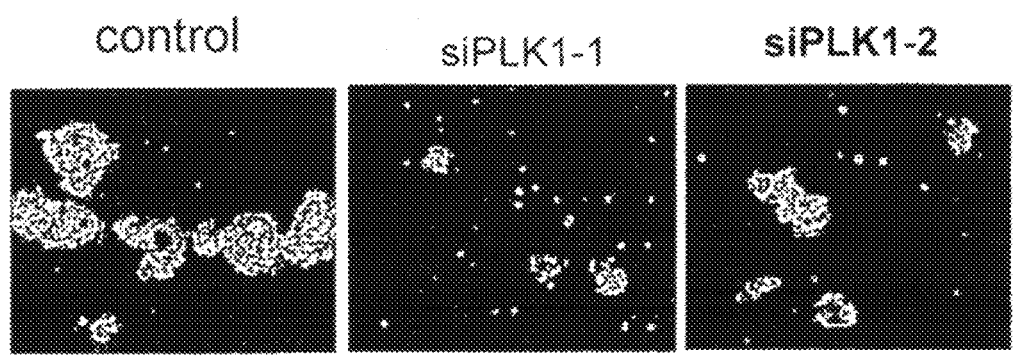
FIG. 29. PLK1 knockdown by siRNAs inhibit tumor sphere formation in HEK-PDK1 cells.

PDK1 driven transformation induces self-renewable tumor spheres formation, which is characteristics of cancer stem cells, while E454K and shPTEN-transformed cells failed to do so (FIG. 27). PLK1 inhibitor BI2536 treatment (FIG. 28) or PLK1 knockdown (FIG. 29) abolished the PDK1-driven tumorspheres formation.

Figure 30:
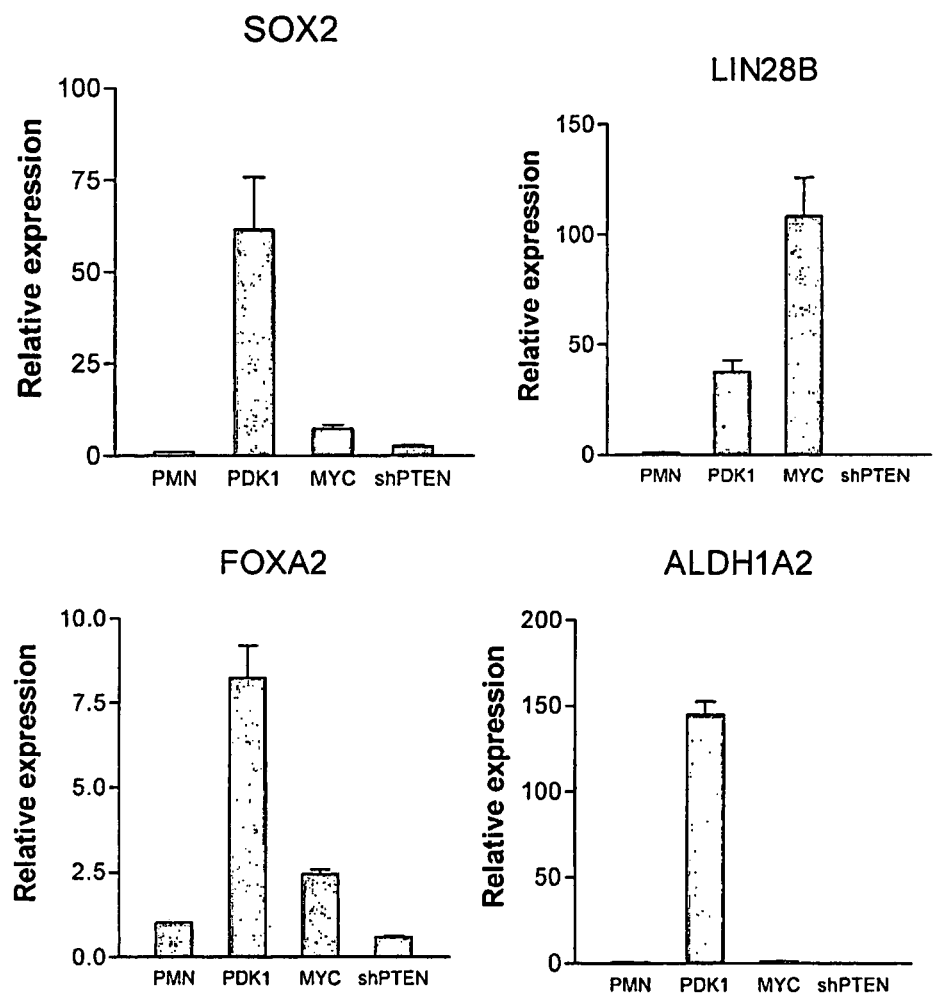
FIG. 30. qRT-PCR analysis was performed for stem cell-associated genes in HEK-TERV cells.

In addition, PDK1 activates the expression of stem cell factors such as Sox2, Lin28B, Aldh1A2, while shPTEN can not (FIG. 30).

Figure 31:
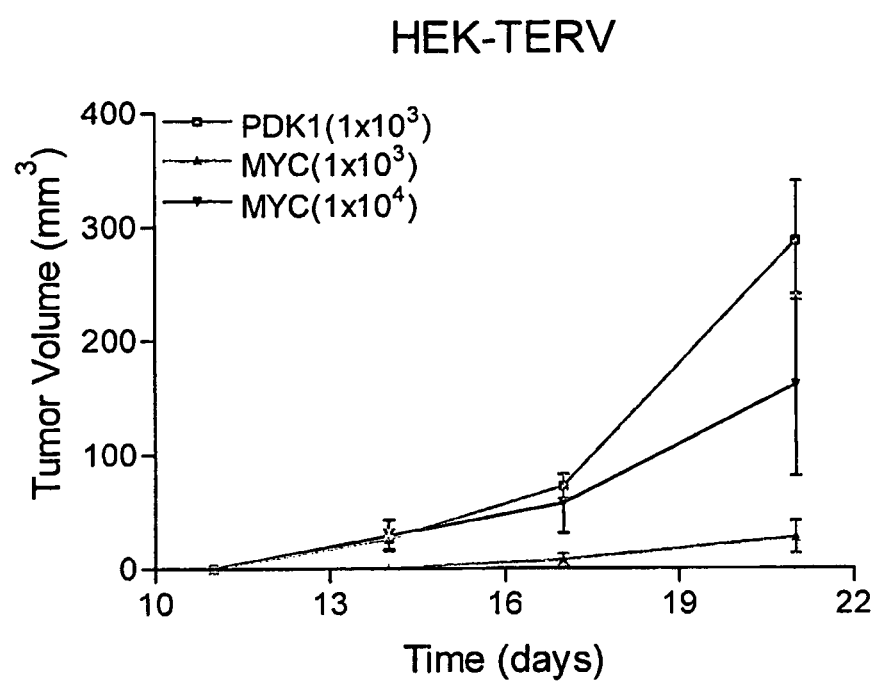
FIG. 31. Tumor growth curve (mean±SD) in nude mice 3 weeks after injection of 1000 HEK-PDK1 cells as compared with $1\times10^3$ or $1\times10^4$ HEK-Myc cells.

Finally, 1000 PDK1 transformed cells are sufficient to induce robust xenograft tumor formation in NOD/SCID mice, while 10-fold more Myc cells are required to give rise to tumors (FIG. 31), validating PDK-transformed cells are highly tumorigenic and can induce cancer stem cells formation.

REFERENCES

Andrabi, S., Gjoerup, O. V., Kean, J. A., Roberts, T. M., and Schaffhausen, B. (2007). Protein phosphatase 2A regulates life and death decisions via Akt in a context-dependent manner. Proc Natl Acad Sci USA 104, 19011-19016.

Arnold, H. K., and Sears, R. C. (2006). Protein phosphatase 2A regulatory subunit B56alpha associates with c-myc and negatively regulates c-myc accumulation. Mol Cell Biol 26, 2832-2844.

Arnold, H. K., and Sears, R. C. (2008). A tumor suppressor role for PP2A-B56alpha through negative regulation of c-Myc and other key oncoproteins. Cancer Metastasis Rev 27, 147-158.

Calin, G. A., di Iasio, M. G., Caprini, E., Vorechovsky, I., Natali, P. G., Sozzi, G., Croce, C. M., Barbanti-Brodano, G., Russo, G., and Negrini, M. (2000). Low frequency of alterations of the alpha (PPP2R1A) and beta (PPP2R1B) isoforms of the subunit A of the serine-threonine phosphatase 2A in human neoplasms. Oncogene 19, 1191-1195.

Cappellen, D., Schlange, T., Bauer, M., Maurer, F., and Hynes, N. E. (2007). Novel c-MYC target genes mediate differential effects on cell proliferation and migration. EMBO Rep 8, 70-76.

Chen, W., Arroyo, J. D., Timmons, J. C., Possemato, R., and Hahn, W. C. (2005). Cancer-associated PP2A Aalpha subunits induce functional haploinsufficiency and tumorigenicity. Cancer Res 65, 8183-8192.

Chen, W., Possemato, R., Campbell, K. T., Plattner, C. A., Pallas, D. C., and Hahn, W. C. (2004). Identification of specific PP2A complexes involved in human cell transformation. Cancer Cell 5, 127-136.

Easton, J. B., and Houghton, P. J. (2006). mTOR and cancer therapy. Oncogene 25, 6436-6446.

Eichhorn, P. J., Creyghton, M. P., and Bernards, R. (2009). Protein phosphatase 2A regulatory subunits and cancer. Biochim Biophys Acta 1795, 1-15.

Faivre, S., Kroemer, G., and Raymond, E. (2006). Current development of mTOR inhibitors as anticancer agents. Nat Rev Drug Discov 5, 671-688.

Fan, Q. W., Knight, Z. A., Goldenberg, D. D., Yu, W., Mostov, K. E., Stokoe, D., Shokat, K. M., and Weiss, W. A. (2006). A dual PI3 kinase/mTOR inhibitor reveals emergent efficacy in glioma. Cancer Cell 9, 341-349.

Feldman, R. I., Wu, J. M., Polokoff, M. A., Kochanny, M. J., Dinter, H., Zhu, D., Biroc, S. L., Alicke, B., Bryant, J., Yuan, S., et al. (2005). Novel small molecule inhibitors of 3-phosphoinositide-dependent kinase-1. J Biol Chem 280, 19867-19874.

Granville, C. A., Memmott, R. M., Gills, J. J., and Dennis, P. A. (2006). Handicapping the race to develop inhibitors of the phosphoinositide 3-kinase/Akt/mammalian target of rapamycin pathway. Clin Cancer Res 12, 679-689.

Guertin, D. A., and Sabatini, D. M. (2007). Defining the role of mTOR in cancer. Cancer Cell 12, 9-22.

Hahn, W. C., Dessain, S. K., Brooks, M. W., King, J. E., Elenbaas, B., Sabatini, D. M., DeCaprio, J. A., and Weinberg, R. A. (2002). Enumeration of the simian virus 40 early region elements necessary for human cell transformation. Mol Cell Biol 22, 2111-2123.

Heinonen, H., Nieminen; A., Saarela, M., Kallioniemi, A., Klefstrom, J., Hautaniemi, S., and Monni, O. (2008). Deciphering downstream gene targets of PI3K/mTOR/p70S6K pathway in breast cancer. BMC Genomics 9, 348.

Hudes, G., Carducci, M., Tomczak, P., Dutcher, J., Figlin, R., Kapoor, A., Staroslawska, E., Sosman, J., McDermott, D., Bodrogi, I., et al. (2007). Temsirolimus, interferon alfa, or both for advanced renal-cell carcinoma. N Engl J Med 356, 2271-2281.

Janssens, V., and Goris, J. (2001). Protein phosphatase 2A: a highly regulated family of serine/threonine phosphatases implicated in cell growth and signalling. Biochem J 353, 417-439.

Jia, S., Liu, Z., Zhang, S., Liu, P., Zhang, L., Lee, S. H., Zhang, J., Signoretti, S., Loda, M., Roberts, T. M., et al. (2008). Essential roles of PI(3)K-p110beta in cell growth, metabolism and tumorigenesis. Nature 454, 776-779.

Jiang, X., Tan, J., Li, J., Kivimae, S., Yang, X., Zhuang, L., Lee, P. L., Chan, M. T., Stanton, L. W., Liu, E. T., et al. (2008). DACT3 is an epigenetic regulator of Wnt/beta-catenin signaling in colorectal cancer and is a therapeutic target of histone modifications. Cancer Cell 13, 529-541.

Junttila, Puustinen, P., Niemela, M., Ahola, R., Arnold, H., Bottzauw, T., Ala-aho, R., Nielsen, C., Ivaska, J., Taya, Y., et al., (2007). CIP2A inhibits PP2A in human malignancies. Cell 130, 51-62.

Kikani, C. K., Dong, L. Q., and Liu, F. (2005). "New"-clear functions of PDK1: beyond a master kinase in the cytosol? J Cell Biochem 96, 1157-1162.

Knight, Z. A., Gonzalez, B., Feldman, M. E., Zunder, E. R., Goldenberg, D. D., Williams, O., Loewith, R., Stokoe, D., Balla, A., Toth, B., et al. (2006). A pharmacological map of the PI3-K family defines a role for p110alpha in insulin signaling. Cell 125, 733-747.

Korinek, V., Barker, N., Morin, P. J., van Wichen, D., de Weger, R., Kinzler, K. W., Vogelstein, B., and Clevers, H. (1997). Constitutive transcriptional activation by a beta-catenin-Tcf complex in APC−/− colon carcinoma. Science 275, 1784-1787.

Kuo, Y. C., Huang, K. Y., Yang, C. H., Yang, Y. S., Lee, W. Y., and Chiang, C. W. (2008). Regulation of phosphorylation of Thr-308 of Akt, cell proliferation, and survival by the B55alpha regulatory subunit targeting of the protein phosphatase 2A holoenzyme to Akt. J Biol Chem 283, 1882-1892.

Mao, J. H., Kim, I. J., Wu, D., Climent, J., Kang, H. C., DelRosario, R., and Balmain, A. (2008). FBXW7 targets mTOR for degradation and cooperates with PTEN in tumor suppression. Science 321, 1499-1502.

Maurer, M., Su, T., Saal, L. H., Koujak, S., Hopkins, B. D., Barkley, C. R., Wu, J., Nandula, S., Dutta, B., Xie, Y., et al. (2009). 3-Phosphoinositide-dependent kinase 1 potentiates upstream lesions on the phosphatidylinositol 3-kinase pathway in breast carcinoma. Cancer Res 69, 6299-6306.

Morin, P. J., Sparks, A. B., Korinek, V., Barker, N., Clevers, H., Vogelstein, B., and Kinzler, K. W. (1997). Activation of beta-catenin-Tcf signaling in colon cancer by mutations in beta-catenin or APC. Science 275, 1787-1790.

O'Reilly, K. E., Rojo, F., She, Q. B., Solit, D., Mills, G. B., Smith, D., Lane, H., Hofmann, F., Hicklin, D. J., Ludwig, D. L., et al. (2006). mTOR inhibition induces upstream receptor tyrosine kinase signaling and activates Akt. Cancer Res 66, 1500-1508.

Padmanabhan, S., Mukhopadhyay, A., Narasimhan, S. D., Tesz, G., Czech, M. P., and Tissenbaum, H. A. (2009). A PP2A regulatory subunit regulates *C. elegans* insulin/IGF-1 signaling by modulating AKT-1 phosphorylation. Cell 136, 939-951.

Peifer, C., and Alessi, D. R. (2008). Small-molecule inhibitors of PDK1. ChemMedChem 3, 1810-1838.

Peterson, R. T., Desai, B. N., Hardwick, J. S., and Schreiber, S. L. (1999). Protein phosphatase 2A interacts with the 70-kDa S6 kinase and is activated by inhibition of FKBP12-rapamycinassociated protein. Proc Natl Acad Sci USA 96, 4438-4442.

Rangarajan, A., Hong, S. J., Gifford, A., and Weinberg, R. A. (2004). Species- and cell type-specific requirements for cellular transformation. Cancer Cell 6, 171-183.

Ruediger, R., Pham, H. T., and Walter, G. (2001). Alterations in protein phosphatase 2A subunit interaction in human carcinomas of the lung and colon with mutations in the A beta subunit gene. Oncogene 20, 1892-1899.

Sabatini, D. M. (2006). mTOR and cancer: insights into a complex relationship. Nat Rev Cancer 6, 729-734.

Sablina, A. A., Chen, W., Arroyo, J. D., Corral, L., Hector, M., Bulmer, S. E., DeCaprio, J. A., and Hahn, W. C. (2007). The tumor suppressor PP2A Abeta regulates the RalA GTPase. Cell 129, 969-982.

Sansom, O. J., Meniel, V. S., Muncan, V., Phesse, T. J., Wilkins, J. A., Reed, K. R., Vass, J. K., Athineos, D., Clevers, H., and Clarke, A. R. (2007). Myc deletion rescues Apc deficiency in the small intestine. Nature 446, 676-679.

Sarbassov, D. D., Ali, S. M., Sengupta, S., Sheen, J. H., Hsu, P. P., Bagley, A. F., Markhard, A. L., and Sabatini, D. M. (2006). Prolonged rapamycin treatment inhibits mTORC2 assembly and Akt/PKB. Mol Cell 22, 159-168.

Sarbassov, D. D., Guertin, D. A., Ali, S. M., and Sabatini, D. M. (2005). Phosphorylation and regulation of Akt/PKB by the rictor-mTOR complex. Science 307, 1098-1101.

Sawyers, C. L. (2008). The cancer biomarker problem. Nature 452, 548-552.

Scott, K. L., Kabbarah, O., Liang, M. C., Ivanova, E., Anagnostou, V., Wu, J., Dhakal, S., Wu, M., Chen, S., Feinberg, T., et al. (2009). GOLPH3 modulates mTOR signalling and rapamycin sensitivity in cancer. Nature 459, 1085-1090.

Seeling, J. M., Miller, J. R., Gil, R., Moon, R. T., White, R., and Virshup, D. M. (1999). Regulation of beta-catenin signaling by the B56 subunit of protein phosphatase 2A. Science 283, 2089-2091.

Sekulic, A., Hudson, C. C., Homme, J. L., Yin, P., Otterness, D. M., Karnitz, L. M., and Abraham, R. T. (2000). A direct linkage between the phosphoinositide 3-kinase-AKT signaling pathway and the mammalian target of rapamycin in mitogen-stimulated and transformed cells. Cancer Res 60, 3504-3513.

Sontag, E., Fedorov, S., Kamibayashi, C., Robbins, D., Cobb, M., and Mumby, M. (1993). The interaction of SV40 small tumor antigen with protein phosphatase 2A stimulates the map kinase pathway and induces cell proliferation. Cell 75, 887-897.

Su, Y., Fu, C., Ishikawa, S., Stella, A., Kojima, M., shitoh, K., Schreiber, E. M., Day, B. W., and Liu, B. (2008). APC is essential for targeting phosphorylated beta-catenin to the SCFbeta-TrCP ubiquitin ligase. Mol Cell 32, 652-661.

Takagi, Y., Futamura, M., Yamaguchi, K., Aoki, S., Takahashi, T., and Saji, S. (2000). Alterations of the PPP2R1B gene located at 11q23 in human colorectal cancers. Gut 47, 268-271.

Tamaki, M., Goi, T., Hirono, Y., Katayama, K., and Yamaguchi, A. (2004). PPP2R1B gene alterations inhibit interaction of PP2A-Abeta and PP2A-C proteins in colorectal cancers. Oncol Rep 11, 655-659.

Thomas, G. V., Tran, C., Mellinghoff, I. K., Welsbie, D. S., Chan, E., Fueger, B., Czernin, J., and Sawyers, C. L. (2006). Hypoxia-inducible factor determines sensitivity to inhibitors of mTOR in kidney cancer. Nat Med 12, 122-127.

Vasudevan, K. M., Barbie, D. A., Davies, M. A., Rabinovsky, R., McNear, C. J., Kim, J. J., Hennessy, B. T., Tseng, H., Pochanard, P., Kim, S. Y., et al. (2009). AKT-independent signaling downstream of oncogenic PIK3CA mutations in human cancer. Cancer Cell 16, 21-32.

Virshup, D. M., and Shenolikar, S. (2009). From promiscuity to precision: protein phosphatases get a makeover. Mol Cell 33, 537-545.

Wang, S. S., Esplin, E. D., Li, J. L., Huang, L., Gazdar, A., Minna, J., and Evans, G. A. (1998). Alterations of the PPP2R1B gene in human lung and colon cancer. Science 282, 284-287.

Westermarck, J., and Hahn, W. C. (2008). Multiple pathways regulated by the tumor suppressor PP2A in transformation. Trends Mol Med 14, 152-160.

Yeh, E., Cunningham, M., Arnold, H., Chasse, D., Monteith, T., Ivaldi, G., Hahn, W. C., Stukenberg, P. T., Shenolikar, S., Uchida, T., et al. (2004). A signalling pathway controlling c-Myc degradation that impacts oncogenic transformation of human cells. Nat Cell Biol 6, 308-318.

Zhao, J. J., Cheng, H., Jia, S., Wang, L., Gjoerup, O. V., Mikami, A., and Roberts, T. M. (2006). The p110alpha isoform of PI3K is essential for proper growth factor signaling and oncogenic transformation. Proc Natl Acad Sci USA 103, 16296-16300.

Zhao, J. J., Gjoerup, O. V., Subramanian, R. R., Cheng, Y., Chen, W., Roberts, T. M., and Hahn, W. C. (2003). Human mammary epithelial cell transformation through the activation of phosphatidylinositol 3-kinase. Cancer Cell 3, 483-495.

Alizadeh, A. A., Eisen, M. B., Davis, R. E., Ma, C., Lossos, I. S., Rosenwald, A., Boldrick, J. C., Sabet, H., Tran, T., Yu, X., et al. (2000). Distinct types of diffuse large B-cell lymphoma identified by gene expression profiling. Nature 403, 503-511.

Boer, J. M., Huber, W. K., Sultmann, H., Wilmer, F., von Heydebreck, A., Haas, S., Korn, B., Gunawan, B., Vente, A., Fuzesi, L., et al. (2001). Identification and classification of differentially expressed genes in renal cell carcinoma by expression profiling on a global human 31,500-element cDNA array. Genome Res 11, 1861-1870.

Chen, X., Cheung, S. T., So, S., Fan, S. T., Barry, C., Higgins, J., Lai, K. M., Ji, J., Dudoit, S., Ng, I. O., et al. (2002). Gene expression patterns in human liver cancers. Mol Biol Cell 13, 1929-1939.

Dyrskjot, L., Kruhoffer, M., Thykjaer, T., Marcussen, N., Jensen, J. L., Moller, K., and Orntoft, T. F. (2004). Gene expression in the urinary bladder: a common carcinoma in situ gene expression signature exists disregarding histopathological classification. Cancer Res 64, 4040-4048.

Hendrix, N. D., Wu, R., Kuick, R., Schwartz, D. R., Fearon, E. R., and Cho, K. R. (2006). Fibroblast growth factor 9 has oncogenic activity and is a downstream target of Wnt signaling in ovarian endometrioid adenocarcinomas. Cancer Res 66, 1354-1362.

Ki, D. H., Jeung, H. C., Park, C. H., Kang, S. H., Lee, G. Y., Lee, W. S., Kim, N. K., Chung, H. C., and Rha, S. Y. (2007). Whole genome analysis for liver metastasis gene signatures in colorectal cancer. Int J Cancer 121, 2005-2012.

Rickman, D. S., Bobek, M. P., Misek, D. E., Kuick, R., Blaivas, M., Kurnit, D. M., Taylor, J., and Hanash, S. M. (2001). Distinctive molecular profiles of high-grade and low-grade gliomas based on oligonucleotide microarray analysis. Cancer Res 61, 6885-6891.

Sanchez-Carbayo, M., Socci, N. D., Lozano, J., Saint, F., and Cordon-Cardo, C. (2006). Defining molecular profiles of poor outcome in patients with invasive bladder cancer using oligonucleotide microarrays. J Clin Oncol 24, 778-789.

Shai, R., Shi, T., Kremen, T. J., Horvath, S., Liau, L. M., Cloughesy, T. F., Mischel, P. S., and Nelson, S. F. (2003). Gene expression profiling identifies molecular subtypes of gliomas. Oncogene 22, 4918-4923.

Sun, L., Hui, A. M., Su, Q., Vortmeyer, A., Kotliarov, Y., Pastorino, S., Passaniti, A., Menon, J., Walling, J., Bailey, R., et al. (2006). Neuronal and glioma-derived stem cell factor induces angiogenesis within the brain. Cancer Cell 9, 287-300.

Wang, S., Zhan, M., Yin, J., Abraham, J. M., Mori, Y., Sato, F., Xu, Y., Olaru, A., Berki, A. T., Li, H., et al. (2006). Transcriptional profiling suggests that Barrett's metaplasia is an early intermediate stage in esophageal adenocarcinogenesis. Oncogene 2S, 3346-3356.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text; and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method comprising treating an individual suffering from or suspected to be suffering from a cancer with an mTOR inhibitor, wherein a cancer cell of the individual has been determined not to be mTOR inhibitor resistant by measuring expression and/or activity of (i) PPP2R2B or (ii) PDK1, or both, in or of the cancer cell, where a decreased expression and/or activity of PPP2R2B, or an increased expression and/or activity of PDK1, or both, compared to a cancer cell that is not mTOR inhibitor resistant, indicates that the cancer cell is resistant to treatment by an mTOR inhibitor.

2. A method according to claim 1, wherein the cancer is colorectal cancer (CRC).

3. A method according to claim 1, wherein the mTOR inhibitor comprises rapamycin or a derivative thereof.

4. A method according to claim 1, wherein the cancer is selected from the group consisting of: colorectal cancer (CRC), bladder cancer, brain cancer and oesophageal cancer.

5. A method comprising treating an individual suffering from or suspected to be suffering from a cancer with an mTOR inhibitor, wherein a cancer cell of the individual has been determined not to be mTOR inhibitor resistant by measuring methylation of the PPP2R2B promoter in or of the cancer cell, where hypermethylation of the PPP2R2B promoter, compared to a cancer cell that is not mTOR inhibitor resistant, indicates that the cancer cell is resistant to treatment by an mTOR inhibitor.

6. A method according to claim 1, where measuring expression and/or activity of PDK1 in or of the cancer cell comprised detecting PDK1 mediated Myc phosphorylation activity in or of the cancer cell.

7. A method comprising treating an individual suffering from or suspected to be suffering from a cancer with a therapy other than an mTOR inhibitor, wherein a cancer cell of the individual has been determined to be mTOR inhibitor resistant by measuring expression and/or activity of (i) PPP2R2B or (ii) PDK1, or both, in or of the cancer cell, where a decreased expression and/or activity of PPP2R2B, or an increased expression and/or activity of PDK1, or both, compared to a cancer cell that is not mTOR inhibitor resistant, indicates that the cancer cell is resistant to treatment by an mTOR inhibitor.

8. A method comprising treating an individual suffering from or suspected to be suffering from a cancer with a therapy other than an mTOR inhibitor, wherein a cancer cell of the individual has been determined to be mTOR inhibitor resistant by measuring methylation of the PPP2R2B promoter in or of the cancer cell, where hypermethylation of the PPP2R2B promoter, compared to a cancer cell that is not mTOR inhibitor resistant, indicates that the cancer cell is resistant to treatment by an mTOR inhibitor.

9. A method according to claim 5, wherein the cancer is colorectal cancer (CRC).

10. A method according to claim 5, wherein the mTOR inhibitor comprises rapamycin or a derivative thereof.

11. A method according to claim 5, wherein the cancer is selected from the group consisting of: colorectal cancer (CRC), bladder cancer, brain cancer and oesophageal cancer.

12. A method according to claim 7, wherein the cancer is colorectal cancer (CRC).

13. A method according to claim 7, wherein the cancer is selected from the group consisting of: colorectal cancer (CRC), bladder cancer, brain cancer and oesophageal cancer.

14. A method according to claim 8, wherein the cancer is colorectal cancer (CRC).

15. A method according to claim 8, wherein the cancer is selected from the group consisting of: colorectal cancer (CRC), bladder cancer, brain cancer and oesophageal cancer.

16. A method according to claim 7, wherein the cancer is rapamycin resistant colorectal cancer.

17. A method according to claim 8, wherein the cancer is rapamycin resistant colorectal cancer.

18. A method according to claim 7, where measuring expression and/or activity of PDK1 in or of the cancer cell comprised detecting PDK1 mediated Myc phosphorylation activity in or of the cancer cell.

* * * * *